US006743908B2

(12) United States Patent
Filpula et al.

(10) Patent No.: US 6,743,908 B2
(45) Date of Patent: Jun. 1, 2004

(54) SINGLE-CHAIN ANTIGEN-BINDING PROTEINS CAPABLE OF GLYCOSYLATION, PRODUCTION AND USES THEREOF

(75) Inventors: David Filpula, Piscataway, NJ (US); Maoliang Wang, E. Brunswick, NJ (US); Robert Shorr, Edison, NJ (US); Marc Whitlow, El Sobrante, CA (US); Lihsyng S. Lee, Princeton Junction, NJ (US)

(73) Assignee: Enzon, Inc., Bridgewater, NJ (US)

( * ) Notice: Subject to any disclaimer, the term of this patent is extended or adjusted under 35 U.S.C. 154(b) by 0 days.

(21) Appl. No.: 09/956,087

(22) Filed: Sep. 20, 2001

(65) Prior Publication Data

US 2002/0161201 A1 Oct. 31, 2002

Related U.S. Application Data

(62) Division of application No. 09/069,821, filed on Apr. 30, 1998, now Pat. No. 6,323,322.
(60) Provisional application No. 60/044,449, filed on Apr. 30, 1997, provisional application No. 60/063,074, filed on Oct. 27, 1997, provisional application No. 60/067,341, filed on Dec. 2, 1997, and provisional application No. 60/050,472, filed on Jun. 23, 1997.

(51) Int. Cl.$^7$ .............................................. C07H 21/04
(52) U.S. Cl. .................. 536/23.53; 435/69.1; 435/69.6; 435/320.1
(58) Field of Search ............................ 536/23.1, 23.53, 536/24.2; 435/696, 320, 326, 328, 348, 252.8, 254.23, 255.1, 252.51, 325, 69.1, 255.5; 530/387.3; 800/295

(56) References Cited

U.S. PATENT DOCUMENTS

| 4,179,337 A | 12/1979 | Davis et al. |
| 5,122,614 A | 6/1992 | Zalipsky |
| 5,212,075 A | 5/1993 | Bednarski et al. |
| 5,258,498 A | 11/1993 | Huston et al. |
| 5,443,953 A | 8/1995 | Hansen et al. |
| 5,482,858 A | 1/1996 | Huston et al. |
| 5,518,889 A | 5/1996 | Ladner et al. |
| 5,534,254 A | 7/1996 | Huston et al. |
| 5,635,603 A | 6/1997 | Hansen et al. |
| 5,714,350 A | 2/1998 | Co et al. |
| 5,888,773 A | 3/1999 | Jost et al. |
| 5,998,144 A | 12/1999 | Reff et al. |
| 6,323,322 B1 | 11/2001 | Filpula et al. |

FOREIGN PATENT DOCUMENTS

| WO | WO 92/16555 | 10/1992 |
| WO | WO 93/11161 | 6/1993 |
| WO | WO 94/04691 | 3/1994 |
| WO | WO 94/12520 | 6/1994 |
| WO | WO 95/11020 | 4/1995 |
| WO | WO 96/05228 | 2/1996 |
| WO | WO 96/23794 | 8/1996 |

OTHER PUBLICATIONS

Abuchowski, A., et al., "Alteration of Immunological Properties of Bovine Serum Albumin by Covalent Attachment of Polyethylene Glycol," *J. Biol. Chem.* 252:3578–3581, American Society of Biological Chemists, Inc. (1977).

Abuchowski, A., and Davis, F.F., "Soluble Polymer–Enzyme Adducts," in *Enzymes as Drugs*, Holcenberg, J.S., and Roberts, J., Eds., John Wiley & Sons, New York, NY, pp. 367–383 (1981).

Abuchowski, A., et al., "Cancer Therapy With Chemically Modified Enzymes. I. Antitumor Properties Of Polyethylene Glycol–Asparaginase Conjugates," *Cancer Biochem. Biophys.* 7:175–186, Gordon and Breach Science Publishers, Inc. (1984).

Amit, A.G., et al., "Three–Dimensional Structure of an Antigen–Antibody Complex at 2.8 Å Resolution," *Science* 233:747–753, American Association for the advancement of Science (1986).

Anand, N.N., et al., "Bacterial Expression and Secretion of Various single–chain Fv Genes Encoding Proteins Specific for a *Salmonella* Serotype B O–Antigen," *J. Biol. Chem.* 266:21874–21879, The American Society for Biochemistry and Molecular Biology, Inc. (1991).

Andresz, H., et al., "Chemische Synthese verzweigter Polysaccharide, 5," *Makromol. Chem.* 179:301–312, Hüthig & Wepf Verlag Basel (1978).

Beauchamp, C.O., et al., "A New Procedure for the Synthesis of Polyethylene Glycol–Protein Adducts; Effects on Function, Receptor Recognition, and Clearance of Superoxide Dismutase, Lactoferrin, and $\alpha_2$–Macroglobulin," *Anal. Biochem.* 131:25–33, Academic Press Inc. (1983).

Bird, R.E., et al., "Single–Chain Antigen–Binding Proteins," *Science* 242:423–426, American Association for the Advancement of Science (1988).

(List continued on next page.)

Primary Examiner—Larry R. Helms
(74) Attorney, Agent, or Firm—Muserlian, Lucas & Mercanti, LLP

(57) ABSTRACT

The present invention relates to single-chain antigen-binding molecules capable of glycosylation. Compositions of, genetic constructions coding for, and methods for producing monovalent and multivalent single-chain antigen-binding molecules capable of glycosylation are described and claimed. Composition of, genetic constructions coding for, and methods for producing glycosylated monovalent and multivalent single-chain antigen-binding molecules capable of polyalkylene oxide conjugation are described and claimed. The invention also relates to methods for producing a polypeptide having increased glycosylation and the polypeptide produced by the described method. Uses resulting from the multifunctionality of a glycosylated/polyalkylene oxide conjugated antigen-binding protein are also described and claimed.

67 Claims, 22 Drawing Sheets

OTHER PUBLICATIONS

Cumber, A.J., et al., "Comparative Stabilities In Vitro And In Vivo Of A Recombinant Mouse Antibody FvCys Fragment And A bisFvCys Conjugate," *J. Immunol.* 149:120–126, American Association of Immunologists (1992).

Delente, J.J., "Glycosylation revisited," *Trends Biotechnol.* 3:218, Elsevier Science (1985).

Desplancq, D., et al., "Multimerization behaviour of single chain Fv variants for the tumour–binding antibody B72.3," *Protein Engineering* 7:1027–1033, Oxford University Press (1994).

Filpula, D., "PEGylated sFv and Glycosylated sFv," abstract of presentation given at IBC's *Eight Annual International Conference on Antibody Engineering*, Dec. 3–5, 1997, Coronado, California, with excerpts of program (Dec. 3, 1997).

Filpula, D., et al., "Production of single–chain Fv monomers and multimers," in *Antibody Engineering: A Practical Approach*, McCafferty, J., et al., eds., IRL Press (Oxford University Press), Oxford, UK, pp. 253–268 (Aug. 1996).

Filpula, D., "PEGylated sFv and Glycosylated sFv," Abstract for: IBC's Eighth Annual International Conferences on Antibody Engineering: New Technology, Application & Commercialization, Dec. 3, 1997.

Filpula, D., "PEGylated sFv and Glycosylated sFv," Part of Booklet distributed at: IBC's Eighth Annual International Conference on Antibody Engineering: New Techology, Application & Commercialization, Dec. 3, 1997.

Filpula, D., "PEGylated sFv and Glycosylated sFv," Slide Presentation at: IBC's Eighth Annual International Conference on Antibody Engineering: New Technology, Application & Commercialization, Dec. 3, 1997.

George, A.J.T., et al., "Production Of A Bispecific Antibody By Linkage Of Two Recombinant Single Chain Fv Molecules," *J. Cell. Biochem.* (*Suppl. 15E*): 127, Abstract No. N206, Wiley–Liss (1991).

Gavel, Y., and von Heijne, G., "Sequence differences between glycosylated and non–glycosylated Asn–X–Thr/Ser acceptor sites: implications for protein engineering," *Protein Engineering* 3:433–442, Oxford University Press (1990).

Greenman, J., et al., "The use of intracellular single–chain antibody fragments to inhibit specifically the expression of cell surface molecules," *J. Immunol. Meth.* 194:169–180, Elsevier Science B.V. (Aug. 1996).

Greenwald, R.B., "Drug delivery systems: anticancer prodrugs and their polymeric conjugates," *Exp. Opin. Ther. Patents* 7:601–609, Ashley Publications Ltd. (Jun. 1997).

Holliger, P., et al., ""Diabodies": Small bivalent and bispecific antibody fragments," *Proc. Natl. Acad. Sci. USA* 90:6444–6448, The National Academy of Sciences (1993).

Hoogenboom, H.R., "Mix and match: Building manifold binding sites," *Nature Biotechnology* 15:125–126, Nature Publishing Group (Feb. 1997).

Ishihara, H., et al., "Development Of Neoglycoproteins Conjugated With Natural Oligosaccharides Through Carboxyl Residues Of Proteins And Its Application To Recombinant Human Interleukin 1," *Biochem. Mol. Biol. Inter.* 31:527–535, Academic Press Australia (1993).

Jost, C.R., et al., "Mammalian Expression and Secretion of Functional Single–chain Fv Molecules," *J. Biol. Chem.* 269:26267–26273, American Society for Biochemistry and Molecular Biology (1994).

Kasturi, L., et al., "The Hydroxy Amino Acid in an Asn–X––Ser/Thr Sequon Can Influence N–Linked Core Glycosylation Efficiency and the Level of Expression of a Cell Surface Glycoprotein," *J. Biol. Chem.* 270:14756–14761, American Society for Biochemistry and Molecular Biology, Inc. (1995).

Keck, P.C., and Huston, J.S., "Symmetry of Fv Architecture Is Conductive to Grafting a Second Antibody Binding Site in the Fv Region," *Biophys. J.* 71:2002–2011, Biophysical Society (Oct. 1996).

Knight, P., "The Carbohydrate Frontier," *Biotechnology* 7:35–40, Nature Publishing (1989).

Leung, S.–o., et al., "Engineering a Unique Glycosylation Site for Site–Specific Conjugation of Haptens to Antibody Fragments," *J. Immunol.* 154:5919–5926, American Association of Immunologists (1995).

Leung, S.–o., et al., "Effect Of Vk Framework–l Glycosylation On The Binding Affinity Of Lymphoma–Specific Murine And Chimeric LL2 Antibodies And Its Potential Use As A Novel Conjugation Site,"*Int. J. Cancer* 60:534–538, Wiley–Liss, Inc. (1995).

Muyldermans, S., et al., "Sequence and structure of $V_H$ domain from naturally occurring camel heavy chain immunoglobulins lacking light chains," *Protein Eng.* 7:1129–1135, Oxford University Press (1994).

Panka, D.J., et al., "Variable region framework differences result in decreased or increased affinity of variant anti––digoxin antibodies," *Proc. Natl. Acad. Sci. USA* 85:3080–3084, The National Academy of Sciences (1988).

Pendri, A., et al., "PEG Modified Anticancer Drugs: Synthesis and Biological Activity," *J. Bioactive Compatible Polymers* 11:122–134, Technomic Publishing Co., Inc. (Apr. 1996).

Prammer, K.V., and L. Otvos, Jr., "Structural Effects Of Glycosylation On The C–Terminal Pentapeptide Of Peptide T," *Biomed. Peptides Proteins Nucleic Acids* 1:221–226, Mayflower Worldwide Ltd. (1995).

Reiter, Y., et al., "Engineering antibody Fv fragments for cancer detection and therapy: Disulfide–stabilized Fv fragments," *Nature Biotechnol.* 14:1239–1245, Nature Publishing (Oct. 1996).

Roget's II, The New Thesaurus, The American Heritage Dictionary, Eds., Houghton Mifflin Company, Boston, Massachusetts, pp. 1052 (1988).

Rudikoff, S., et al., "Single amino acid substitution altering antigen–binding specificity," *Proc. Natl. Acad. Sci. USA* 79:1979–1983, The National Academy of Sciences (1982).

Schaffhausen, B.S., "Designing and Using Site–Specific Antibodies to Synthetic Peptides," in *Hybridoma Technology in the Biosciences and Medicine*, Springer, T.A., Ed., Plenum Press, New York, NY, pp. 355–373 (1985).

Shih, L.B., et al., "Anthracycline Immunoconjugates Prepared by a Site–specific Linkage via an Amino–Dextran Intermediate Carrier," *Cancer Res.* 51:4192–4198, American Association for Cancer Research (1991).

Simon, P.M., "Pharmaceutical oligosaccharides," *DDT* 1:522–528, Elsevier Science Ltd. (Dec. 1996).

Veronese, F.M., et al., "Surface Modification of Proteins. Activation of Monomethoxy–Polyethylene Glycols by Phenylchloroformates and Modification of Ribonuclease and Superoxide Dismutase," *Applied Biochem. Biotechnol.* *11*:141–152, The Human Press Inc. (1985).

Wang, M., et al., "Single–chain Fv with manifold N–glycans as bifunctional scaffolds for immunomolecules," *Protein Engineering 11*:1277–1283, Oxford University Press (1998).

Whitlow, M., et al., "Multivalent Fvs: characterization of single–chain Fv oligomers and preparation of a bispecific Fv," *Protein Engineering 7*:1017–1026, Oxford University Press (1994).

Whitlow, M., et al., "1.85 Å structure of anti–fluorescein 4–4–20 Fab," *Protein Engineering 8*:749–761, Oxford University Press (1995).

Wilchek, M., and Bayer, E.A., "Labeling Glycoconjugates with Hydrazide Reagents," *Meth. Enzymol. 138*:429–442, Academic Press, Inc. (1987).

Wright, A., and Morrison, S.L., "Antibody Variable region glycosylation: biochemical and clinical effects," *Springer Semin. Immunopathol. 15*:259–273, Springer–Verlag (1993).

CC49 V$_L$

```
   D   V   V   M   S   Q   S   P   S   S   L   P   V   S   V
                                               12          15
  GAC GTC GTG ATG TCA CAG TCT CCA TCC TCC CTA CCT GTG TCA GTT
  Aat II                                         (AAC)
                                                  *1

27C
   G   E   K   V   T   L   S   C   K   S   S   Q   S   L   L
  GGC GAG AAG GTT ACT TTG AGC TGC AAG TCC AGT CAG AGC CTT TTA

39
   Y   S   G   N   Q   K   N   Y   L   A   W   Y   Q   Q   K
  TAT AGT GGT AAT CAA AAG AAC TAC TTG GCC TGG TAC CAG CAG AAA

54
   P   G   Q   S   P   K   L   L   I   Y   W   A   S   A   R
  CCA GGG CAG TCT CCT AAA CTG CTG ATT TAC TGG GCA TCC GCT AGG

69
   E   S   G   V   P   D   R   F   T   G   S   G   S   G   T
  GAA TCT GGG GTC CCT GAT CGC TTC ACA GGC AGT GGA TCT GGG ACA 77                                          84
   D   F   T   L   S   I   S   S   V   K   T   E   D   L   A
  GAT TTC ACT CTC TCC ATC AGC AGT GTG AAG ACT GAA GAC CTG GCA
                                  (AAC)   (AGT)
                                   *2

99
   V   Y   Y   C   Q   Q   Y   Y   S   Y   P   L   T   F   G
  GTT TAT TAC TGT CAG CAG TAT TAT AGC TAT CCC CTC ACG TTC GGT

218 Linker

A   G   T   K   L   V   L   K   G   S   T   S   G   S   G
  GCT GGG ACC AAG CTT GTG CTG AAA GGC TCT ACT TCC GGT AGC GGC
          Hind III                      (AAC)
                                         *3
                                                  CC49 V$_H$
                                                        4
   K   P   G   S   G   E   G   S   T   K   G   Q   V   Q   L
  AAA CCC GGG AGT GGT GAA GGT AGC ACT AAA GGT CAG GTT CAG CTG
      Sma I                                              Pvu II 13                                  19
   Q   Q   S   D   A   E   L   V   K   P   G   A   S   V   K
  CAG CAG TCT GAC GCT GAG TTG GTG AAA CCT GGG GCT TCA GTG AAG
                                  (AAC)   (TCT)
                                   *4

34
   I   S   C   K   A   S   G   Y   T   F   T   D   H   A   I
  ATT TCC TGC AAG GCT TCT GGC TAC ACC TTC ACT GAC CAT GCA ATT
```

FIG.1A

```
                                                        49
H   W   V   K   Q   N   P   E   Q   G   L   E   W   I   G
CAC TGG GTG AAA CAG AAC CCT GAA CAG GGC CTG GAA TGG ATT GGA

63
Y   F   S   P   G   N   D   D   F   K   Y   N   E   R   F
TAT TTT TCT CCC GGA AAT GAT GAT TTT AAA TAC AAT GAG AGG TTC

78
K   G   K   A   T   L   T   A   D   K   S   S   S   T   A
AAG GGC AAG GCC ACA CTG ACT GCA GAC AAA TCC TCC AGC ACT GCC 82B                                         90
Y   V   Q   L   N   S   L   T   S   E   D   S   A   V   Y
TAC GTG CAG CTC AAC AGC CTG ACA TCT GAG GAT TCT GCA GTG TAT
                   (AAC)
                    *5

107
F   C   T   R   S   L   N   M   A   Y   W   G   Q   G   T
TTC TGT ACA AGA TCC CTG AAT ATG GCC TAC TGG GGT CAA GGA ACC

112
S   V   T   V   S ( N   K   T   S )
TCA GTC ACC GTC TCC AAC AAG ACC AGT TAA TAGGATCC
                 *6                       Bam HI
```

FIG. 1B

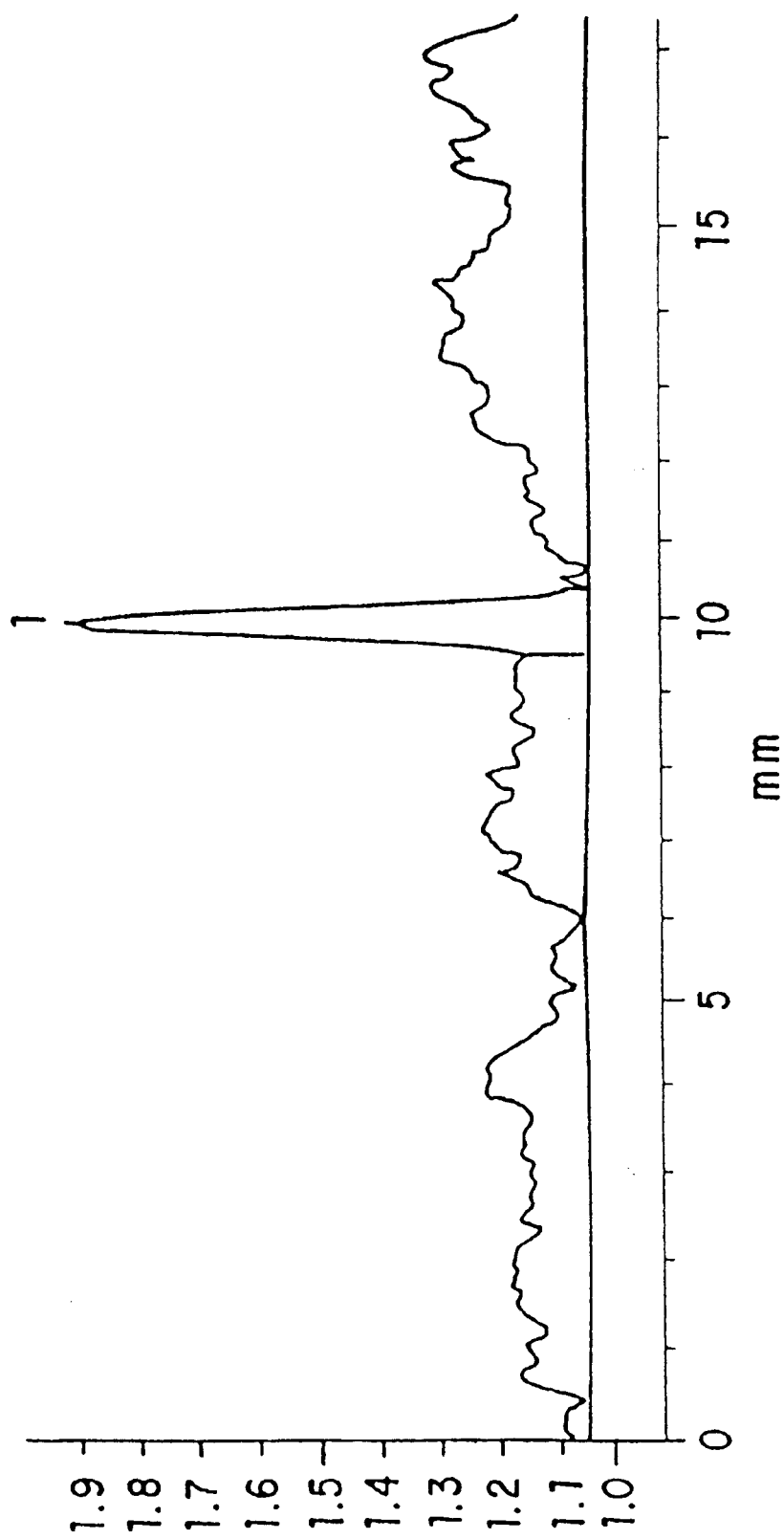
FIG. 5B-a

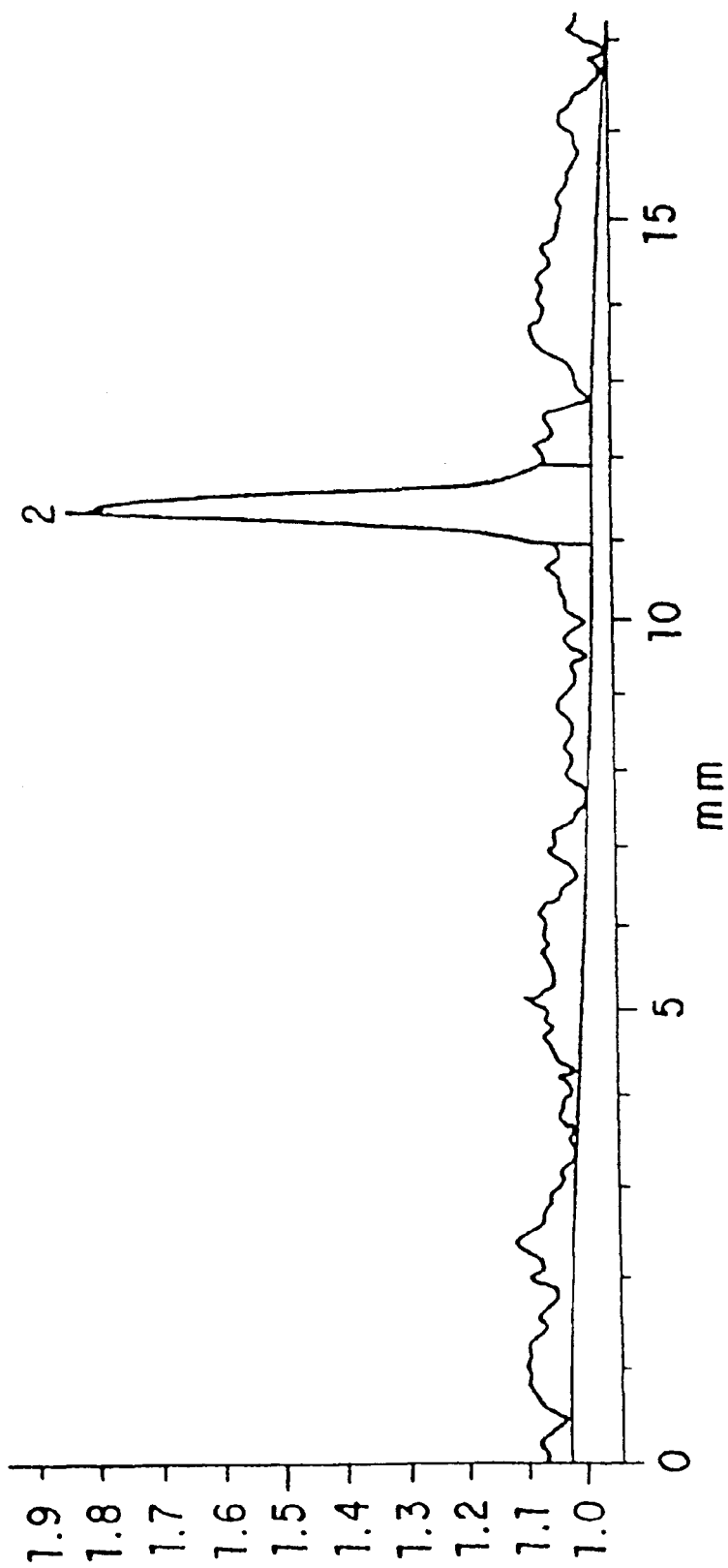
FIG. 5B-b

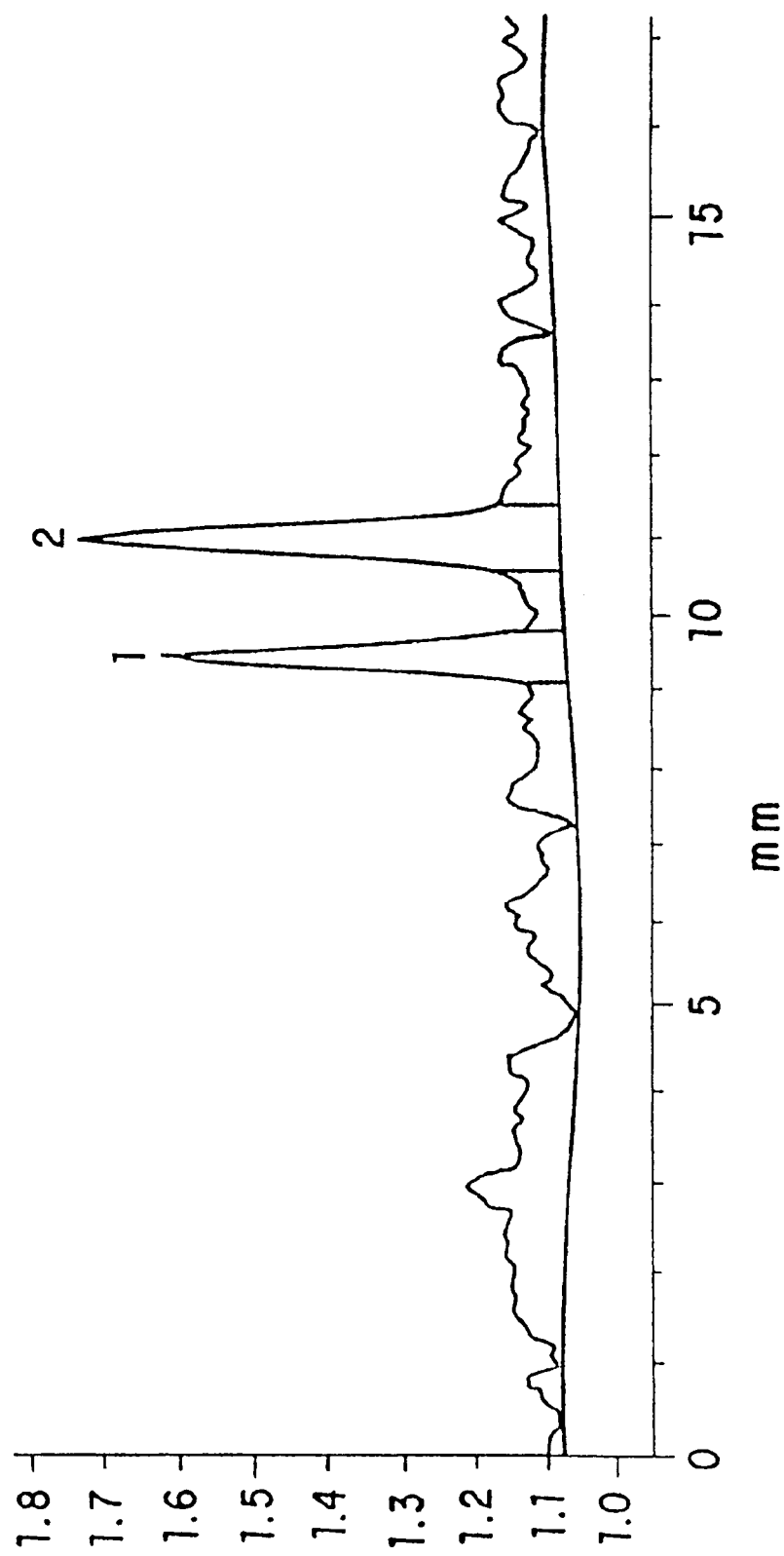
FIG. 5B-c $V_L$ ($V_\kappa I$)

```
                          12                              22
D  I  Q  M  T  Q  S  P  S  S  L  S  A  S  V  G  D  R  V  T  I  T
                                 *
                                (N)
                                            41
C  R  A  S  Q  S  L  V  S  I  S  N  Y  L  A  W  Y  Q  Q  K  P  G
                                                     63
K  A  P  K  L  L  I  Y  A  A  S  S  L  E  S  G  V  P  S  R  F  S
                              77                  85
G  S  G  S  G  T  D  F  T  L  T  I  S  S  L  Q  P  E  D  F  A  T
                                          *
                                        (N    T)  A
                                                      106
Y  Y  C  Q  Q  Y  N  S  L  P  F  W  T  F  G  Q  G  T  K  V  E  I
```

218 Linker                                           $V_H$ ($V_H III$)

218 Linker                                                C6.5 V_H

218 Linker

1. Molecular weight marker
2. Native un-pegylated gCC49/2
   (nonglycosylated fraction and glycosylated fraction)
3. Low Molecular weight Fractions
   (nonglycosylated single chain antibody)
4. High molecular weight fraction
   (PEGylated glycosylated single chain gCC/2)

Lane Sample
1  Native gCC49/3
2  gCC49/3-HZ5,000-PEG highly pegylated fraction
3  gCC49/3-HZ5,000-PEG less pegylated fraction
4  Molecular Weight Marker
   116.3, 97.4, 66.3, 55.4 36.5, 31 kD
   26.5 (CC49/218-native), 21.5, 14.4, 6 kD

SINGLE-CHAIN ANTIGEN-BINDING PROTEINS CAPABLE OF GLYCOSYLATION, PRODUCTION AND USES THEREOF

The present application is a divisional application of U.S. Appl. No. 09/069,821, filed Apr. 30, 1998, now U.S. Pat. No. 6,323,322, which claims benefit of the filing date of U.S. Provisional Appl. No. 60/044,449, filed Apr. 30, 1997, U.S. Provisional Appl. No. 60/063,074, filed Oct. 27, 1997, U.S. Provisional Appl. No. 60/067,341, filed Dec. 2, 1997, and U.S. Provisional Appl. No. 60/050,472, filed Jun. 23, 1997, each of which disclosure is incorporated herein in entirety by reference.

BACKGROUND OF THE INVENTION

1. Field of the Invention

The present invention relates generally to single-chain antigen-binding molecules capable of glycosylation. More specifically, the invention relates to antigen-binding proteins having Asn-linked glycosylation sites capable of attaching a carbohydrate moiety. The invention also relates to multivalent antigen-binding molecules capable of glycosylation. The invention further relates to glycosylated antigen-binding molecules capable of polyalkylene oxide conjugation. Compositions of, genetic constructions for, methods of use, and methods for producing glycosylated antigen-binding proteins capable of polyalkylene oxide conjugation are disclosed. The invention also relates to methods for producing a polypeptide having increased glycosylation and the polypeptide produced by the described methods.

2. Description of the Background Art

Antibodies are proteins generated by the immune system to provide a specific molecule capable of complexing with an invading molecule, termed an antigen. Natural antibodies have two identical antigen-binding sites, both of which are specific to a particular antigen. The antibody molecule "recognizes" the antigen by complexing its antigen-binding sites with areas of the antigen termed epitopes. The epitopes fit into the conformational architecture of the antigen-binding sites of the antibody, enabling the antibody to bind to the antigen.

The IgG antibody, e.g., is composed of two identical heavy and two identical light polypeptide chains, held together by interchain disulfide bonds. The remainder of this discussion on antibodies will refer only to one pair of light/heavy chains, as each light/heavy pair is identical. Each individual light and heavy chain folds into regions of approximately 110 amino acids, assuming a conserved three-dimensional conformation. The light chain comprises one variable region ($V_L$) and one constant region ($C_L$), while the heavy chain comprises one variable region ($V_H$) and three constant regions ($C_H1$, $C_H2$ and $C_H3$). Pairs of regions associate to form discrete structures. In particular, the light and heavy chain variable regions associate to form an "Fv" area which contains the antigen-binding site.

Recent advances in immunobiology, recombinant DNA technology, and computer science have allowed the creation of single polypeptide chain molecules that bind antigen. These single-chain antigen-binding molecules ("SCA") or single-chain variable fragments of antibodies ("sFv") incorporate a linker polypeptide to bridge the individual variable regions, $V_L$ and $V_H$, into a single polypeptide chain. A description of the theory and production of single-chain antigen-binding proteins is found in Ladner et al., U.S. Pat. Nos. 4,946,778, 5,260,203, 5,455,030 and 5,518,889. The single-chain antigen-binding proteins produced under the process recited in the above U.S. patents have binding specificity and affinity substantially similar to that of the corresponding Fab fragment. A computer-assisted method for linker design is described more particularly in Ladner et al., U.S. Pat. Nos. 4,704,692 and 4,881,175, and WO 94/12520.

The in vivo properties of SCA polypeptides are different from MAbs and antibody fragments. Due to their small size, SCA polypeptides clear more rapidly from the blood and penetrate more rapidly into tissues (Milenic, D. E. et al., Cancer Research 51:6363–6371 (1991); Colcher et al., J. Natl. Cancer Inst. 82:1191 (1990); Yokota et al., Cancer Research 52:3402 (1992)). Due to lack of constant regions, SCA polypeptides are not retained in tissues such as the liver and kidneys. Due to the rapid clearance and lack of constant regions, SCA polypeptides will have low immunogenicity. Thus, SCA polypeptides have applications in cancer diagnosis and therapy, where rapid tissue penetration and clearance, and ease of microbial production are advantageous.

A multivalent antigen-binding protein has more than one antigen-binding site. A multivalent antigen-binding protein comprises two or more single-chain protein molecules. Enhanced binding activity, di- and multi-specific binding, and other novel uses of multivalent antigen-binding proteins have been demonstrated. See, Whitlow, M., et al., Protein Engng. 7:1017–1026 (1994); Hoogenboom, H. R, Nature Biotech. 15:125–126 (1997); and WO 93/11161.

Carbohydrate modifications of proteins fall into three general categories: N-linked (or Asn-linked) modification of asparagine, O-linked modification of serine or threonine and glycosyl-phosphatidylinositol derivation of the C-terminus carboxyl group. Each of these transformations is catalyzed by one or more enzymes which demonstrate different peptide sequence requirements and reaction specificities. N-linked glycosylation is catalyzed by a single enzyme, oligosaccharyl transferase (OT), and involves the co-translational transfer of a lipid-linked tetradecasaccharide ($GlcNAc_2$-$Man_9$-$Glc_3$) to an asparagine side chain within a nascent polypeptide (see, Imperiali, B. and Hendrickson, T. L., Bioorgarnic & Med Chem. 3:1565–1578 (1995)). The asparagine residue must reside within the tripeptide N-linked glycosylation consensus sequence Asn-Xaa-Thr/Ser (NXT/S), where Xaa can be any of the 20 natural amino acids except proline.

A natural N-linked glycosylation sequence (Asn-Val-Thr) at amino acid positions 18–20 (Kabat's numbering) was identified in the framework-1 (FR-1) region of the light chain variable domain of a murine anti-B cell lymphoma antibody, LL-2 (Leung, S.-o. et al., J. Immunol. 154:5919–5926 (1995)). By a single Arg to Asn mutation, an N-linked glycosylation sequence similar to that of LL-2 was introduced in the FR-1 segment of a nonglycosylated, humanized anti-carcinoembryonic Ag (CEA) Ab, MN-14 (Leung, S.-O. et al., J. Immunol. 154:5919–5926 (1995), which disclosure is incorporated herein by reference).

An sFv having a C-terminus that has cross-linking means by disulfide bonds at cysteine residues has been reported (Huston et al., U.S. Pat. No. 5,534,254). A monoclonal antibody has also been reported that is covalently bound to a diagnostic or therapeutic agent through a carbohydrate moiety at an Asn-linked glycosylation site at about amino acid position 18 of the $V_L$ region (Hansen et al., U.S. Pat. No. 5,443,953). Binding studies of an anti-dextran antibody that is Asn-linked glycosylated in the $V_H$ chain have been performed which show that slight changes in the position of the Asn-linked carbohydrate moiety in the $V_H$ region result in substantially different effects on antigen binding (Wright et al., *EMBO J.* 10:2717–2723 (1991)). It has also been shown that glycosylation at position 19 within the $V_H$ region of an sFv enhanced expression of the overall amount of sFv intracellularly, of which approximately half was glycosylated (Greenman, J., et al., *J. Immunol. Methods* 194:169–180 (1996)), and enhanced synthesis and secretion of the glycosylated sFv over the nonglycosylated sFv (Jost, C. R., et al., *J. Biol. Chem.* 269:26267–26273 (1994)). Co et al., U.S. Pat. No. 5,714,350, relates to increasing binding affinity of an antibody by eliminating a glycosylation site.

The covalent attachment of strands of a polyalkylene glycol or polyalkylene oxide to a polypeptide molecule is disclosed in U.S. Pat. No. 4,179,337 to Davis et al., as well as in Abuchowski and Davis "Enzymes as Drugs," Holcenberg and Roberts, Eds., pp. 367–383, John Wiley and Sons, New York (1981), and Zalipsky et al., WO 92/16555. These references disclosed that proteins and enzymes modified with polyethylene glycols have reduced immunogenicity and antigenicity and have longer lifetimes in the bloodstream, compared to the parent compounds. The resultant beneficial properties of the chemically modified conjugates are very useful in a variety of therapeutic applications.

To effect covalent attachment of polyethylene glycol (PEG) and similar poly(alkylene oxides) to a molecule, the hydroxyl end groups of the polymer must first be converted into reactive functional groups. This process is frequently referred to as "activation" and the product is called "activated PEG."

Hydrazides readily form relatively stable hydrazone linkages by condensation with aldehydes and ketones (Andresz, H. et al., *Makromol. Chem.* 179:301 (1978)). This property has been used extensively for modification of glycoproteins through oxidized oligosaccharide moieties (Wilchek, M. & Bayer, E. A., *Meth. Enzymol.* 138:429 (1987)).

Activated PEG-hydrazide allows it to react with an aldehyde group. Aldehyde is normally absent on the polypeptide chain of a protein. However, if a protein contains carbohydrate moieties, then the carbohydrate can be activated to provide a reactive aldehyde group by oxidation of the sugar ring such as mannose. Methods for activation of immunoconjugates are described in Sela et al., *Immunoconjugates*, Vogel ed., Oxford University Press (1987). In this way, PEG-hydrazide can be conjugated covalently to the protein via the carbohydrate structure. Zalipsky, S., et al., WO 92/16555, describes PAO covalently bonded to an oxidized carbohydrate moiety of the glycopolypeptide by a linkage containing a hydrazide or hydrazone functional group bound to the polymer. The oxidation of the carbohydrate moiety produces reactive aldehydes. The hydrazone linkage is formed by reacting an acyl hydrazine derivative of the polymer containing the peptide sequence with these aldehyde groups.

The prior art has activated the hydroxyl group of PEG with cyanuric chloride and the resulting compound is then coupled with proteins (Abuchowski et al., *J. Biol. Chem.* 252:3578 (1977); Abuchowski & Davis, supra (1981)). However, there are disadvantages in using this method, such as the toxicity of cyanuric chloride and its non-specific reactivity for proteins having functional groups other than amines, such as free essential cysteine or tyrosine residues.

In order to overcome these and other disadvantages, alternative activated PEGs, such as succinimidyl succinate derivatives of PEG ("SS-PEG"), have been introduced (Abuchowski et al., *Cancer Biochem. Biophys.* 7:175–186 (1984)). It reacts quickly with proteins (30 minutes) under mild conditions yielding active yet extensively modified conjugates.

Zalipsky, in U.S. Pat. No. 5,122,614, disclosed poly (ethylene glycol)-N-succinimide carbonate and its preparation. This form of the polymer was said to react readily with the amino groups of proteins, as well as low molecular weight peptides and other materials that contain free amino groups.

Other linkages between the amino groups of the protein, and the PEG are also known in the art, such as urethane linkages (Veronese et al., *Appl. Biochem. Biotechnol.* 11:141–152 (1985)), carbamate linkages (Beauchamp et al., *Analyt. Biochem.* 131:25–33 (1983)), and others.

Polyalkylene oxide modification of sFvs is disclosed in U.S. Provisional Patent Application No. 60/050,472, filed Jun. 23, 1997, which disclosure is incorporated herein by reference.

The activated polymers can also be reacted with a therapeutic agent having nucleophilic functional groups that serve as attachment sites. One nucleophilic functional group commonly used as an attachment site is the ε-amino groups of lysines. Free carboxylic acid groups, suitably activated carbonyl groups, oxidized carbohydrate moieties and mercapto groups have also been used as attachment sites.

Conjugation of poly(ethylene glycol) or poly(alkylene oxide) with small organic molecules is described in Greenwald, R. B., *Exp. Opin. Ther. Patents* 7:601–609 (1997), Enzon Inc., WO 95/11020, and Enzon Inc., WO 96/23794, which disclosures are all incorporated herein by reference. Compositions based on the use of various linker groups between the PEG ballast and the active drug are described in WO 96/23794.

SUMMARY OF THE INVENTION

The invention is directed to a single-chain antigen-binding polypeptide capable of glycosylation, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide has at least one tripeptide Asn-linked glycosylation sequence comprising Asn-Xaa-Yaa, wherein Xaa is an amino acid other than proline and Yaa is threonine or serine, wherein the tripeptide glycosylation sequence is capable of attaching a carbohydrate moiety at the Asn residue located at a position selected from the group consisting of (i) the amino acid position 11, 12, 13, 14 or 15 of the light chain variable region; (ii) the amino acid position 77, 78 or 79 of the light chain variable region; (iii) the amino acid position 11, 12, 13, 14 or 15 of the heavy chain variable region; (iv) the amino acid position 82B, 82C or 83 of the heavy chain variable region; (v) any amino acid position of the peptide linker; (vi) adjacent to the C-terminus of the second polypeptide (b); and (vii) combinations thereof, wherein the glycosylated single-chain antigen-binding polypeptide is capable of binding an antigen.

The invention is further directed to a polynucleotide encoding a single-chain antigen-binding polypeptide capable of glycosylation, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide has at least one tripeptide Asn-linked glycosylation sequence comprising Asn-Xaa-Yaa, wherein Xaa is an amino acid other than proline and Yaa is threonine or serine, wherein the tripeptide glycosylation sequence is capable of attaching a carbohydrate moiety at the Asn residue located at a position selected from the group consisting of (i) the amino acid position 11, 12, 13, 14 or 15 of the light chain variable region; (ii) the amino acid position 77, 78 or 79 of the light chain variable region; (iii) the amino acid position 11, 12, 13, 14 or 15 of the heavy chain variable region; (iv) the amino acid position 82B, 82C or 83 of the heavy chain variable region; (v) any amino acid position of the peptide linker; (vi) adjacent to the C-terminus of the second polypeptide (b); and (vii) combinations thereof, wherein the glycosylated single-chain antigen-binding polypeptide is capable of binding an antigen.

The polynucleotide may be DNA or RNA.

The invention is directed to a replicable cloning or expression vehicle comprising the above described DNA sequence. The invention is also directed to such vehicle which is a plasmid. The invention is further directed to a host cell transformed with the above described DNA. The host cell may be a bacterial cell, a yeast cell or other fungal cell, an insect cell or a mammalian cell line. A preferred host is *Pichia pastoris*.

The invention is directed to a method of producing a single-chain antigen-binding polypeptide capable of glycosylation, comprising:

(a) providing a first polynucleotide encoding a first polypeptide comprising the antigen binding portion of the variable region of an antibody heavy or light chain;

(b) providing a second polynucleotide encoding a second polypeptide comprising the antigen binding portion of the variable region of an antibody heavy or light chain; and (c) linking the first and second polynucleotides (a) and (b) with a third polynucleotide encoding a peptide linker into a fourth polynucleotide encoding a single chain polypeptide having an antigen binding site, wherein the single-chain antigen-binding polypeptide has at least one tripeptide Asn-linked glycosylation sequence comprising Asn-Xaa-Yaa, wherein Xaa is an amino acid other than proline and Yaa is threonine or serine, wherein the tripeptide glycosylation sequence is capable of attaching a carbohydrate moiety at the Asn residue located at a position selected from the group consisting of (i) the amino acid position 11, 12, 13, 14 or 15 of the light chain variable region; (ii) the amino acid position 77, 78 or 79 of the light chain variable region; (iii) the amino acid position 11, 12, 13, 14 or 15 of the heavy chain variable region; (iv) the amino acid position 82B, 82C or 83 of the heavy chain variable region; (v) any amino acid position of the peptide linker; (vi) adjacent to the C-terminus of the second polypeptide (b); and (vii) combinations thereof, wherein the glycosylated single-chain antigen-binding polypeptide is capable of binding an antigen; and (d) expressing the single-chain antigen-binding polypeptide of (c) in the host, thereby producing a single-chain antigen-binding polypeptide capable of glycosylation.

In the method as according to the invention, the host cell is capable of catalyzing glycosylation. The host cell is a plant cell, a bacterial cell, a yeast cell or other fungal cell, an insect cell or a mammalian cell line. A preferred host cell is *Pichia pastoris*.

The invention is further directed to a multivalent single-chain antigen-binding protein, comprising two or more single-chain antigen-binding polypeptides, each single-chain antigen-binding polypeptide comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein the single-chain antigen-binding polypeptide has at least one tripeptide Asn-linked glycosylation sequence comprising Asn-Xaa-Yaa, wherein Xaa is an amino acid other than proline and Yaa is threonine or serine, wherein the tripeptide glycosylation sequence is capable of attaching a carbohydrate moiety at the Asn residue located at a position selected from the group consisting of (i) the amino acid position 11, 12, 13, 14 or 15 of the light chain variable region; (ii) the amino acid position 77, 78 or 79 of the light chain variable region; (iii) the amino acid position 11, 12, 13, 14 or 15 of the heavy chain variable region; (iv) the amino acid position 82B, 82C or 83 of the heavy chain variable region; (v) any amino acid position of the peptide linker; (vi) adjacent to the C-terminus of the second polypeptide (b); and (vii) combinations thereof, wherein the glycosylated single-chain antigen-binding polypeptide is capable of binding an antigen.

In the above described embodiments of the invention, the tripeptide glycosylation sequence may be capable of attaching a carbohydrate moiety at the Asn residue located at a position selected from the group consisting of (i') the amino acid position 12 of the light chain variable region; (ii') the amino acid position 77 of the light chain variable region; (iii') the amino acid position 13 of the heavy chain variable region; (iv') the amino acid position 82B of the heavy chain variable region; (v') the amino acid position 2 of the peptide linker; (vi') adjacent to the C-terminus of the second polypeptide (b); and (vii') combinations thereof, wherein the glycosylated single-chain antigen-binding polypeptide is capable of binding an antigen.

In the above described embodiments of the invention, at least one single-chain antigen-binding polypeptide may have at least two tripeptide glycosylation sequences in tandem such that the Asn residues are separated by two amino acid residues and/or at least one set of two overlapping tripeptide glycosylation sequences such that the Asn residues are adjacent. At least one single-chain antigen-binding polypeptide may have three tripeptide glycosylation sequences in tandem. At least one single-chain antigen-binding polypeptide may have at least two sets of two tandem tripeptide glycosylation sequences and at least two sets of two overlapping tripeptide glycosylation sequences.

Also in the above described embodiments of the invention, the Asn residue of the tripeptide glycosylation sequence may be attached to a carbohydrate moiety. The carbohydrate moiety may further be conjugated to polyalkylene oxide. The carbohydrate and/or polyalkylene moieties may be conjugated to one or plurality of peptide, lipid, nucleic acid, drug, toxin, chelator, boron addend or detectable label molecule(s). The carbohydrate and/or polyalkylene oxide moieties may be conjugated to a carrier having one or plurality of peptide, lipid, nucleic acid, drug, toxin, chelator, boron addend or detectable label molecule(s) bound to the carrier.

In the above described embodiments of the invention, the C-terminus of the second polypeptide (b) may be the native C-terminus of the second polypeptide (b). In the alternative, the C-terminus of the second polypeptide (b) may comprise a deletion of one or plurality of amino acid residue(s), such that the remaining N-terminus amino acid residues of the second polypeptide are sufficient for the glycosylated polypeptide to be capable of binding an antigen. In the alternative, the C-terminus of the second polypeptide may comprise an addition of one or plurality of amino acid residue(s), such that the glycosylated polypeptide is capable of binding an antigen. In one embodiment, the Asn residue of the glycosylation sequence may be located adjacent to any of the above mentioned C-terminus of the second polypeptide and the glycosylation sequence may be followed by at least one amino acid residue. In the alternative, the glycosylation sequence may be followed by two, three, four or five amino acid residues.

In a preferred embodiment of the invention, the first polypeptide (a) may comprise the antigen binding portion of the variable region of an antibody light chain and the second polypeptide (b) comprises the antigen binding portion of the variable region of an antibody heavy chain.

The invention is also directed to a method of detecting an antigen suspected of being in a sample, comprising:
(a) contacting the sample with the glycosylated polypeptide or multivalent protein of the invention, wherein the carbohydrate moiety is conjugated to one or plurality of detectable label molecule(s), or conjugated to a carrier having one or plurality of detectable label molecule(s) bound to the carrier; and
(b) detecting whether the glycosylated single-chain antigen-binding polypeptide has bound to the antigen.

The invention is further directed to a method of imaging the internal structure of an animal, comprising administering to the animal an effective amount of the glycosylated polypeptide or multivalent protein of the invention, wherein the carbohydrate moiety is conjugated to one or plurality of detectable label or chelator molecule(s), or conjugated to a carrier having one or plurality of detectable label or chelator molecule(s) bound to the carrier, and measuring detectable radiation associated with the animal. Animal includes human and nonhuman.

The invention is also directed to a method for treating a targeted disease, comprising administering an effective amount of a composition comprising the glycosylated polypeptide or multivalent protein of the invention and a pharmaceutically acceptable carrier vehicle, wherein the carbohydrate moiety is conjugated to one or plurality of peptide, lipid, nucleic acid, drug, toxin, boron addend or radioisotope molecule(s), or conjugated to a carrier having one or plurality of drug, toxin, boron addend or radioisotope molecule(s) bound to the carrier.

The above described methods may be facilitated with the glycosylated polypeptide or multivalent protein of the invention, which is conjugated to polyalkylene oxide which may also be conjugated to one or plurality of peptide, lipid, nucleic acid, drug, toxin, chelator, boron addend or detectable label molecule(s).

The invention also relates to (1) a method of producing a polypeptide having increased glycosylation, comprising: (a) providing to a polynucleotide encoding the polypeptide at least two tripeptide Asn-linked glycosylation sequences, wherein each tripeptide glycosylation sequence comprises Asn-Xaa-Yaa, wherein Xaa is an amino acid other than proline and Yaa is threonine or serine, and wherein the tripeptide glycosylation sequences are in tandem such that the Asn residues are separated by two amino acid residues; and (b) expressing the polynucleotide in a host cell capable of attaching a carbohydrate moiety at the Asn residues, and (2) a polypeptide having increased glycosylation produced by the described process.

The invention further relates to (1) a method of producing a polypeptide having increased glycosylation, comprising: (a) providing to a polynucleotide encoding the polypeptide at least one set of two tripeptide Asn-linked glycosylation sequences, wherein each tripeptide glycosylation sequence comprises Asn-Xaa-Yaa, wherein Xaa is an amino acid other than proline and Yaa is threonine or serine, and wherein the two tripeptide glycosylation sequences overlap such that the Asn residues are adjacent; and (b) expressing the polynucleotide in a host cell capable of attaching a carbohydrate moiety at the Asn residues, and (2) a polypeptide having increased glycosylation produced by the described process.

The invention also relates to (1) a method of producing a polypeptide having increased glycosylation, comprising: (a) providing to a polynucleotide encoding the polypeptide at least two tripeptide Asn-linked glycosylation sequences, wherein each tripeptide glycosylation sequence comprises Asn-Xaa-Yaa, wherein Xaa is an amino acid other than proline and Yaa is threonine or serine, and wherein the tripeptide glycosylation sequences are in tandem such that the Asn residues are separated by two amino acid residues; (b) providing to the polynucleotide at least one set of two tripeptide Asn-linked glycosylation sequences, wherein the two tripeptide glycosylation sequences overlap such that the Asn residues are adjacent; and (c) expressing the polynucleotide in a host cell capable of attaching a carbohydrate moiety at the Asn residues, and (2) a polypeptide having increased glycosylation produced by the described process.

BRIEF DESCRIPTION OF THE FIGURES

FIGS. 1A and 1B. DNA sequence (SEQ ID NO: 1) and translated protein sequence (SEQ ID NO: 2) of CC49/218 SCA are shown on two sheets (FIGS. 1A and 1B), with engineered N-linked glycosylation sites indicated. The variable light ($V_L$) and variable heavy ($V_H$) chains are indicated. Restriction sites are underlined and named. CDR sequences are double underlined. The 218 linker is underlined and named. Proposed tripeptide N-linked glycosylation sites are underlined. The mutations made to generate the N-linked glycosylation sites are shown in parenthesis underneath the proposed glycosylation sites and the site of oligosaccharide attachment is denoted under the mutated sequence by * and numbered. The C-terminal extension for glycosylation is shown in parenthesis.

FIGS. 5A and 5B(a–c). Lectin specific separation of glyco-SCA from unmodified SCA by Con A Sepharose. CC49/218 SCA from EN235 culture supernatant was incubated with molar excess of Con A Sepharose resin (Pharmacia Biotech). The unbound supernatant fraction was removed, and the bound fraction was eluted with alpha-D-methylmannoside. SDS-PAGE analysis was performed on 4–20% slab gels (~1 µg per lane). The Coomassie Blue stained gel is shown in FIG. 5A: Lane a, bound fraction; Lane b, unbound fraction; Lane c, untreated culture supernatant. The gel was scanned as in FIGS. 4A and 4B and the results are shown in FIG. 5B(a–c), where peaks 1 and 2 correspond to bands 1 and 2, respectively.

FIG. 6. Kabat consensus $V_K$ I/218/$V_H$III SCA with engineered glycosylation sites. Amino acid sequence (SEQ ID NO: 3) and engineered N-linked glycosylation sites for a consensus human SCA protein containing a $V_L$ domain (derived from a human kappa light chain subgroup I consensus sequence) and a $V_H$ domain (derived from a human heavy chain subgroup III consensus sequence) which are tethered by the 218-linker. Amino acid assignments are according to Kabat et al., *Sequences of Proteins of Immunological Interest*, pp. 108 & 331, 5th ed., U.S. Dept. Health and Human Services, Bethesda, Md. (1991), where the assigned amino acid residue at a position is the most commonly occurring amino acid at that position. The amino acids are listed according to the standard one letter codon and X denotes any amino acid. CDR sequences are double underlined. The 218 linker is overlined and named. Proposed tripeptide N-linked glycosylation sites are underlined and the site of oligosaccharide attachment is indicated by *. Proposed residue(s) change to generate N-linked glycosylation site is in parenthesis below. The C-terminal extension for glycosylation is shown in parenthesis. The three uncommon $V_K$ I CDR1 positions 27D, 27E, and 27F are not shown. The $V_H$ III terminal position 113 is optional and alternate SCA may terminate at position 112. Proline residues flanking the tripeptide sequence in the ±3 position are changed to alanines, as recommended by the compilation of Gavel, Y., and von Heijne, G., *Protein Engng.* 3:433–442 (1990).

FIG. 7. C6.5/218 SCA with engineered glycosylation sites. Amino acid sequence (SEQ ID NO: 4) and engineered N-linked glycosylation sites for the human C6.5 SCA protein containing a $V_L$ domain (derived from a human lambda chain subgroup 1 segment) and a $V_H$ domain (derived from a human heavy chain subgroup 5 segment) which are tethered by the 21 8-linker. Amino acid assignments of the wild-type C6.5 variable domains are according to Schier, R., et al., *J. Mol. Biol.* 255:28–43 (1996). CDR sequences are double underlined. The 218 linker is overlined and named. Proposed tripeptide N-linked glycosylation sites are underlined and the site of oligosaccharide attachment is indicated by *. Proposed residue(s) change to generate N-linked glycosylation site is in parenthesis below. The C-terminal extension for glycosylation is shown in parenthesis. The $V_H$ terminal position 113 is optional and an alternate SCA may terminate at position 112. Proline residues flanking the tripeptide sequence in the +3 position are changed to alanines, as recommended by the compilation of Gavel, Y., and von Heijne, G., *Protein Engng.* 3:433–442 (1990).

FIG. 8. A33/218 SCA with engineered glycosylation sites. Amino acid sequence (SEQ ID NO:5) and engineered N-linked glycosylation sites for the murine A33 SCA protein of pGX9451 containing a mouse $V_L$ domain and a mouse $V_H$ domain which are tethered by the 218-linker. Amino acid assignments conform to the numbering system of Kabat et al., *Sequences of Proteins of Immunological Interest*, 5th ed., U.S. Dept. Health and Human Services, Bethesda, Md. (1991). CDR sequences are double underlined. The 218 linker is overlined and named. Proposed tripeptide N-linked glycosylation sites are underlined and the site of oligosaccharide attachment is indicated by *. Proposed residue(s) change to generate N-linked glycosylation site is in parenthesis below. The C-terminal extension for glycosylation is shown in parenthesis.

FIG. 11A. SEC chromatography of glycosylated and PEG-modified CC49 with two tandem glycosylation sites. The glyco-CC49/2 (EN279) was purified by a combination of cation exchange chromatography and anion exchange chromatography. Conditions for PEGylation (PEG modification) of the glycosylated CC49/2 were as described in Example 4. SEC chromatography of the reaction mixture showed the appearance of high molecular weight peaks in addition to the low molecular weight non-glycosylated peak which was the only peak before PEGylation. FIG. 11B. SDS-PAGE analysis of the reaction mixture showed that the glycosylated and PEGylated CC49/2 was all converted to a higher molecular weight species (lane 2). Lanes 2 and 3 contained a 50/50 mixture of glycosylated and non-glycosylated CC49 which was not PEG hydrazide modified. The non-glycosylated CC49/2 (Lane 3) remained at the position corresponding to the un-modified species. This indicated that the reaction was specific for the carbohydrate moiety and did not affect the SCA that contains no carbohydrate. Lanes 1 and 4 contained molecular weight standards.

DETAILED DESCRIPTION OF THE PREFERRED EMBODIMENTS

Figure 2A:
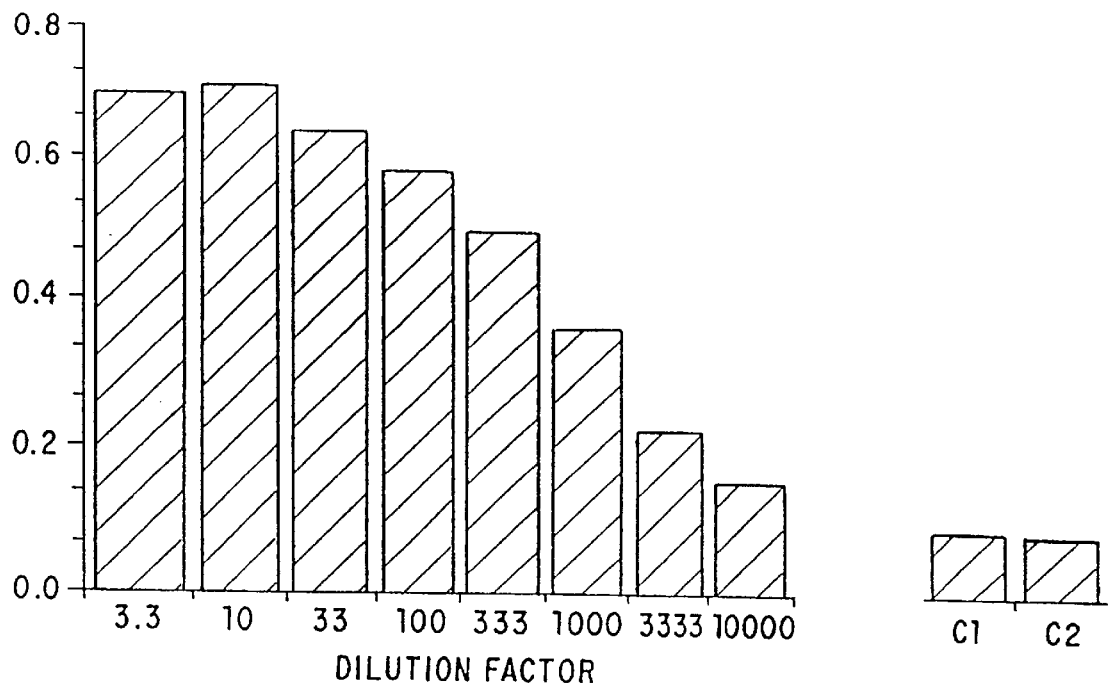
FIGS. 2A and 2B. Binding of serial dilutions of parent CC49/218 SCA obtained from E. coli GX9251 (FIG. 2A) or P. pastoris EN225 (FIG. 2B) to immobilized bovine submaxillary mucin in ELISA. The purified CC49/218 SCA from E. coli (100 µg/ml) and the unpurified culture supernatant from P. pastoris EN225 (~50 µg/ml SCA) were assayed for direct binding of antigen as described in Materials and Methods. Absorbance at 405 nm (A405) was measured after 10 mm of PNPP substrate incubation with the alkaline phosphatase conjugated rabbit anti-mouse antibody. Two controls are shown at the right. C1 records the absorbance of CC49/218 (3.3-fold dilution) assayed with immobilized porcine submaxillary mucin. C2 shows the background binding of induced *P. pastoris* host GS115 (3.3-fold dilution) to immobilized bovine submaxillary mucin.

The invention relates to the discovery that glycosylated single-chain antigen-binding molecules ("SCA") or single-chain variable fragments of antibodies ("sFv") have significant utility beyond that of the nonglycosylated single-chain antigen-binding proteins. In addition to maintaining an antigen binding site, a glycosylated SCA protein has a carbohydrate moiety which acts as a second biological effector. The oligosaccharide functions may include cellular and tissue targeting, specific binding and interactions with serum proteins, specific binding and interactions with cell receptors, cell matrix and intracellular proteins. Accordingly, the invention is directed to monovalent and multivalent SCA proteins capable of glycosylation, compositions of monovalent and multivalent glycosylated SCA proteins, methods of making and purifying monovalent and multivalent glycosylated SCA proteins, and uses for glycosylated SCA proteins. The invention is also directed to glycosylated SCA proteins having a diagnostic or therapeutic agent covalently attached to an Asn-linked carbohydrate moiety.

The terms "single-chain antigen-binding molecule" (SCA) or "single-chain Fv" (sFv) are used interchangeably here. They are structurally defined as comprising the binding portion of a first polypeptide from the variable region of an antibody $V_L$ (or $V_H$), associated with the binding portion of a second polypeptide from the variable region of an antibody $V_H$ (or $V_L$), the two polypeptides being joined by a peptide linker linking the first and second polypeptides into a single polypeptide chain, such that the first polypeptide is N-terminal to the linker and second polypeptide is C-terminal to the first polypeptide and linker. The single polypeptide chain thus comprises a pair of variable regions connected by a polypeptide linker. The regions may associate to form a functional antigen-binding site, as in the case wherein the regions comprise a light-chain and a heavy-chain variable region pair with appropriately paired complementarity determining regions (CDRs). In this case, the single-chain protein is referred to as a "single-chain antigen-binding protein" or "single-chain antigen-binding molecule."

Single-chain Fvs can and have been constructed in several ways. Either $V_L$ is the N-terminal domain followed by the linker and $V_H$ (a $V_L$-Linker-$V_H$ construction) or $V_H$ is the N-terminal domain followed by the linker and $V_L$ ($V_H$-Linker-$V_L$ construction). The preferred embodiment contains $V_L$ in the N-terminal domain (see, Anand, N. N., et al., *J. Biol. Chem.* 266:21874–21879 (1991)). Alternatively, multiple linkers have also been used. Several types of sFv proteins have been successfully constructed and purified, and have shown binding affinities and specificities similar to the antibodies from which they were derived.

A description of the theory and production of single-chain antigen-binding proteins is found in Ladner et al., U.S. Pat. Nos. 4,946,778, 5,260,203, 5,455,030 and 5,518,889, and in Huston et al., U.S. Pat. No. 5,091,513 ("biosynthetic antibody binding sites" (BABS)), which disclosures are all incorporated herein by reference. The single-chain antigen-binding proteins produced under the process recited in the above patents have binding specificity and affinity substantially similar to that of the corresponding Fab fragment.

Typically, the Fv domains have been selected from the group of monoclonal antibodies known by their abbreviations in the literature as 26–10, MOPC 315, 741F8, 520C9, McPC 603, D1.3, murine phOx, human phOx, RFL3.8 sTCR, 1A6, Sel55-4, 18-2-3, 4-4-20, 7A4-1, B6.2, CC49, 3, C2, 2c, MA-15C5/$K_{12}G_0$, Ox, etc. (see, Huston, J. S. et al., *Proc. Natl. Acad. Sci. USA* 85:5879–5883 (1988); Huston, J. S. et al., *SIM News* 38(4) (Supp.):1 (1988); McCartney, J. et al., *ICSU Short Reports* 10:114 (1990); McCartney, J. E. et al., unpublished results (1990); Nedelman, M. A. et al., *J. Nuclear Med.* 32 (Supp.):1005 (1991); Huston, J. S. et al., In: *Molecular Design and Modeling: Concepts and Applications, Part B*, edited by J. J. Langone, *Methods in Enzymology* 203:46–88 (1991); Huston, J. S. et al., In: *Advances in the Applications of Monoclonal Antibodies in Clinical Oncology*, Epenetos, A. A. (Ed.), London, Chapman & Hall (1993); Bird, R. E. et al., *Science* 242:423–426 (1988); Bedzyk, W. D. et al., *J. Biol. Chem.* 265:18615–18620 (1990); Colcher, D. et al., *J. Nat. Cancer Inst.* 82:1191–1197 (1990); Gibbs, R. A. et al., *Proc. Natl. Acad. Sci. USA* 88:4001–4004 (1991); Milenic, D. E. et al., *Cancer Research* 51:6363–6371 (1991); Pantoliano, M. W. et al., *Biochemistry* 30:10117–10125 (1991); Chaudhary, V. K. et al., *Nature* 339:394–397 (1989); Chaudhary, V. K. et al., *Proc. Natl. Acad. Sci. USA* 87:1066–1070 (1990); Batra, J. K. et al., *Biochem. Biophys. Res. Comm.* 171:1–6 (1990); Batra, J. K. et al., *J. Biol. Chem.* 265:15198–15202 (1990); Chaudhary, V. K. et al., *Proc. Natl. Acad. Sci. USA* 87:9491–9494 (1990); Batra, J. K. et al., *Mol. Cell. Biol.* 11:2200–2205 (1991); Brinkmann, U. et al, *Proc. Natl. Acad. Sci. USA* 88:8616–8620 (1991); Seetharam, S. et al., *J. Biol. Chem.* 266:17376–17381 (1991); Brinkmann, U. et al., *Proc. Natl. Acad. Sci. USA* 89:3075–3079 (1992); Glockshuber, R. et al., *Biochemistry* 29:1362–1367 (1990); Skerra, A. et al., *Bio/Technol.* 9:273–278 (1991); Pack, P. et al., *Biochemistry* 31:1579–1534 (1992); Clackson, T. et al., *Nature* 352:624–628 (1991); Marks, J. D. et al., *J. Mol. Biol.* 222:581–597 (1991); Iverson, B. L. et al., *Science* 249:659–662 (1990); Roberts, V. A. et al., *Proc. Natl. Acad. Sci. USA* 87:6654–6658 (1990); Condra, J. H. et al., *J. Biol. Chem.* 265:2292–2295 (1990); Laroche, Y. et al., *J. Biol. Chem.* 266:16343–16349 (1991); Holvoet, P. et al., *J. Biol. Chem.* 266:19717–19724 (1991); Anand, N. N. et al., *J. Biol. Chem.* 266:21874–21879 (1991); Fuchs, P. et al., *Bio/Technol.* 9:1369–1372 (1991); Breitling, F. et al., *Gene* 104:104–153 (1991); Seehaus, T. et al., *Gene* 114:235–237 (1992); Takkinen, K. et al., *Protein Engng.* 4:837–841 (1991); Dreher, M. L. et al., *J. Immunol. Methods* 139:197–205 (1991); Mottez, E. et al., *Eur. J. Immunol.* 21:467–471 (1991); Traunecker, A. et al., *Proc. Natl. Acad. Sci. USA* 88:8646–8650 (1991); Traunecker, A. et al., *EMBO J.* 10:3655–3659 (1991); Hoo, W. F. S. et al., *Proc. Natl. Acad. Sci. USA* 89:4759–4763 (1993)).

Linkers of the invention used to construct SCA polypeptides are designed to span the C-terminus of $V_L$ (or neighboring site thereof) and the N-terminus of $V_H$ (or neighboring site thereof) or between the C-terminus of $V_H$ and the N-terminus of $V_l$. The preferred length of the peptide linker should be from 2 to about 50 amino acids. In each particular case, the preferred length will depend upon the nature of the polypeptides to be linked and the desired activity of the linked fusion polypeptide resulting from the linkage. Generally, the linker should be long enough to allow the resulting linked fusion polypeptide to properly fold into a conformation providing the desired biological activity. Where conformational information is available, as is the case with SCA polypeptides discussed below, the appropriate linker length may be estimated by consideration of the 3-dimensional conformation of the substituent polypeptides and the desired conformation of the resulting linked fusion polypeptide. Where such information is not available, the appropriate linker length may be empirically determined by testing a series of linked fusion polypeptides with linkers of varying lengths for the desired biological activity. Such linkers are described in detail in WO 94/12520, which disclosure is incorporated herein by reference.

Preferred linkers used to construct SCA polypeptides have between 10 and 30 amino acid residues. The linkers are designed to be flexible, and it is recommended that an underlying sequence of alternating Gly and Ser residues be used. To enhance the solubility of the linker and its associated single chain Fv protein, three charged residues may be included, two positively charged lysine residues (K) and one negatively charged glutamic acid residue (E). Preferably, one of the lysine residues is placed close to the N-terminus of $V_H$, to replace the positive charge lost when forming the peptide bond of the linker and the $V_H$.

In addition, it has been found that linker lengths of equal to or greater than 18 residues reduce aggregation. This becomes important at high concentrations, when aggregation tends to become evident. Thus, linkers having 18 to 30 residues are most preferred for SCA polypeptides in the monovalent conformation. Linker lengths of less than 10 residues are favored for SCA in the multimer conformation.

Another property that is important in engineering an SCA polypeptide, or any other linked fusion polypeptide, is proteolytic stability. The 212 linker (Pantoliano et al., *Biochemistry* 30:10117 (1991)) is susceptible to proteolysis by subtilisin BPN'. The proteolytic clip in the 212 linker occurs between Lys8 and Ser9 of the linker (see Table 1). By placing a proline at the proteolytic clip site one may be able to protect the linker.

Table 1 shows various linkers for illustration. See also, Whitlow, M., et al., *Protein Engng.* 7:1017–1026 (1994). The 217 linker contains a lysine-proline pair at positions 6 and 7; the 218 linker contains the lysine-proline pair at positions 8 and 9, respectively, thus rendering the linker less susceptible to proteolysis. The 218 linker demonstrates less aggregation, greater proteolytic stability, and the necessary flexibility and solubility to result in a functional linker for SCA proteins.

TABLE 1

Linker Designs

| Linker | Linker Name | Reference |
|---|---|---|
| GKSSGSGSESKS[3] | 202' | Bird et al.[1] |
| GSTSGSGKSSEGKG[4] | 212 | Bedzyk et al.[2] |
| GSTSGSGKSSEGSGSTKG[5] | 216 | 212 Experimental Derivative |
| GSTSGKPSEGKG[6] | 217 | WO 94/12520 |
| GSTSGSGKPGSGEGSTKG[7] | 218 | WO 94/12520 |

[1] Science 242:423 (1988)
[2] J. Biol. Chem. 265:18615–18620 (1990)
[3] SEQ. ID NO. 6
[4] SEQ. ID NO. 7
[5] SEQ. ID NO. 8
[6] SEQ. ID NO. 9
[7] SEQ. ID NO. 10

A second guiding consideration in linker design is that a linker with reduced aggregation is preferable. As described above, the 18-residue 216 linker shows reduced aggregation as compared to the 14-residue 212 linker. The first eleven residues of the 216 linker are identical to the 212 linker, including the proteolytically-susceptible peptide bond between Lys8 and Ser9. Thus, it is believed that the extra four residues contribute to the lowered aggregation. Linkers with 18 or more residues are thus most preferred.

Taking the above into consideration, a linker was designed in which a proline was substituted for serine at position 9, after Lys8, in the 18-residue 216 linker. The linker is designated 218 (see Table 1). See WO 94/12520, which disclosure is incorporated herein by reference.

Positioning the proline at the proper place in the linker sequence to inhibit proteolysis is accomplished by determining the points of proteolytic attack in the susceptible sequence. One of ordinary skill in the art will know of methods of determining this point. In one method, a protease such as subtilisin BPN' is contacted with the candidate linker. Cleavage can then be determined by sequencing the resulting peptides, which will also reveal the cleavage point or points, if any. Any protease may be used, and selection will be guided by consideration of the environment the linker is to encounter in actual use.

The requirements for an SCA is that the linker be longer than 12 amino acids. The preferred length of the linker in an SCA is greater than 18 residues, in order to reduce aggregation, as described above.

For multivalent SCAs, the association of two or more SCAs is required for their formation. Although, multivalent SCAs can be produced from SCAs with linkers as long as 25 residues, they tend to be unstable. Holliger, P., et al., *Proc. Natl. Acad. Sci. USA* 90:6444–6448 (1993), have recently demonstrated that linkers 0 to 15 residues in length facilitate the formation of divalent Fvs. See, Whitlow, M., et al., *Protein Engng.* 7:1017–1026 (1994); Hoogenboom, H. R., *Nature Biotech.* 15:125–126 (1997); and WO 93/11161.

The object of the present invention is to produce an SCA having one or more (or at least one) Asn-linked glycosylation sequence(s) such that the Asn-linked glycosylation site (the asparagine residue within the glycosylation sequence) is capable of attaching a carbohydrate moiety and the glycosylated polypeptide is capable of binding an antigen (i.e., the glycosylated polypeptide's ability to bind an antigen is not disrupted). For example, the SCA may have one, two, three, five, seven or ten N-linked glycosylation sequence(s), but not limited to the numbers recited. Asn-linked glycosylation, also referred to as N-linked glycosylation, occurs when sugar residues are linked through the amide nitrogen of asparagine residues. Intracellular biosynthesis of Asn-linked oligosaccharides occurs in both the lumen of the endoplasmic reticulum and following transport of the protein to the Golgi apparatus. Asn-linked glycosylation occurs at the following tripeptide glycosylation consensus sequence: Asn-Xaa-Yaa (Asn-Xaa-Thr/Ser; NXT/S), where Xaa may be any amino acid except proline and Yaa is serine or threonine.

All Asn-linked oligosaccharides have a common pentasaccharide core ($Man_3GlcNAc_2$) originating from a common biosynthetic intermediate. They differ in the number of branches and the presence of peripheral sugars such as fucose and sialic acid. They can be categorized according to their branched constituents, which may consist of mannose only (high mannose N-glycans); alternating GlcNAc and Gal residues terminated by various sugar sequences, and with the possibility of intrachain substitutions of bisecting Fuc and core GlcNAc (complex N-glycans); or attributes of both high mannose and complex chains (hybrid N-glycans). See, Hounsell, E. F ed., "Glycoprotein Analysis in Biomedicine," *Methods in Molecular Biology* 14:298 (1993).

A further object of the invention is to produce monovalent and multivalent SCAs having one or more Asn-linked glycosylation sequence(s). For multivalent SCAs, the association of two or more SCAs is required for their formation. For example, multivalent SCAs may be generated by chemically crosslinking two SCAs with C-terminal cysteine residues (Cumber et al., *J. Immunol.* 149:120–126 (1992)) and by linking two SCAs with a third polypeptide linker to form a dimeric Fv (George et al., *J. Cell. Biochem.* 15E:127 (1991)). Details for producing multivalent SCAs by aggregation are described in Whitlow, M., et al., *Protein Engng.* 7:1017–1026 (1994). Multivalent antigen-binding fusion proteins of the invention can be made by any process, but preferably according to the process for making multivalent antigen-binding proteins set forth in WO 93/11161, which disclosure is incorporated herein by reference.

Yet a further object of the invention is to produce monovalent or multivalent SCAs, as described above, having at least two tripeptide glycosylation sequences in tandem such that the Asn residues are separated by two amino acid residues. Another object of the invention is to produce monovalent or multivalent SCAs, as described above, having at least one set of two overlapping tripeptide glycosylation sequences such that the Asn residues are adjacent. Another object of the invention is to produce monovalent or multivalent glycosylated SCAs, as described above, which are conjugated to polyalkylene oxide.

Identification and Synthesis of N-linked Glycosylation Sequences

In the present invention, N-linked glycosylation sites within the tripeptide glycosylation consensus sequences may occur in the $V_L$ and $V_H$ regions, the C-terminus of the second polypeptide ($V_L$, $V_H$ or neighboring site thereof), the N-terminus of the first polypeptide ($V_L$, $V_H$ or neighboring site thereof), the linker region between the first and second polypeptide regions, or occur in a combination of these regions. The design of the carbohydrates site on a protein involves examining the structural information known about the protein and the residues in the proteins involved in antigen binding. The carbohydrates sites are chosen to be as far from these residues as possible so as to prevent disruption of the antigen-binding site. See Hubbard, S. C., and Ivatt, R. J., *Ann. Rev. Biochem.* 50:555–583 (1981), for review of synthesis and processing of Asn-linked glycosylation.

The glycosylation sequence may occur adjacent to the (1) native C-terminus residue of $V_L$ (or $V_H$), (2) the C-terminus of $V_L$ (or $V_H$) wherein the C-terminus has a deletion of one or plurality of amino acid residue(s), such that the remaining N-terminus amino acid residues of the peptide are sufficient for the glycosylated polypeptide to be capable of binding an antigen, or (3) the C-terminus of $V_L$ (or $V_H$) wherein the C-terminus residue has an addition of one or plurality of amino acid residue(s), such that the glycosylated polypeptide is capable of binding an antigen. By "native" is intended the naturally occurring C-terminus of the immunoglobulin (second polypeptide). By "C-terminus, " it is well understood in the art as intending the C-terminus amino acid residue or the C-terminus region of a polypeptide, which could include up to all of the amino acid residues of the polypeptide excluding the first N-terminus amino acid residue of the polypeptide. However, in the present invention, "C-terminus" is intended as the C-terminus amino acid residue of the above-mentioned three types of C-terminus (1, 2 or 3), unless otherwise indicated or intended.

Glycosylation sequences were identified and engineered at residues within loop sites in regions of the SCA that are diametrically opposed to the antigen binding site. The five loop regions and C-terminal extension chosen as preferred sites of glycosylation are among the most distant regions spatially removed from the binding site.

The six furthest portions of an SCA from the antigen binding site are as follows:

1) The loop made up of residues 11 to 15 in the light chain;
2) The loop made up of residues 77 to 79 in the light chain;
3) The N-terminus of the linker;
4) The loop made up of residues 11 to 15 in the heavy chain;
5) The loop made up of residues 82B, 82C and 83 in the heavy chain; and
6) The C-terminus of the SCA.

The residues are identified as according to Kabat et al., *Sequences of Proteins of Immunological Interest*, 5th ed., U.S. Dept. Health and (1991). These possible glycosylation sites were determined by examining the 4-4-20 mouse Fab structure (see, Whitlow, M. et al., *Protein Engng.* 8:749–761 (1995), which disclosure is incorporated herein by reference).

After identifying the loops furthest from the antigen binding site, the nucleic and amino acid sequences of each loop are examined for possible N-linked glycosylation sequences which may be engineered into the loop region. The best sites are those in which it takes a minimum number of amino acid changes to generate the Asn-Xaa-Thr/Ser glycosylation sequence. (According to Gavel, Y., and von Heijne, G., *Protein Engng.* 3:433442 (1990), which disclosure is incorporated herein by reference, Thr occurs in successfully glycosylated tripeptide sequences about two times as often as Ser.) This can be performed manually or with a computer program using sequence homology rules, such as the "Gene Works" Program from Intelligenetics, Inc. (Mountain View, Calif.). However, the engineered placement of the N of the N-X-S/T sequence anywhere in these six identified regions can generate a preferred site for SCA glycosylation.

Figure 6:
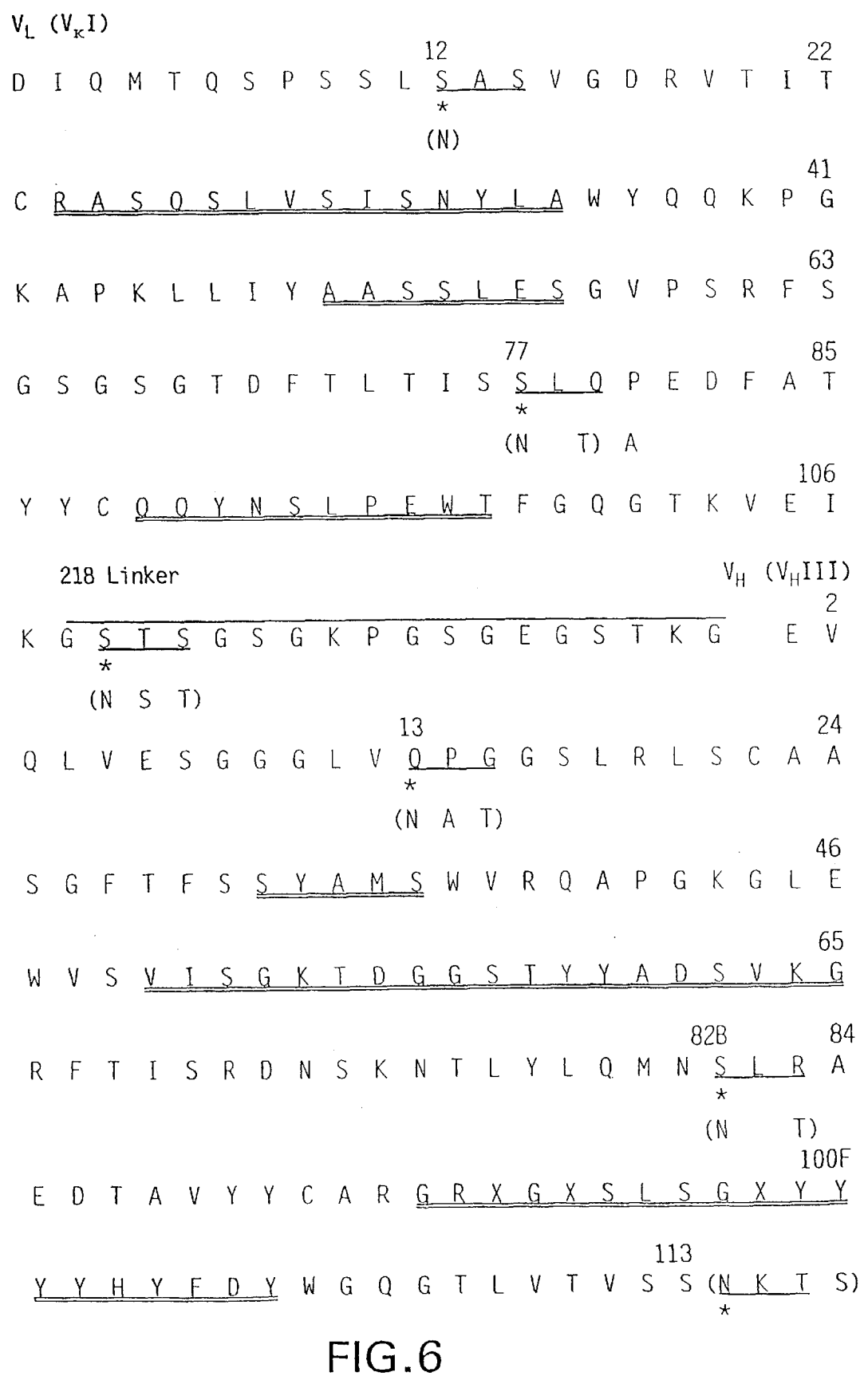
Figure 7:
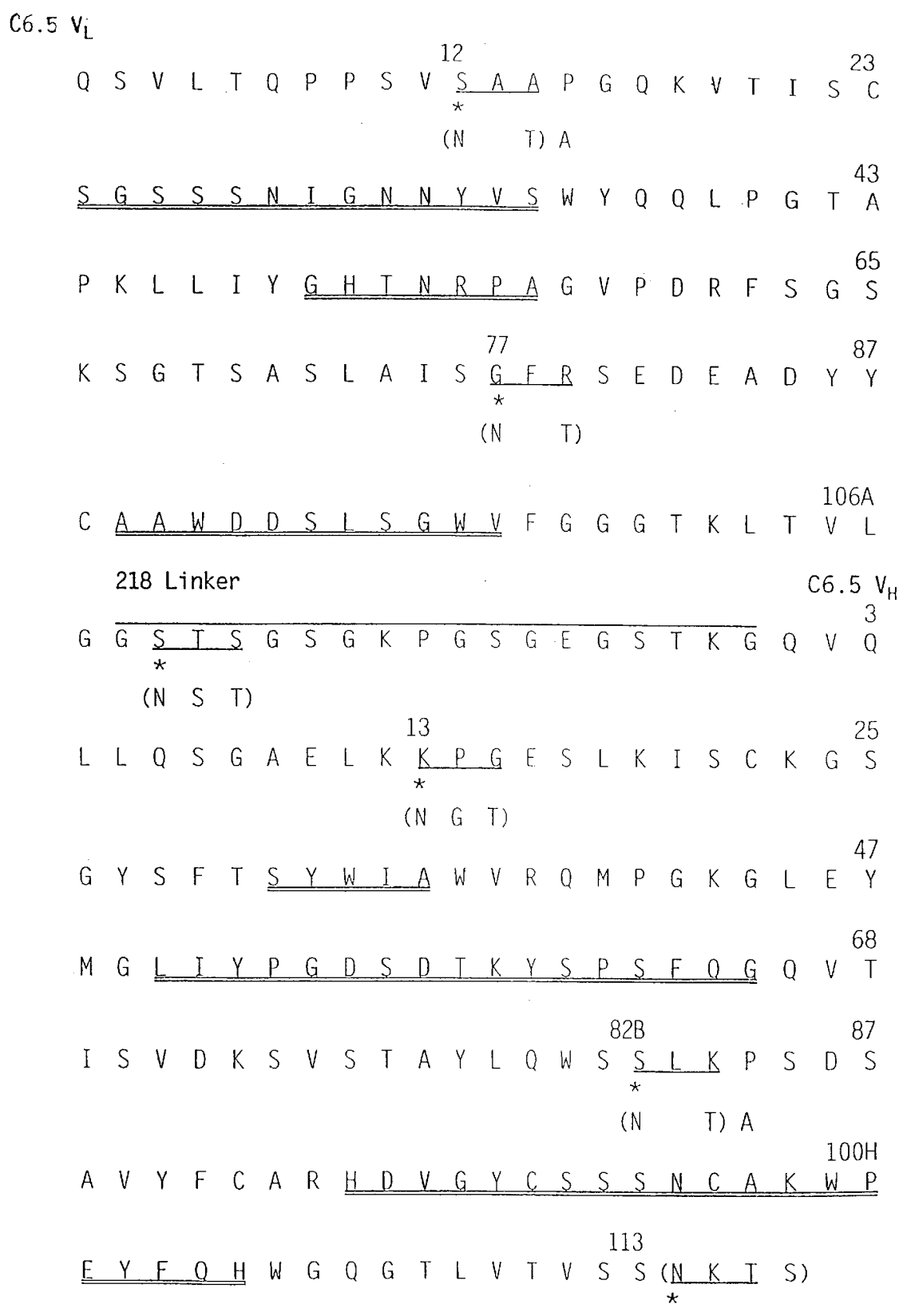

The design approach described above has been used for the CC49/2 18 SCA. FIGS. 1A and 1B show the following resulting designs: designed glycosylation sites no. 1 and no. 2 in the light chain of the CC49/218 SCA; designed glycosylation site no. 3 in the N-terminal end of the linker in CC49/218 SCA; designed glycosylation sites no. 4 and no. 5 in the heavy chain of the CC49/218 SCA; designed glycosylation site no. 6 adjacent to the C-terminus of the CC49/218 SCA. Any combination of these six sites could be used. The design approach can be used for other SCAs, such as a Kabat consensus $V_K$II21 8/$V_H$III, C6.5/218 and A33/218, as shown in FIGS. 6–8, respectively.

The particular nucleotide sequence which is used to introduce an Asn-linked glycosylation sequence into the various positions will depend upon the naturally-occurring nucleotide sequence. The most preferred sites are those in which it takes a minimum number of amino acid changes to generate the Asn-linked glycosylation sequence. For example, glycosylation sequence no. 1 in FIG. 1A was generated by mutating amino acid 12, Pro (CCT), to Asn (AAC), resulting in an Asn-linked glycosylation sequence of Asn-Val-Ser. Similarly, other Asn-linked sequences may be generated. Of course, based on the redundancy of the genetic code, a particular amino acid may be encoded by multiple nucleotide sequences.

in an expression system that is capable of glycosylating the protein, such as bacterial cells, yeast or other fungal cells, insect cells or mammalian cells. It may be important to find a system that uniformly glycosylates the mutant glycoprotein. The mutant glycoprotein can be purified by standard purification methods.

Oligonucleotide-directed mutagenesis methods for generating the Asn-linked glycosylation sequences and related techniques for mutagenesis of cloned DNA are well known in the art. See, Sambrook et al., MOLECULAR CLONING: A LABORATORY MANUAL, 2nd ed., Cold Spring Harbor Laboratory, Cold Spring Harbor, N.Y. (1989); Ausubel et al. (eds.), CURRENT PROTOCOLS IN MOLECULAR BIOLOGY, John Wiley and Sons (1987), each of which disclosure is incorporated herein by reference. A preferred oligonucleotide-directed mutagenesis method for the present invention is according to Ho et al., *Gene* 77:51–59 (1989), which disclosure is incorporated herein by reference. The primer sequences used for generating tandem and/or overlapping glycosylation sequences are disclosed in Example 1, Materials and Methods section, infra.

Synthesis of Multiple Tandem and Overlapping Glycosylation Sequences

A single chain antigen binding molecule (e.g., CC49) with the genetic sequence (polynucleotide) available for glycosylation can be made to contain the carbohydrate moiety by a post-translation process that is available in eukaryotic cells, such as in the yeast Pichia.

The gCC49 was derived from the original clone CC49/218 by incorporating glycosylation genetic sequences. Several clones were created.

Plasmid pEN270 was transformed into Pichia to give a clone EN279 that secretes glycosylated CC49-protein designated as gCC49/2. This clone contained two glycosylation sequences. The gene product produced by the yeast had over 50% of the total expressed single chain antigen binding molecule in the glycosylated form.

Plasmid pEN271 was transformed into Pichia to give a clone EN280 that secretes glycosylated CC49 protein designated as gCC49/3. This clone contained three glycosylation sequences. The gene product produced by the yeast had over 90% of the single chain antigen-binding protein in the glycosylated form.

CC49 having exemplary one, two or three glycosylation sequence(s) (in bold) adjacent to the C-terminus are provided below.

```
C-terminal of CC49 with one glycosylation sequence:

Ser Val Thr Val Ser Asn Lys Thr Ser Stop  BamHI              (SEQ ID NO:12)

TCA GTC ACC GTC TCC AAC AAG ACC AGT TAA TAG GAT CC           (SEQ ID NO:11)

C-terminal of CC49 with two glycosylation sequences:

Ser Val Thr Val Ser Asn Lys Thr Asn Ala Thr Ser Stop  BamHI  (SEQ ID NO:14)

TCA GTC ACC GTC TCC AAC AAG ACC AAT GCT ACC TCT TAA TAG GAT CC  (SEQ ID NO:13)

C-terminal of CC49 with three glycosylation sequences:

Ser Val Thr Val Ser Asn Lys Thr Asn Asn Thr Thr Ser Stop BamHI  (SEQ ID NO:16)

TCA GTC ACC GTC TCC AAC AAG ACC AAC AAT ACT ACC TCT TAA G GAT CC  (SEQ ID NO:15)
```

Site-directed mutagenesis is used to change the native protein sequence to one that incorporates the designed sites of N-linked glycosylation. The mutant protein gene is placed CC49 with one glycosylation sequence adjacent to the C-terminus includes the glycosylation sequence N-K-T (amino acids depicted in bold are those necessary for a glycosylation site). CC49 with two tandem glycosylation sequences adjacent to the C-terminus is also shown: N-K-T-N-A-T(SEQ ID NO: 17). Additionally, CC49 with three overlapping and tandem glycosylation sequences adjacent to the C-terminus is shown: N-K-T-N-N-T-T (SEQ ID NO: 18). Of course, the SCA may have two or more (or at least two), such as three, five, seven, or ten, for example, N-linked glycosylation sequences in tandem, or one or more (or at least one) set, such as three, five, seven, or ten, for example, sets of two tandem sequences. The SCA may have one or more (or at least one) set, such as two, three, five, seven or ten, for example, sets of two overlapping sequences.

The glycosylated CC49 was purified by a combination of cation exchange chromatography and anion exchange chromatography. The protein fraction that contains no carbohydrate was removed by size exclusion chromatography.

Other proteins may also be modified by the addition of tandem or overlapping glycosylation sequences. Such proteins include, but are not limited to, disulfide-stabilized Fv fragments (Reiter, Y. et al., *Nature Biotech.* 14:1239–1245 (1996)), camel immunoglobulins (Muyldermans, S. et al., *Protein Engng.* 7:1129–1135 (1994)), cancer vaccines, cell adhesion proteins such as selectin, members of the immunoglobulin superfamily including IgG, IgM, IgE, IgD and IgA as well as other immunoglobulin family proteins. Included also are therapeutic enzymes such as DNase, RNase, and catabolic enzymes, cytokines, hormones, and growth factors such as erythropoietin, GCSF (Granulocyte colony stimulating factor), GMCSF (Granulocyte macrophage colony stimulating factor). Also included are interleukin-2, alpha-interferon, insulin, human growth hormone, and other blood proteins such as tissue plasminogen activator and Factor VIII and Factor XI. In addition, these methods may be applied to vaccines such as hepatitis B vaccine, AIDS vaccines, lyme disease vaccines, and other infectious disease vaccines. Use of this technology also includes the selective N-linked modification of gene therapy vectors including viral vectors, non-viral vectors, and cellular vectors which contain such engineered N-linked glycoproteins.

It is surprising that SCA containing multiple tandem and/or overlapping glycosylation sequences are more completely glycosylated than an SCA containing a single glycosylation sequence as carbohydrate attachment at Asn residues near or adjacent to each other would be expected to encounter steric hindrance. Specifically, the two-sequence version was greater than 50% modified and the three-sequence version was greater than 95% modified compared to the single-site version which was about 35–50% modified. Moreover, in the triple sequence version, it is apparent that longer oligosaccharide chains are present. Thus, the invention relates to (1) a method of producing a polypeptide having increased glycosylation, comprising: (a) providing to a polynucleotide encoding the polypeptide at least two tripeptide Asn-linked glycosylation sequences, wherein each tripeptide glycosylation sequence comprises Asn-Xaa-Yaa, wherein Xaa is an amino acid other than proline and Yaa is threonine or serine, and wherein the tripeptide glycosylation sequences are in tandem such that the Asn residues are separated by two amino acid residues; and (b) expressing the polynucleotide in a host cell capable of attaching a carbohydrate moiety at the Asn residues, and (2) a polypeptide having increased glycosylation produced by the described process.

The invention further relates to (1) a method of producing a polypeptide having increased glycosylation, comprising: (a) providing to a polynucleotide encoding the polypeptide at least one set of two tripeptide Asn-linked glycosylation sequences, wherein each tripeptide glycosylation sequence comprises Asn-Xaa-Yaa, wherein Xaa is an amino acid other than proline and Yaa is threonine or serine, and wherein the two tripeptide glycosylation sequences overlap such that the Asn residues are adjacent; and (b) expressing the polynucleotide in a host cell capable of attaching a carbohydrate moiety at the Asn residues, and (2) a polypeptide having increased glycosylation produced by the described process.

The invention also relates to (1) a method of producing a polypeptide having increased glycosylation, comprising: (a) providing to a polynucleotide encoding the polypeptide at least two tripeptide Asn-linked glycosylation sequences, wherein each tripeptide glycosylation sequence comprises Asn-Xaa-Yaa, wherein Xaa is an amino acid other than proline and Yaa is threonine or serine, and wherein the tripeptide glycosylation sequences are in tandem such that the Asn residues are separated by two amino acid residues; (b) providing to the polynucleotide at least one set of two tripeptide Asn-linked glycosylation sequences, wherein the two tripeptide glycosylation sequences overlap such that the Asn residues are adjacent; and (c) expressing the polynucleotide in a host cell capable of attaching a carbohydrate moiety at the Asn residues, and (2) a polypeptide having increased glycosylation produced by the described process.

Hosts and Vectors

By "polynucleotide," is intended DNA, RNA or a genetic sequence. After mutating the nucleotide sequence of the SCA, the mutated DNA can be inserted into a cloning vector for further analysis, such as for confirmation of the DNA sequence. To express the polypeptide encoded by the mutated DNA sequence, the DNA sequence is operably linked to regulatory sequences controlling transcriptional expression and introduced into either a prokaryotic or eukaryotic host cell.

Although SCAs are typically produced by prokaryotic host cells, eukaryotic host cells are the preferred host cells. Preferred host cells include plant cells, yeast or other fungal cells, insect cells or mammalian cells. Standard protein purification methods may be used to purify these mutant glycoproteins. Only minor modification to the native protein's purification scheme may be required.

Also provided by the invention are DNA molecules such as purified genetic sequences or plasmids or vectors encoding the SCA of the invention that have engineered sequences capable of N-linked glycosylation. The DNA sequence for the glycosylated SCA polypeptide can be chosen so as to optimize production in organisms such as plant cells, prokaryotes, yeast or other fungal cells, insect cells or mammalian cells.

The DNA molecule encoding an SCA having Asn-linked glycosylation sequences can be operably linked into an expression vector and introduced into a host cell to enable the expression of the glycosylated SCA protein by that cell. A DNA sequence encoding an SCA having Asn-linked glycosylation sequences may be recombined with vector DNA in accordance with conventional techniques.

Recombinant hosts as well as methods of using them to produce single chain proteins of the invention are also provided herein.

The expression of such SCA proteins of the invention can be accomplished in procaryotic cells. Preferred prokaryotic hosts include, but are not limited to, bacteria such as Neisseria, Mycobacteria, Streptococci, Chlamydia and *E. coli* which expresses recombinant heterologous enzymes capable of glycosylation.

Eukaryotic hosts for cloning and expression of such SCA proteins of the invention include insect cells, yeast, fungi, and mammalian cells (such as, for example, human or primate cells) either in vivo, or in tissue culture. A preferred host for the invention is *Pichia pastoris*.

The appropriate DNA molecules, hosts, methods of production, isolation and purification of monovalent, multivalent and fusion forms of proteins, especially SCA polypeptides, are thoroughly described in the prior art, such as, e.g., U.S. Pat. No. 4,946,778, which disclosure is incorporated herein by reference.

The SCA encoding sequence having Asn-linked glycosylation sequences and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the desired SCA protein may occur through the transient expression of the introduced sequence. Alternatively, permanent expression may occur through the integration of the introduced SCA sequence into the host chromosome.

In one embodiment, the SCA sequence can be integrated into the host cell chromosome. Cells which have stably integrated the introduced DNA into their chromosomes can be selected by also introducing one or more markers which allow for selection of host cells which contain the SCA sequence and marker. The marker may complement an auxotrophy in the host (such as his4, leu2, or ura3, which are common yeast auxotrophic markers), biocide resistance, e.g., antibiotics, or resistance to heavy metals, such as copper, or the like. The selectable marker gene can either be directly linked to the SCA DNA sequence to be expressed, or introduced into the same cell by co-transfection.

In another embodiment, the introduced sequence will be incorporated into a plasmid vector capable of autonomous replication in the recipient host cell. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Any of a series of yeast vector systems can be utilized. Examples of such expression vectors include the yeast 2-micron circle, the expression plasmids YEP13, YCP and YRP, etc., or their derivatives. Such plasmids are well known in the art (Botstein et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982)).

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or more markers which allow selection of host cells which contain the expression vector. The marker may provide for prototropy to an auxotrophic host, biocide resistance, e.g., antibiotics, or resistance to heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cell. Biol.* 3:280 (1983), and others.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Preferred vectors for expression in Pichia are pHIL-S 1 (Invitrogen Corp.) and pPIC9 (Invitrogen Corp.). Other suitable vectors will be readily apparent to the skilled artisan.

Once the vector or DNA sequence containing the constructs has been prepared for expression, the DNA constructs may be introduced or transformed into an appropriate host. Various techniques may be employed, such as transformation, transfection, protoplast fusion, calcium phosphate precipitation, electroporation, or other conventional techniques. After the cells have been transformed with the recombinant DNA (or RNA) molecule, the cells are grown in media and screened for appropriate activities. Expression of the sequence results in the production of the glycosylated SCA of the present invention.

In the alternative approach, N-linked glycosylation can be achieved in vitro by reacting the mutant SCA polypeptides described herein with purified N-linked glycosylation enzymes and further reacting such glycosylated SCA with other carbohydrate modifying enzymes.

Poly(alkylene)-Glycol Modification

The straight chain polyalkylene glycols employed in the practice of the present invention are of the structural formula (I)

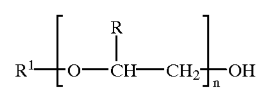

wherein R is selected from the group consisting of hydrogen, lower alkyl, and mixtures thereof, $R^1$ is selected from the group consisting of hydrogen and lower alkyl, and n is a positive integer. By "lower alkyl" is meant an alkyl group having from one to four carbon atoms, i.e., methyl, ethyl, propyl, butyl, and isomers of the foregoing. R is preferably selected from the group consisting of hydrogen, methyl, and mixtures thereof, $R^1$ is preferably selected from the group consisting of hydrogen and methyl, and n is preferably a positive integer of 500 or less. R is most preferably hydrogen, $R^1$ is most preferably methyl, and n is most preferably an integer of 7 to 150. It will be readily apparent to those skilled in the art that the preferred poly(alkylene glycols) employed in the practice of the present invention are poly(ethylene glycol), poly(propylene glycol), mixtures thereof, and copolymers of poly(ethylene glycol) and poly (propylene glycol), wherein one of the terminal hydroxyl groups of the polymer may be substituted with a lower alkyl group. A preferred polyalkylene glycol for use in the present invention is poly(ethylene glycol)-hydrazide.

For convenience, the polyalkylene glycol employed in the practice of the present invention will be designated PAG, which term is intended to include both compounds wherein $R^1$ is hydrogen and compounds wherein $R^1$ is alkyl. PEG refers to poly(ethylene glycol) and mPEG refers to methoxy poly(ethylene glycol).

The PAG does not have to be of a particular molecular weight, but it is preferred that the molecular weight be between about 500 and about 40,000; more preferably, between about 2,000 and about 20,000. The choice of molecular weight of PAG is made based on the nature of the particular polypeptide employed, for example, the number of amino or other groups available on the polypeptide for modification. Molecular weights of about 10,000 and about 20,000 are most preferred.

Zalipsky et al., *Eur. Pol. J.* 19(12):1177–1183 (1983), among others, have described the reaction of methoxy poly(ethylene glycol) with succinic anhydride:

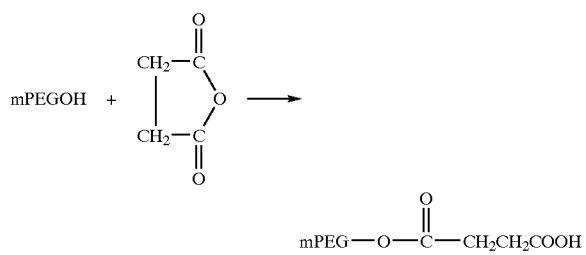

It is also known to alkylate mPEG with ethylbromoacetate in the presence of a base such as K-tertiary butoxide in tertiary butanol, Na-naphthalene in tetrahydrofuran, or butyl lithium in benzene:

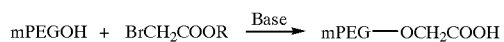

The terminal hydroxyl groups of PEG can be transformed into amine, carboxyl, or hexamethyl isocyanate groups. See, for example, Zalipsky et al., 1983, supra. A mixed anhydride derivative of carboxylated mPEG can be prepared in the presence of triethylamine and then reacted with proteins:

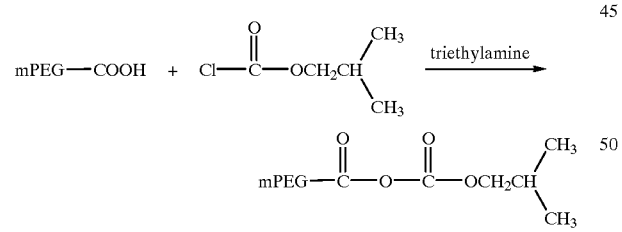

Carboxylated mPEG can also be reacted with hydroxysuccinimide in the presence of dicyclohexylcarbodiimide and dimethyl formamide for reaction with protein:

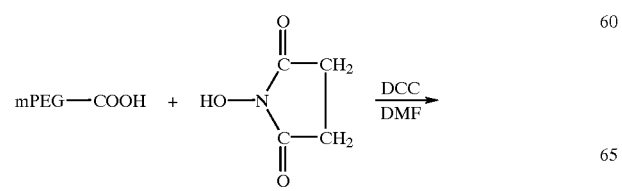

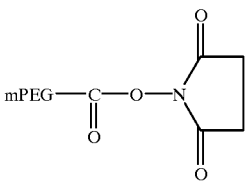

King and Weiner (*Int. J. Peptide Protein Res.* 16:147 (1980), describe the dithiocarbonate of mPEG:

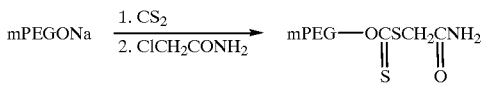

Beauchamp et al., *Analytical Biochem.* 131:25–33 (1983), describe the activation of PEG with 1,1'-carbonyldiimidazole. Reaction of this derivative with a peptide yields a carbamate linkage:

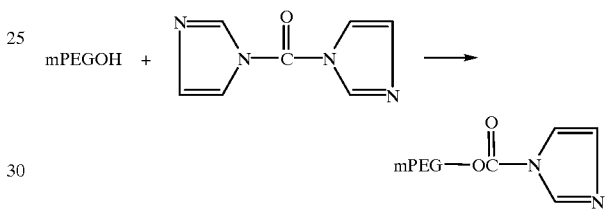

Veronese et al., *Appl. Biochem. & Biotechnol.* 11:141–152 (1985), describe the activation of methoxy poly(ethylene glycol) with phenylchloroformates, e.g., 2,4,5-trichlorophenylchloroformate or p-nitrophenylchloroformate. These derivatives are linked to peptides by urethane linkages:

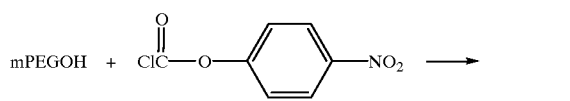

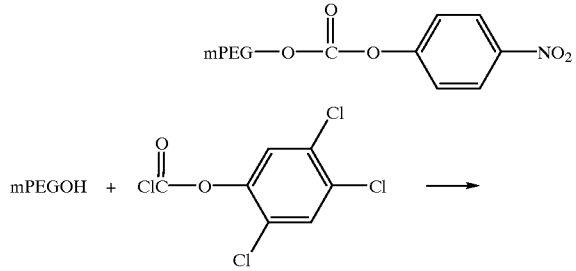

Ueno et al., European Patent Application 87103259.5, form mPEG imidoesters from the corresponding nitriles by reaction with dry hydrogen chloride in the presence of a dehydrated lower alcohol:

mPEGOH + BrCH₂CH₂CH₂CN ⟶ mPEGOCH₂CH₂CH₂CN
↓ CH₃OH, HCl
mPEGOCH₂CH₂CH₂C(=NH·HCl)OCH₃ mPEGOH + CH₂=CHCN —NaH→ mPEGOCH₂CH₂CN
↓ CH₃OH, HCl
mPEGOCH₂CH₂C(=NH·HCl)OCH₃

Abuchowski et al., *Cancer Biochem. Biophys.* 7:175–186 (1984), have described forming mPEG succinate as described above and then forming methoxy polyethylene glycolyl succinimidyl succinate ("SS-PEG") by reaction with hydroxysuccinimide in the presence of dicyclohexylcarbodiimide:

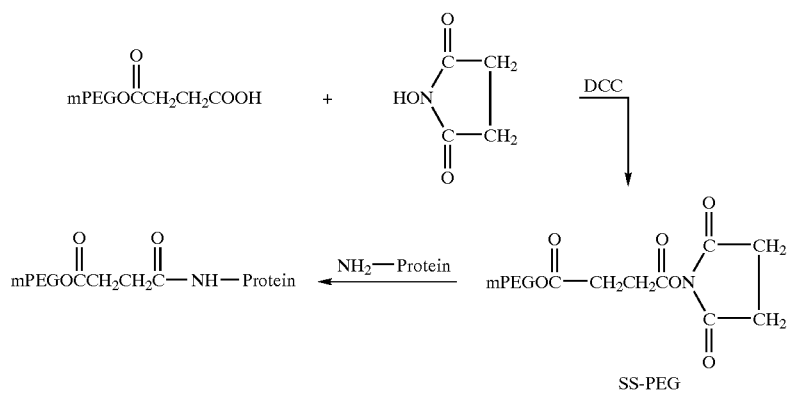

SS-PEG

Sano et al., European Patent Application No. 89107960.0, disclose the phenyl glyoxal derivative of methoxy poly (ethylene glycol), which is capable of modifying the guanidino groups in peptides:

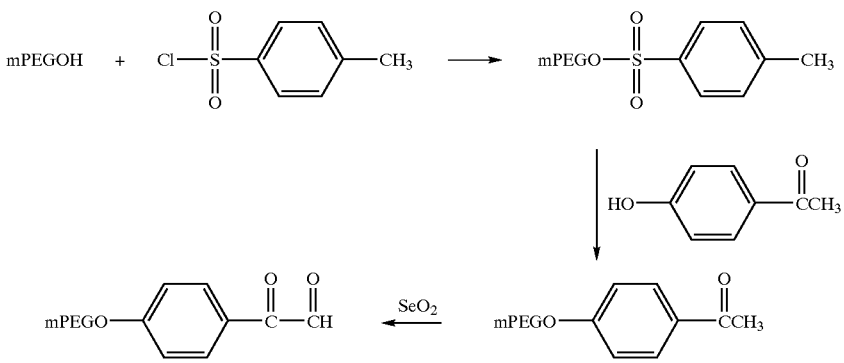

Zalipsky, in U.S. Pat. No. 5,122,614, describes the activation of PEG by conversion into its N-succinimide carbonate derivative ("SC-PEG"):

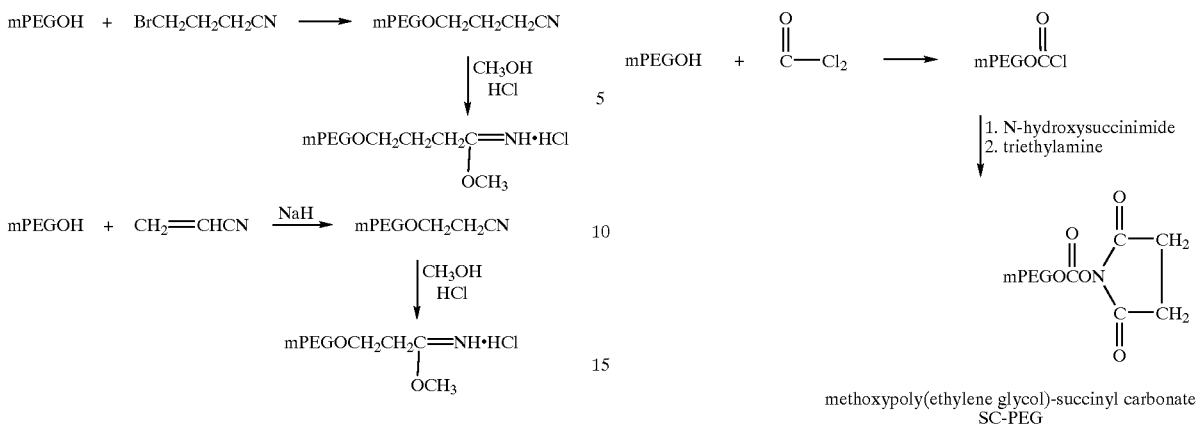

methoxypoly(ethylene glycol)-succinyl carbonate
SC-PEG

Zalipsky et al., *J. Macromol. Sci. Chem.* A21:839, disclose the amino acid ester derivative of methoxy poly (ethylene glycol):

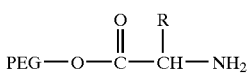

Davis et al., U.S. Pat. No. 4,179,337, disclose a hydrazide derivative of methoxy poly(ethylene glycol), which is capable of modifying aldehydes and ketones and other functional groups:

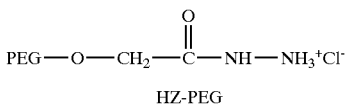

HZ-PEG

It is further disclosed that the bifunctional derivative of PEG, i.e., polyethylene glycol-bis-succinidyl carbonate ("BSC-PEG") can be prepared by similar means. The SC-PEG and BSC-PEG compounds are then reacted with amine groups in a protein and attached thereto via urethane (carbamate) linkages.

It will be readily apparent to those skilled in the art that other activated PAGs can also be employed in the practice of the present invention. The preferred activated PAG for use in the practice of the present invention is PEG-hydrazide.

Branched Polymers

The invention further provides for the use of branched, substantially non-antigenic polymers for PEGylation of the SCA proteins corresponding to the formula:

$$(R)_nL\text{—}A \tag{II}$$

wherein (R) includes a water-soluble non-antigenic polymer;

(n)=2 or 3;

(L) is an aliphatic linking moiety covalently linked to each (R); and (A) represents an activated functional group capable of undergoing nucleophilic substitution. For example, (A) can be a group which is capable of bonding with biologically active nucleophiles or moieties capable of doing the same.

In particularly preferred aspects of the invention (R) includes a poly(alkylene oxide) PAO such as poly(ethylene glycol) PEG or mPEG. It is preferred that each chain have a molecular weight of between about 200 and about 12,000 daltons and preferably between about 1,000 and about 10,000 daltons. Molecular weights of about 5,000 daltons are most preferred.

As shown in Formula II, 2 or 3 polymer chains, designated (R) herein, are joined to the aliphatic linking moiety (L). Suitable aliphatics included substituted alkyl diamines and triamines, lysine esters and malonic ester derivatives. The linking moieties are preferably non-planar, so that the polymer chains are not rigidly fixed. The linking moiety (L) is also a means for attaching the multiple polymer chains or "branches" to (A), the moiety through which the polymer attaches to the SCA protein.

(L) preferably includes a multiply-functionalized alkyl group containing up to 18, and more preferably between 1–10 carbon atoms. A heteroatom such as nitrogen, oxygen or sulfur may be included within the alkyl chain. The alkyl chain may also be branched at a carbon or nitrogen atom. In another aspect of the invention, (L) is a single nitrogen atom.

(L) and (R) are preferably joined by a reaction between nucleophilic functional groups on both (R) and (L). Each (R) is suitably functionalized to undergo nucleophilic substitution and bond with (L). Such functionalization of polymers is readily apparent to those of ordinary skill in the art.

A wide variety of linkages are contemplated between (R) and (L). Urethane (carbamate) linkages are preferred. The bond can be formed, for example, by reacting an amino group such as 1,3-diamino-2-propanol with methoxypolyethylene glycol succinimidyl carbonate as described in U.S. Pat. No. 5,122,614. Amide linkages, which can be formed by reacting an amino-terminated non-antigenic polymer such as methoxypolyethylene glycol-amine (mPEG amine) with an acyl chloride functional group. Examples of other such linkages include ether, amine, urea, and thio and thiol analogs thereof, as well as the thio and thiol analogs of the urethane and amide linkages discussed supra.

The moiety (A) of Formula II represents groups that "activate" the branched polymers of the present invention for conjugation with biologically active materials. (A) can be a moiety selected from:

1. Functional groups capable of reacting with an amino group such as:
   a) carbonates such as the p-nitrophenyl or succinimidyl;
   b) carbonyl imidazole;
   c) azlactones;
   d) cyclic imide thiones; or
   e) isocyanates or isothiocyanates.

2. Functional groups capable of reacting with carboxylic acid groups and reactive with carbonyl groups such as:
   a) primary amines; or
   b) hydrazine and hydrazide functional groups such as the acyl hydrazides, carbazates, semicarbamates, thiocarbazates, etc.

3. Functional groups capable of reacting with mercapto or sulfhydryl groups such as phenyl glyoxals; see, for example, U.S. Pat. No. 5,093,531.

4. Other nucleophiles capable of reacting with an electrophilic center. A non-limiting list includes, for example, hydroxyl, amino, carboxyl, thiol groups, active methylene and the like.

The moiety (A) can also include a spacer moiety located proximal to the aliphatic linking moiety (L). The spacer moiety may be a heteroalkyl, alkoxyl, alkyl containing up to 18 carbon atoms or even an additional polymer chain. The spacer moieties can be added using standard synthesis techniques.

The branched polymers, generally, U-PAO's or U-PEG's, are formed using conventional reaction techniques known to those of ordinary skill in the art.

These umbrella-like branched polymers of the present invention (U-PAO's or U-PEG's) react with biologically active nucleophiles to form conjugates. The point of polymer attachment depends upon the functional group (A). For example, (A) can be a succinimidyl succinate or carbonate and react with ε-amino lysines. The branched polymers can also be activated to link with any primary or secondary amino group, mercapto group, carboxylic acid group, reactive carbonyl group or the like found on biologically active polypeptides. Other groups are apparent to those of ordinary skill in the art.

One of the main advantages of the use of the branched polymers is that to the branching imparts an umbrella-like three dimensional protective covering to the materials they are conjugated with. This contrasts with the string-like structure of the straight chain polymers discussed, supra. An additional advantage of the branched polymers is that they provide the benefits associated with attaching several strands of polymers to a SCA protein or carbohydrate moiety but require substantially fewer conjugation sites. The desired properties of PEGylation are realized and the loss of bioactivity is minimized.

One or more of the activated branched polymers can be attached to a biologically active nucleophile, such as an SCA protein, by standard chemical reactions. The conjugate is represented by the formula:

$$[(R)_n L\!-\!A^1]_z\text{-(nucleophile)} \qquad (III)$$

wherein (R) is a water-soluble substantially non-antigenic polymer; n=2 or 3; (L) is an aliphatic linking moiety; ($A^1$) represents a linkage between (L) and the nucleophile and (z) is an integer $\geq 1$ representing the number of polymers conjugated to the biologically active nucleophile. The upper limit for (z) will be determined by the number of available nucleophilic attachment sites and the degree of polymer attachment sought by the artisan. The degree of conjugation can be modified by varying the reaction stoichiometry using well-known techniques. More than one polymer conjugated to the nucleophile can be obtained by reacting a stoichiometric excess of the activated polymer with the nucleophile.

Activated PAO can be attached to the carbohydrate moiety using the method generally described in Sea et al., *Immunoconjugates*, Vogel, C. Ed., Oxford University Press, p. 189 (1987), which disclosure is incorporated herein by reference. Briefly, the glycosylated SCA is oxidized with sodium periodate which provides an aldehyde group to which the PAO can bind. This reaction is stabilized by sodium borohydride. PAO attachment to polypeptides or glycopolypeptides is also described, for example, in Zalipsky, S, et al., WO 92/16555, which disclosure is incorporated herein by reference.

Conjugates

Upon production of the glycosylated SCA of the present invention, the glycosylated SCA may further be modified by conjugating a diagnostic or therapeutic agent to the carbohydrate moiety of the SCA. The general method of preparing an antibody conjugate according to the invention is described in Shih, L. B., et al., *Cancer Res.* 51:4192 (1991); Shih, L. B., and D. M. Goldenberg, *Cancer Immunol. Immunother.* 31:197 (1990); Shih, L. B., et al., *Intl. J. Cancer* 46:1101 (1990); Shih, L. B., et al., *Intl. J. Cancer* 41:832 (1988), which disclosures are all incorporated herein by reference. The indirect method involves reacting an antibody (or SCA), whose carbohydrate portion has been oxidized, with a carrier polymer loaded with one or plurality of peptide, lipid, nucleic acid, drug, toxin, chelator, boron addend or detectable label molecule(s).

Alternatively, the glycosylated SCA may be directly conjugated with a diagnostic or therapeutic agent. The general procedure is analogous to the indirect method of conjugation except that a diagnostic or therapeutic agent is directly attached to an oxidized sFv component. See Hansen et al., U.S. Pat. No. 5,443,953, which disclosure is incorporated herein by reference.

The glycosylated SCA can be attached to a derivative of the particular drug, toxin, chelator, boron addend or label to be loaded, in an activated form, preferably a carboxyl-activated derivative, prepared by conventional means, e.g., using dicyclohexylcarbodiimide (DCC) or a water soluble variant thereof, to form an intermediate adduct.

Many drugs and toxins are known which have a cytotoxic effect on tumor cells or microorganisms that may infect a human and cause a lesion, in addition to the specific illustrations given above. They are to be found in compendia of drugs and toxins, such as the Merck Index and the like. Any such drug can be loaded onto a carrier or directly onto a carbohydrate moiety of SCA by conventional means well known in the art, and illustrated by analogy to those described above.

Chelators for radiometals or magnetic resonance enhancers are also well known in the art. Typical are derivatives of ethylenediaminetetraacetic acid (EDTA) and diethylenetriaminepentaacetic acid (DTPA). These typically have groups on the side chain by which the chelator can be attached to a carrier or directly onto a carbohydrate moiety of SCA. Such groups include, e.g., a benzylisothiocyanate, by which the DTPA or EDTA can be coupled to the reactive group of an SCA.

Labels such as radioisotopes, enzymes, fluorescent compounds, electron transfer agents, and the like can also be linked to carrier or directly onto a carbohydrate moiety of SCA by conventional methods well known to the art. These labels and the SCA conjugates prepared from them can be used for immunoassays and for immunohistology, much as the SCA conjugate prepared by direct attachment of the labels to the SCA. However, the loading of the conjugates according to the present invention with a plurality of labels can increase the sensitivity of assays or histological procedures, where only low extent of binding of the SCA to target antigen is achieved.

Boron addends, e.g., carboranes, when attached to single-chain antigen binding molecules and targeted to lesions, can be activated by thermal neutron irradiation and converted to radioactive atoms which decay by alpha emission to produce highly cytotoxic short-range effects. High loading of boron addends, as well as of magnetic resonance enhancing ions, is of great importance in potentiating their effects. Carboranes can be made with carboxyl functions on pendant side chains, as is well known in the art.

Loading of drugs on the carrier will depend upon the potency of the drug, the efficiency of SCA targeting and the efficacy of the conjugate once it reaches its target. In most cases, it is desirable to load at least 20, preferably 50, and often 100 or more molecules of a drug on a carrier. The ability to partially or completely detoxify a drug as a conjugate according to the invention, while it is in circulation, can reduce systemic side effects of the drug and permit its use when systemic administration of the unconjugated drug would be unacceptable. Administration of more molecules of the drug, but conjugated to the SCA on a carrier, according to the present invention, permits therapy while mitigating systemic toxicity.

Toxins will often be less heavily loaded than drugs, but it will still be advantageous to load at least 5, preferably 10 and in some cases 20 or more molecules of toxin on a carrier and load at least one carrier chain on the SCA for targeted delivery.

The above-described conjugation of a diagnostic or therapeutic agent is also intended with glycosylated SCA further conjugated to polyalkylene oxide, at the carbohydrate and/or polymer moiety. Conjugation of poly(ethylene glycol) or poly(alkylene oxide) with small organic molecules is described in Greenwald, R. B., *Exp. Opin. Ther. Patents* 7:601–609 (1997), Enzon Inc., WO 95/11020, and Enzon Inc., WO 96/23794, which disclosures are all incorporated herein by reference. Compositions based on the use of various linker groups between the PEG ballast and the active drug are described in WO 96/23794.

Uses

One of the major utilities of the glycosylated SCA is its bifunctionality (or multifunctionality, including tri-, quadri-, etc.), in which one specificity is for one type of hapten or antigen, and the second specificity is for a second molecule or receptor. A glycosylated SCA molecule having two distinct binding specificities has many potential uses. For instance, the carbohydrate moiety may be specific for a cell-surface epitope of a target cell, such as a tumor cell or other undesirable cell. The antigen-binding site may be specific for a cell-surface epitope of an effector cell, such as the CD3 protein of a cytotoxic T-cell. In this way, the glycosylated SCA protein may guide a cytotoxic cell to a particular class of cells that are to be preferentially attacked. Alternatively, both targets, the antigen and the carbohydrate receptor can be on the same cell such that one target modulates binding specificity and the other target influences uptake or internalization.

Mannose-specific lectins are reported to be produced on the surface fimbria of enterobacterial species such as *E. coli*, Salmonella, and Pseudomonas. Such bacteria might be bound (extensively) to the oligosaccharides of glyco-SCA, while the SCA specificity is directed to an immune cell or otherwise promotes the microbe's clearance. Similarly, mannose specific receptors on tumor cells could have similar application. The bacterial lectins are also thought to be important in cell adhesion to host and infection suggesting another application.

Carbohydrate moieties on cell, viral or particle surfaces are major determinants of their identity. Using the SCA specificity to bind to the cell, viral or particle surfaces, and having the oligosaccharide moiety project out may give that entity a new identity for interaction with other cells, virus and proteins.

A diagnostic or therapeutic agent is a molecule or atom which is conjugated to an antibody and useful for diagnosis and for therapy. The immunoreactivity of the antibody is retained. Diagnostic or therapeutic agents include drugs, toxins, chelators, boron compounds and detectable labels. See "Conjugates" section, supra, for further details.

The diagnostic or therapeutic agent may be, but is not limited to, at least one selected from a nucleic acid, a compound, a protein, an element, a lipid, an antibody, a saccharide, an isotope, a carbohydrate, an imaging agent, a lipoprotein, a glycoprotein, an enzyme, a detectable probe, and antibody or fragment thereof, or any combination thereof, which may be detectably labeled as for labeling antibodies, as described herein. Such labels include, but are not limited to, enzymatic labels, radioisotope or radioactive compounds or elements, fluorescent compounds or metals, chemiluminescent compounds and bioluminescent compounds. Alternatively, any other known diagnostic or therapeutic agent can be used in a method of the present invention.

A therapeutic agent used in the present invention may have a therapeutic effect on the target cell, the effect selected from, but not limited to, correcting a defective gene or protein, a drug action, a toxic effect, a growth stimulating effect, a growth inhibiting effect, a metabolic effect, a catabolic affect, an anabolic effect, an antiviral effect, an antibacterial effect, a hormonal effect, a neurohumoral effect, a cell differentiation stimulatory effect, a cell differentiation inhibitory effect, a neuromodulatory effect, an antineoplastic effect, an anti-tumor effect, an insulin stimulating or inhibiting effect, a bone marrow stimulating effect, a pluripotent stem cell stimulating effect, an immune system stimulating effect, and any other known therapeutic effects that may be provided by a therapeutic agent delivered to a cell via a delivery system according to the present invention.

The SCA conjugate may be used for protection, suppression or treatment of infection or disease. By the term "protection" from infection or disease as used herein is intended "prevention," "suppression" or "treatment." "Prevention" involves administration of a glycosylated SCA conjugate prior to the induction of the disease. "Suppression" involves administration of the composition prior to the clinical appearance of the disease.

"Treatment" involves administration of the protective composition after the appearance of the disease. It will be understood that in human and veterinary medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis."

Such additional therapeutic agents which can further comprise a therapeutic agent or composition of the present invention may be selected from, but are not limited to, known and new compounds and compositions including antibiotics, steroids, cytotoxic agents, vasoactive drugs, antibodies and other therapeutic modalities. Non-limiting examples of such agents include antibiotics used in the treatment of bacterial shock, such as gentamycin, tobramycin, nafcillin, parenteral cephalosporins, etc; adrenal corticosteroids and analogs thereof, such as methyl prednisolone, mitigate the cellular injury caused by endotoxins; vasoactive drugs, such as alpha receptor blocking agent (e.g., phenoxybenzamine), beta receptor agonists (e.g., isoproterenol), and dopamine are agents suitable for treating septic shock.

Glycosylated SCA of the invention may also be used for diagnosis of disease and to monitor therapeutic response. Other uses of glycosylated SCA proteins are specific targeting of pro-drug activating enzymes to tumor cells by a bispecific molecule with specificity for tumor cells and enzyme. Glycosylated SCA may be used for specific delivery of drug to an in vivo target, such as a tumor, delivery of radioactive metals for tumor radioimmunodiagnosis or radioimmunotherapy (Goldenberg, D. M., *Am. J. Med.* 94:297 (1993)), nonradioactive metals in applications such as with boron/uranium-neutron capture therapy (Ranadive, G. N., et al., *Nucl. Med. Biol.* 20:1 (1993); Barth, R. F., et al., *Bioconjug. Chem.* 5:58 (1994)), and nuclear magnetic resonance imaging (Sieving, P. F., et al., *Bioconjug. Chem.* 1:65 (1990)). This list is illustrative only, and any use for which an oligosaccharide-specificity is appropriate comes within the scope of this invention.

The invention also extends to uses for the glycosylated SCA proteins in purification and biosensors. Affinity purification is made possible by affixing the glycosylated SCA protein to a support, with the antigen-binding sites exposed to and in contact with the ligand molecule to be separated, and thus purified. Biosensors generate a detectable signal upon binding of a specific antigen to an antigen-binding molecule, with subsequent processing of the signal. Glycosylated SCA proteins, when used as the antigen-binding molecule in biosensors, may change conformation upon binding, thus generating a signal that may be detected.

The invention is also directed to a method of detecting an antigen to suspected of being in a sample by contacting the sample with the glycosylated SCA that is labeled by its carbohydrate moiety. A sample may comprise at least one compound, mixture, surface, solution, emulsion, suspension, mixture, cell culture, fermentation culture, cell, tissue, secretion and/or derivative or extract thereof.

Such samples can also include, e.g., animal tissues, such as blood, lymph, cerebrospinal fluid (CNS), bone marrow, gastrointestinal contents, and portions, cells or internal and external secretions of skin, heart, lung and respiratory system, liver, spleen, kidney, pancreas, gall bladder, gastrointestinal tract, smooth, skeletal or cardiac muscle, circulatory system, reproductive organs, auditory system, the autonomic and central nervous system, and extracts or cell cultures thereof. Such samples can be measured using methods of the present invention in vitro, in vivo and in situ.

Such samples can also include environmental samples such as earth, air or water samples, as well as industrial or commercial samples such as compounds, mixtures, surfaces, aqueous chemical solutions, emulsions, suspensions or mixtures.

Additionally, samples that can be used in methods of the present invention include cell culture and fermentation media used for growth of prokaryotic or eukaryotic cells and/or tissues, such as bacteria, yeast, mammalian cells, plant cells and insect cells.

Essentially all of the uses for which monoclonal or polyclonal antibodies, or fragments thereof, have been envisioned by the prior art, can be addressed by the glycosylated SCA proteins of the present invention. These uses include detectably-labeled forms of the glycosylated SCA protein. Types of labels are well-known to those of ordinary skill in the art. They include radiolabeling, chemiluminescent labeling, fluorochromic labeling, and chromophoric labeling. Other uses include imaging the internal structure of an animal (including a human) by administering an effective amount of a labeled form of the glycosylated SCA protein and measuring detectable radiation associated with the animal. They also include improved immunoassays, including sandwich immunoassay, competitive immunoassay, and other immunoassays wherein the labeled antibody can be replaced by the glycosylated SCA protein of this invention. See, e.g., Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, pp. 563–681, Elsevier, N (1981); Sambrook et al., *Molecular Cloning—A Laboratory Manual*, 2nd ed., Cold Spring Harbor Laboratory (1989).

The above described uses are also intended with glycosylated SCA conjugated to polyalkylene oxide, especially for, for example, reduced immunogenicity and antigenicity and longer lifetimes in the blood stream.

Administration

Administration of glycosylated SCA conjugates of the invention for in vivo diagnostic and therapeutic applications will be by analogous methods to conjugates of the same or similar drugs, toxins, chelators, boron adducts or detectable labels where the diagnostic or therapeutic principle is directly linked to the antibody or a loaded carrier is linked by random binding to amine or carboxyl groups on amino acid residues of the antibody in a non-site-specific manner.

Conjugates of the present invention (immunoconjugates) can be formulated according to known methods to prepare pharmaceutically useful compositions, such as by admixture with a pharmaceutically acceptable carrier vehicle. Suitable vehicles and their formulation are described, for example, in *Remington's Pharmaceutical Sciences*, 18th ed., Osol, A., ed., Mack, Easton Pa. (1990). In order to form a pharmaceutically acceptable composition suitable for effective administration, such compositions will contain a therapeutically effective amount of the immunoconjugate, either alone, or with a suitable amount of carrier vehicle.

Additional pharmaceutical methods may be employed to control the duration of action. Controlled release preparations may be achieved by the use of polymers to complex or absorb the immunoconjugate of the present invention. The controlled delivery may be exercised by selecting appropriate macromolecules (for example, polyesters, polyamino acids, polyvinyl pyrrolidone, ethylenevinylacetate, methylcellulose, carboxymethylcellulose, or protamine sulfate). The rate of drug release may also be controlled by altering the concentration of such macromolecules. Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the immunoconjugate of the invention in microcapsules prepared, for example, by coacervation techniques or by interfacial polymerization, for example, by the use of hydroxymethylcellulose or gelatin-microcapsules or poly (methylmethacrylate) microcapsules, respectively, or in a colloid drug delivery system, for example, liposomes, albumin microspheres, microemulsions, nanoparticles, nanocapsules, or in macroemulsions. Such teachings are disclosed in *Remington's Pharmaceutical Sciences*, 16th ed., Osol, A., ed., Mack, Easton Pa. (1990).

The immunoconjugate may be provided to a patient by means well known in the art. Such means of introduction include oral means, intranasal means, subcutaneous means, intramuscular means, intravenous means, intra-arterial means, or parenteral means. Intravenous, intraarterial or intrapleural administration is normally used for lung, breast, and leukemic tumors. Intraperitoneal administration is advised for ovarian tumors. Intrathecal administration is advised for brain tumors and leukemia. Subcutaneous administration is advised for Hodgkin's disease, lymphoma and breast carcinoma. Catheter perfusion is useful for metastatic lung, breast or germ cell carcinomas of the liver. Intralesional administration is useful for lung and breast lesions.

For therapeutic or diagnostic applications, compositions according to the invention may be administered parenterally in combination with conventional injectable liquid carriers such as sterile pyrogen-free water, sterile peroxide-free ethyl oleate, dehydrated alcohol, or propylene glycol. Conventional pharmaceutical adjuvants for injection solution such as stabilizing agent, solubilizing agents and buffers, such as ethanol, complex forming agents such as ethylene diamine tetraacetic acid, tartrate and citrate buffers, and high-molecular weight polymers such as polyethylene oxide for viscosity regulation may be added. Such compositions may be injected intramuscularly, intraperitoneally, or intravenously.

Further non-limiting examples of carriers and diluents include albumin and/or other plasma protein components such as low density lipoproteins, high density lipoproteins and the lipids with which these serum proteins are associated. These lipids include phosphatidyl choline, phosphatidyl serine, phosphatidyl ethanolamine and neutral lipids such as triglycerides. Lipid carriers also include, without limitation, tocopherol.

At least one glycosylated SCA linked to a therapeutic agent according to the invention may be administered by any means that achieve their intended purpose, for example, to treat various pathologies, such as cell inflammatory, allergy, tissue damage or other related pathologies.

A typical regimen for preventing, suppressing, or treating various pathologies comprises administration of an effective amount of an SCA conjugate, administered over a period of one or several days, up to and including between one week and about 24 months.

It is understood that the dosage of the present invention administered in vivo or in vitro will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the most preferred dosage will be tailored to the individual subject, as is understood and determinable by one of skill in the art, without undue experimentation. See, e.g., Berkow et al., eds., *Merck Manual*, 16th edition, Merck and Co., Rahway, N.J. (1992); Goodman et al., eds., *Goodman and Gilman's The Pharmacological Basis of Therapeutics*, 8th edition, Pergamon Press, Inc., Elmsford, N.Y. (1990); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston (1985), Katzung, *Basic and Clinical Phamacology*, Appleton and Lange, Norwalk, Conn. (1992), which references and references cited therein, are entirely incorporated herein by reference.

The total dose required for each treatment may be administered by multiple doses or in a single dose. Effective amounts of a diagnostic/pharmaceutical compound or composition of the present invention are from about 0.001 µg to about 100 mg/kg body weight, administered at intervals of 4–72 hours, for a period of 2 hours to 5 years, or any range or value therein, such as 0.01–1.0, 1.0–10, 10–50 and 50–100 mg/kg, at intervals of 1–4, 6–12, 12–24 and 24–72 hours, for a period of 0.5, 1.0–2.0, 2.0–4.0 and 4.0–7.0 days, or 1, 1–2, 2–4, 4–52 or more weeks, or 1, 2, 3–10, 10–20, 20–60 or more years, or any range or value therein.

Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods. See, e.g., Berker, supra, Goodman, supra, Avery, supra and Ebadi, supra, which disclosures are entirely incorporated herein by reference, including all references cited therein.

Pharmaceutical compositions comprising at least one type of SCA conjugate of the invention, or, 1, 2, 3, 4, 5, 6, 7, 8, 9 or 10 types of SCA conjugates, of the present invention may be contained in an amount effective to achieve its intended purpose. In addition to at least one SCA conjugate, a pharmaceutical composition may contain suitable pharmaceutically acceptable carriers, such as excipients, carriers and/or auxiliaries which facilitate processing of the active compounds into preparations which can be used pharmaceutically.

Pharmaceutical compositions may also include suitable solutions for administration intravenously, subcutaneously, dermally, orally, mucosally or rectally, and contain from about 0.01 to 99 percent, preferably from about 20 to 75 percent of active component (i.e., the SCA) together with the excipient. Pharmaceutical compositions for oral administration include tablets and capsules. Compositions which can be administered rectally include suppositories. See, e.g., Berker, supra, Goodman, supra, Avery, supra and Ebadi, supra. Additional lipid and lipoprotein drug delivery systems that may be included herein are described more fully in *Annals N.Y. Acad. Sci.* 507:775–88, 98–103, and 252–271, which disclosure is incorporated herein by reference.

The compositions may also be formulated into orally administrable compositions containing one or more physiologically compatible carriers or excipients, and may be solid or liquid in form. These compositions may, if desired, contain conventional ingredients such as binding agents, for example, syrups, acacia, gelatin, sorbitol, tragacanth, or polyvinylpyrrolidone; fillers, such as lactose, mannitol, starch, calcium phosphate, sorbitol, cyclodextran, or methylcellulose; lubricants such as magnesium stearate, high molecular weight polymers such as polyethylene glycols, high molecular weight fatty acids such as stearic acid or silica; disintegrants such as starch; acceptable wetting agents as, for example, sodium lauryl sulfate.

The oral compositions may assume any convenient form, such as tablets, capsules, lozenges, aqueous or oily suspensions, emulsions, or dry products suitable for reconstitution with water or other liquid medium prior to use. The liquid oral forms may, of course, contain flavors, sweeteners, preservatives such as methyl or propyl p-hydroxybenzoates; suspending agents such as sorbitol, glucose or other sugar syrup, methyl, hydroxymethyl, or carboxymethyl celluloses or gelatin; emulsifying agents such as lecithin or sorbitan monooleate or thickening agents. Non-aqueous compositions may also be formulated which comprise edible oils as, for example, fish-liver or vegetable oils. These liquid compositions may conveniently be encapsulated in, for example, gelatin capsules in a unit dosage amount.

The pharmaceutical compositions according to the present invention may also be administered, if appropriate, either topically as an aerosol or, formulated with conventional bases as a cream or ointment.

The pharmaceutical compositions of the present invention can also be administered by incorporating the active ingredient into colloidal carriers, such as liposomes. Liposome technology is well known in the art, having been described by Allison et al., *Nature* 252:252–254 (1974), and Dancy et al., *J. Immunol.* 120:1109–1113 (1978).

The above described administration of the compositions also include the glycosylated SCA conjugated to polyalkylene oxide.

Having generally described the invention, the same will be more readily understood by reference to the following examples, which are provided by way of illustration and are not intended as limiting.

EXAMPLES

Example 1

Synthesis of Asn-linked Glycosylation Sequences in CC49/218 and Expression of the Glycosylated SCA The CC49 monoclonal antibody was developed by Dr. Jeffrey Schlom's group at Laboratory of Tumor Immunology and Biology, National Cancer Institute. It binds specifically to the pan-carcinoma tumor antigen TAG-72 (see, Muraro, R., et al., *Cancer Res.* 48:4588–4596 (1988)). The SCA gene version of CC49 has been described by Milenic et al., *Cancer Res.* 51:6363–6371 (1991). Oligonucleotide-directed mutagenesis was employed to create Asn-linked glycosylation sequences in CC49/218 (the 218 linker is described in the "Detailed Description of the Preferred Embodiments" section, supra), as shown in the DNA sequences presented in FIGS. 1A and 1B (i.e., (1) two $V_L$ changes; (2) two $V_H$ changes; (3) one linker change; (4) one C-terminal change). Oligonucleotide-directed mutagenesis was also employed to create two or three tandem or overlapping glycosylation sites in CC49/218. Additionally, mutant genes were made having all six changes, five changes excluding C-terminus change, and C-terminus plus linker changes. These mutant CC49 genes and the nonmutated CC49 SCA gene were individually ligated into the Pichia transfer plasmid pHIL-S 1 (Invitrogen Corp.) and transformed into the yeast *Pichia pastoris*. Detailed protocols for these procedures are presented in the Pichia Expression Kit Instruction Manual Cat. No. X1710-01(1994) from Invitrogen Corporation. The CC49 gene variants were placed behind a yeast signal sequence in these constructions and the integrated SCA genes in the yeast transformants were tested for secretion of the SCA protein or glycoprotein products. Evaluation of expression was done by Coomassie Blue staining of SDS-PAGE gels.

The unmodified CC49/218 SCA (~27 kDa) was expressed (secreted) at high levels in recombinant Pichia (about 20–100 mg/l depending on integrated gene copy number). All of the mutant genes described above gave detectable (though reduced) expression of secreted glyco-SCA plus unglycosylated SCA as observed by protein bands in the ~27–35 kDa range. Each glycosylation event would be predicted to add ~2–3 kDa of mass since Pichia is reported to add oligo-mannose chains of about 8–14 residues to the core N-Acetylglucosamines (Cregg, J. M., et al., *Bio/Technol.* 11:905–910 (1993). The C-terminal mutant gave the highest level of expression (secretion) and two prominent bands of ~27 kDa and ~30 kDa in about equal proportions. Expression of secreted glyco-SCA by the mutants is summarized in Table 2.

TABLE 2

| CC49 SCA Clone | Glyco-SCA | Unmodified SCA |
| --- | --- | --- |
| CC49 parent (EN225) | – | ++++ |
| Linker mutant | + | ++ |
| C-terminal mutant (EN235) | ++ | ++ |
| C-terminus plus linker mutant (EN236) | ++ | ++ |
| Five changes mutant | + | + |
| All six changes mutant | + | + |

These results indicate that there were some glycosylation of all mutant SCA proteins and show that the C-terminal mutant gave the highest expression (secretion) of glyco-SCA. This mutant was chosen for more detailed study.

Figure 2B:
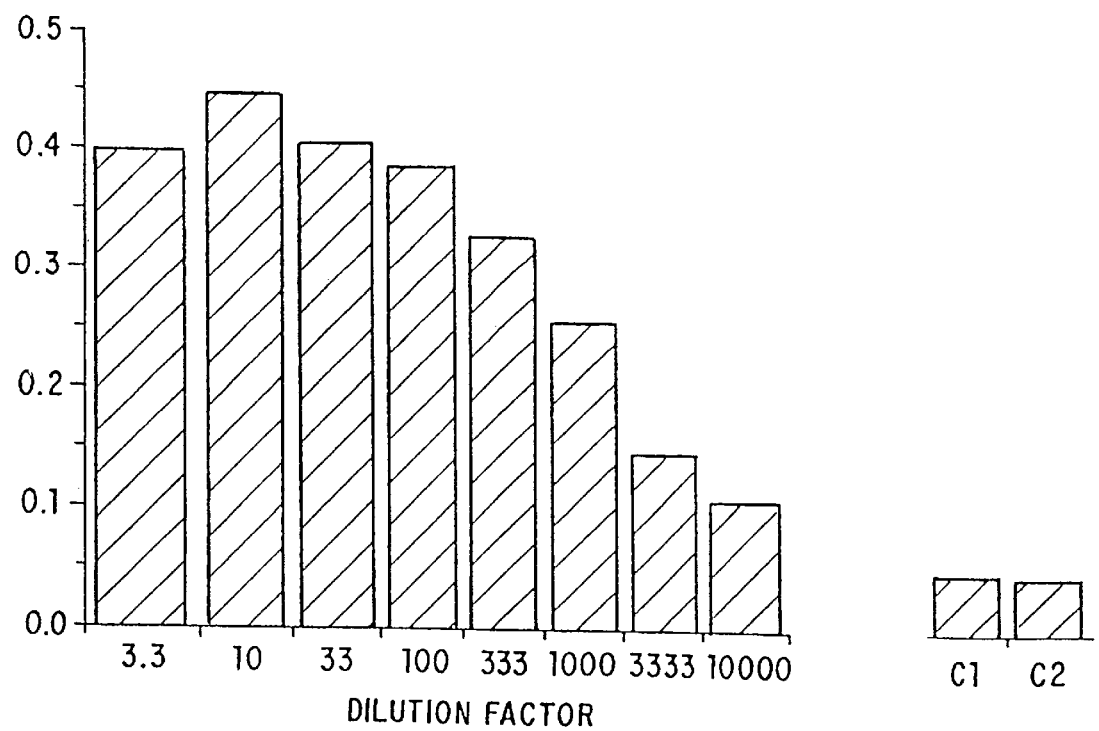

The purified CC49/218 SCA from *E. coli* GX9251 and the unpurified culture supernatant from *P. pastoris* EN225 were assayed for direct binding to antigen, bovine submaxillary mucin, by ELISA. As shown in FIGS. 2A and 2B, the parent CC49/218 SCA product from both *E. coli* and Pichia were shown to be active in binding bovine submaxillary mucin by ELISA. This indicates that CC49/218 SCA produced in Pichia is active.

Figure 3:
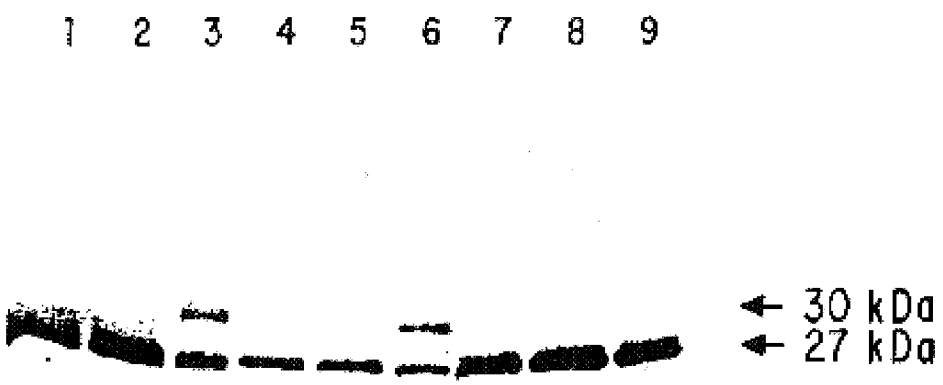
FIG. 3. Western blot analysis of CC49/218 SCA and glyco-SCA before and after enzymatic treatment with N-acetylglucosamine specific endoglycosidases. Unpurified CC49/218 SCA from culture supernatants of EN225, EN235 and EN236 were digested with Peptide-N-glycosidase F or Endo-glycosidase H. The samples (~1 µg per lane) were run on a 4–20% SDS-PAGE slab gel and transferred to a nitrocellulose membrane for Western analysis using a rabbit anti-CC49/218 SCA polyclonal antibody. Lanes 1–3, EN236; Lanes 4–6, EN235; Lanes 7–9, EN225. Lanes 1, 4, and 7, Endo-glycosidase H treated; Lanes 2, 5, and 8, Peptide-N-glycosidase F treated; Lanes 3, 6, and 9, untreated. The flanking lane 10 (not shown) contained molecular weight markers and showed no cross reactivity to the antibody.

The C-terminal plus linker double mutant (EN236) CC49/218 SCA was run on a SDS-PAGE gel (FIG. 3). The upper band of the doublet was selectively stained by using the GlycoTrack Carbohydrate Kit K-050 from Oxford Glyco-Systems as described by the manufacturer. The lower ~27 kDa (unmodified) band was unstained indicating that the ~30 kDa band was a glycoprotein.

Further, the C-terminus mutant (EN235) and C-terminal plus linker double mutant (EN236) CC49/218 SCAs were digested with the glycosidase Peptide-N-glycosidase (PNGase) F or Endo-glycosidase H (Oxford Glycosystems) which will specifically cleave Asparagine-linked (N-linked) carbohydrate from the polypeptide chain. Following PNGase F or Endo-glycosidase H treatment, the samples were analyzed by SDS-PAGE which showed that the former doublets (~27 and ~30 kDa) were converted to a single ~27 kDa band by Coomassie staining. As shown in FIG. 3, Western analysis using an anti-CC49 SCA rabbit serum antibody (HRP Inc.) confirmed that both bands of the expressed protein doublet from the C-terminus and C-terminal plus linker double mutants react with this CC49 specific antibody.

Figure 4A:
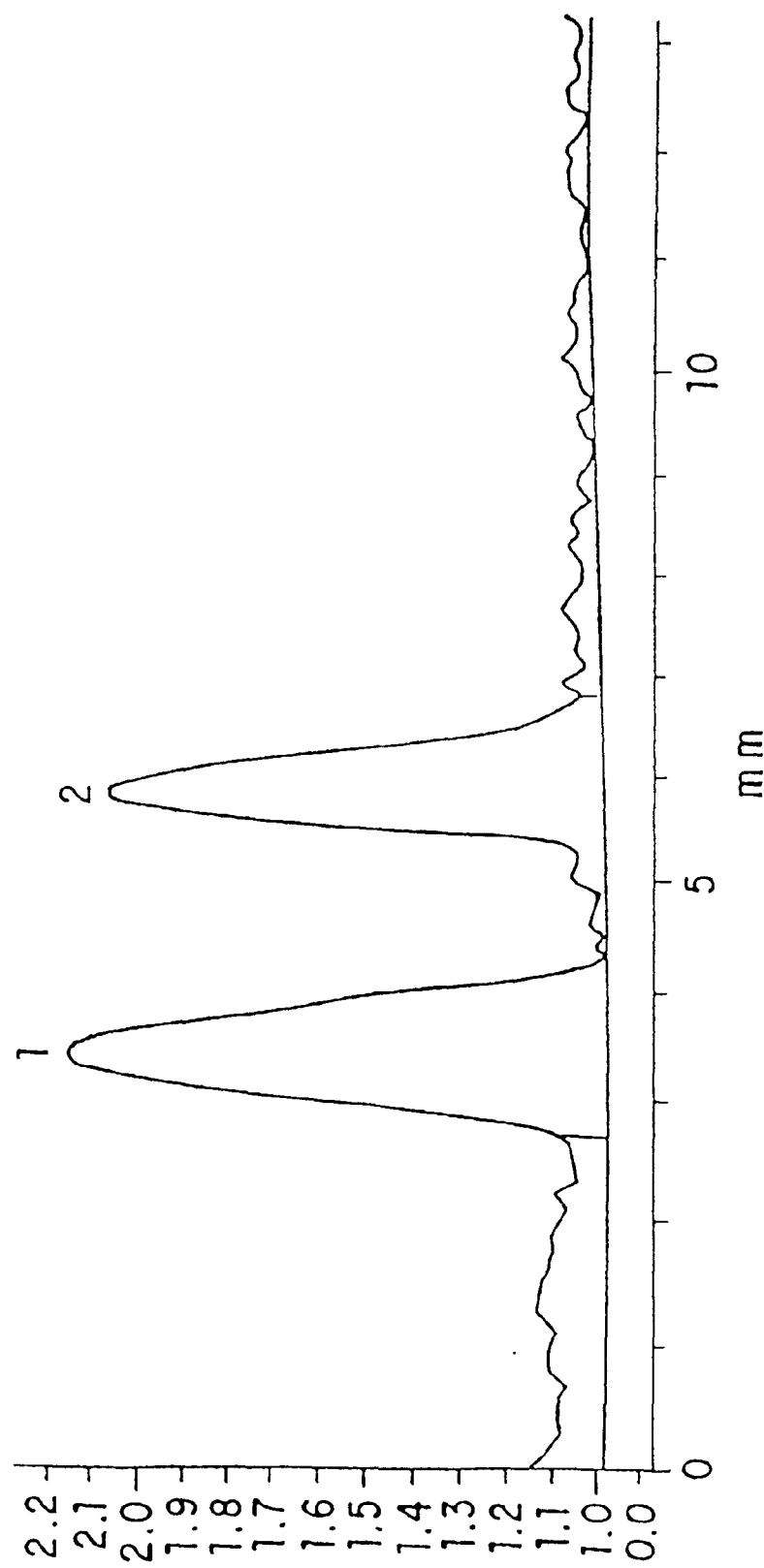
FIGS. 4A and 4B. Affinity chromatography of CC49/218 SCA from culture supernatant of EN235. SDS-PAGE analysis was performed on EN235 derived mixture of unmodified SCA and glyco-SCA following chromatography on a mucin-Sepharose column as described in the "Materials and Methods" section of Example 1. The Coomassie Blue stained gel was scanned using a Molecular Dynamics Laser Scanner Model PD-SI and the area quantitation is displayed for the purified sample (FIG. 4A) and the starting supernatant (FIG. 4B). The ratios of glycosylated SCA (peak 1) to unmodified SCA (peak 2) are 1.2 (FIG. 4A) and 1.1 (FIG. 4B).
Figure 4B:
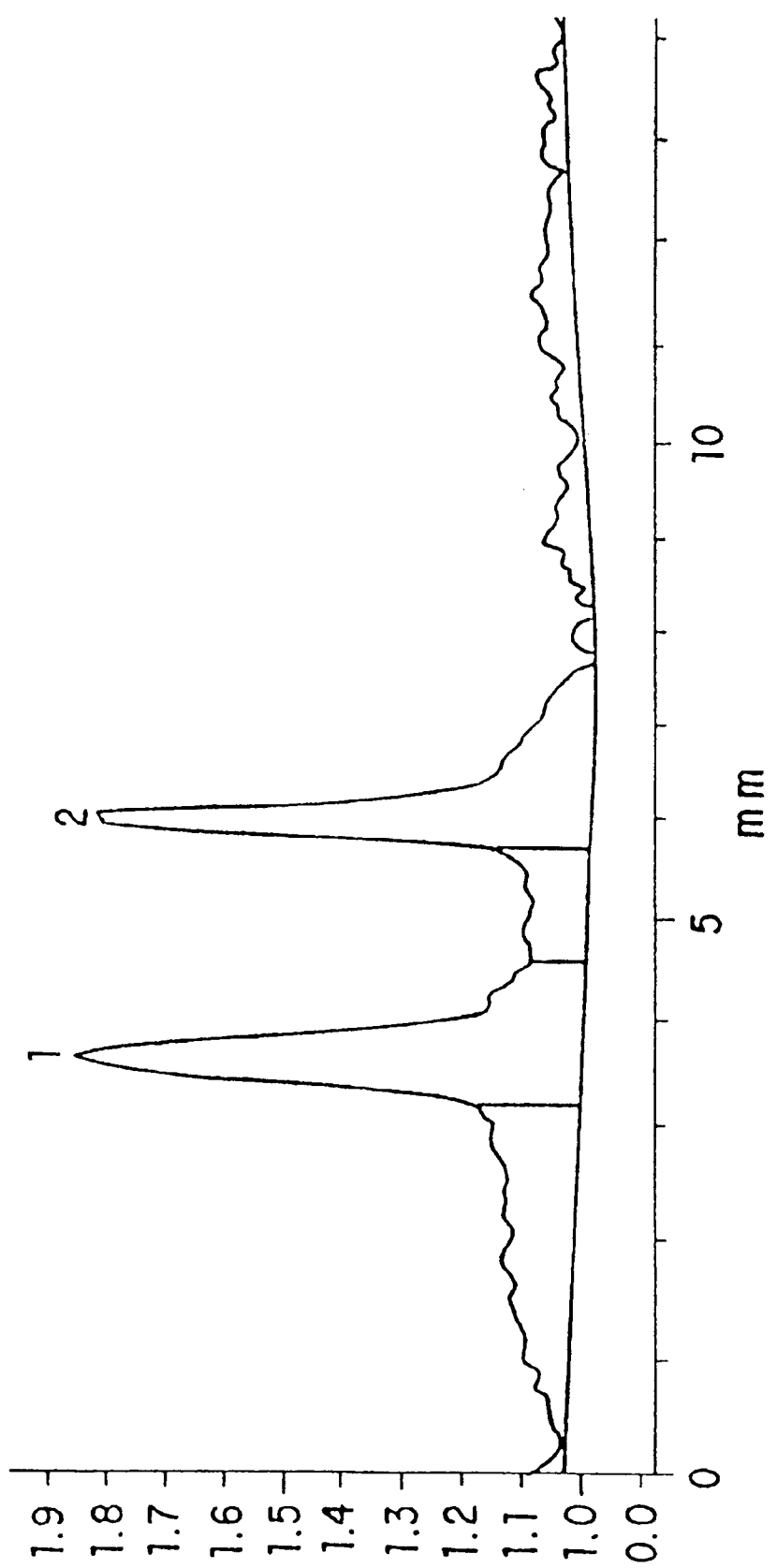

The C-terminus mutant CC49/218 SCA doublet proteins were bound to a bovine submaxillary mucin-Sepharose affinity column and eluted by increasing urea concentrations. As shown in FIGS. 4A and 4B, the bound and eluted doublet appeared in equal stoichiometry as in the starting sample indicating that the glyco-SCA maintains mucin-binding specificity.

Figure 5A:
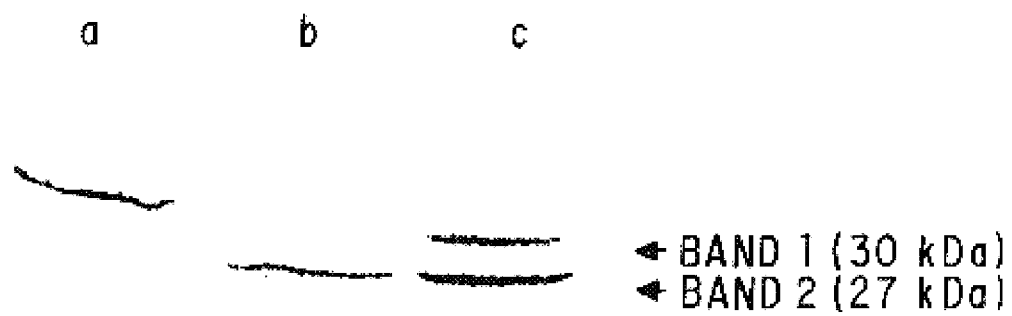

CC49/218 SCA from EN235 culture supernatant was incubated with molar excess of Con A Sepharose resin (Pharmacia Biotech). The unbound supernatant fraction was removed, and the bound fraction was eluted with alpha-D-methylmannoside. As shown in FIGS. 5A and 5B(a–c), the glycosylated bound fraction was ~30 kDa whereas the unglycosylated unbound fraction was ~27 kDa.

Figure 9:
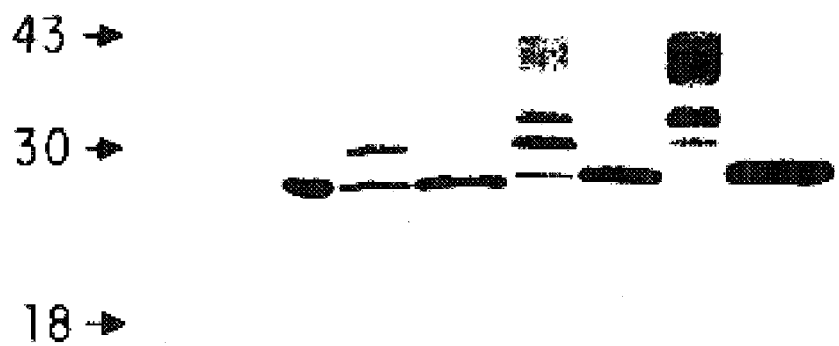
FIG. 9. Western blot analysis of CC49/218 SCA and glyco-CC49/218 SCA, having one, two, or three glycosylation sites, before and after treatment with Endo-glycosidase H. Conditions were as described above. Lane 1, control *P. pastoris* host GS115; Lane 2, CC49/218 SCA; Lanes 3 and 4, glyco-CC49/218 SCA EN236 (one glycosylation site); Lanes 5 and 6, glyco-CC49/218 SCA EN279 (two glycosylation sites); Lanes 7 and 8, glyco-CC49/218 SCA EN280 (three glycosylation sites). Lanes 4, 6, and 8, treated with Endo-glycosidase H.

CC49 SCA with one, two or three glycosylation sequences in the C-terminus are shown in FIG. 9. Western blot analysis of CC49 SCA with one glycosylation site (FIG. 9, lanes 3 and 4) adjacent to the C-terminus shows that it is a mixture of modified (~30 kDa band) and unmodified (~27 kDa band) polypeptides. CC49 SCA with two glycosylation sites (FIG. 9, lanes 5 and 6) had a smaller percentage of unmodified polypeptides, a mixture of one and two glycosylation site species, and a hyperglycosylated species (~43 kDa band). CC49 with three glycosylation sites (FIG. 9, lanes 7 and 8) had virtually no unmodified polypeptides, a mixture of two glycosylation site species and the hyperglycosylated species.

The SCA containing three glycosylation sequences (FIG. 9, lanes 7 and 8) had mainly two attached oligosaccharides or hyperglycosylated species (and virtually no unmodified protein). The higher molecular weight hyperglycosylated species may include both the three positions attachments and/or more extensive longer-chain oligosaccharide attachments at one or more positions of glycosylation.

Figure 10:
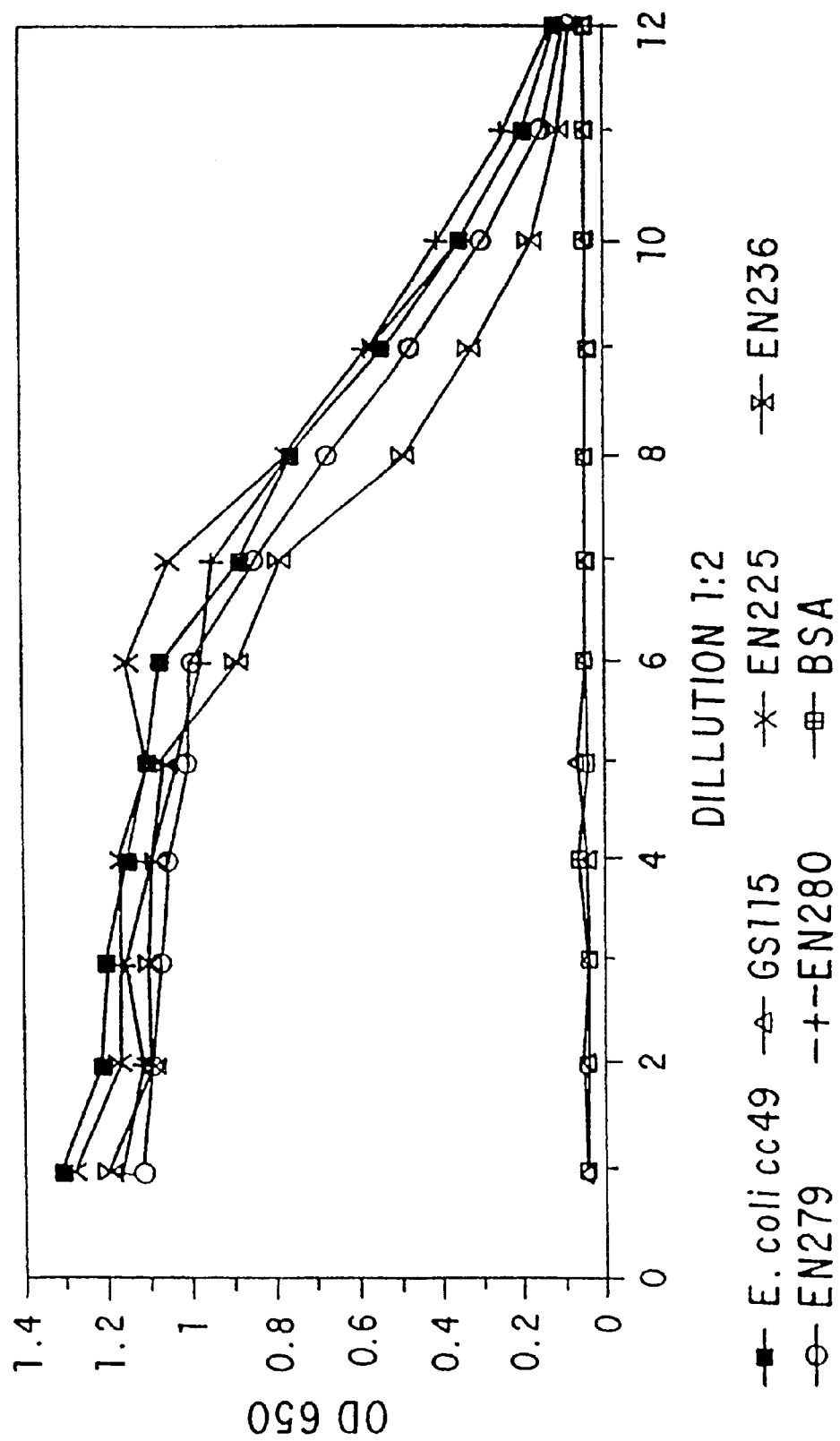
FIG. 10. ELISA quantitation of mucin-binding activity by unmodified CC49 SCA (*E. coli* CC49 and *P. pastoris* EN 225) and CC49 with one (EN 236), two (EN 279), or three (EN 280) glycosylation sites. The two controls, BSA and GS115 (*P. pastoris* host), showed very little mucin binding activity. -■-=BSA; -●-=*E. coli* CC49; -▲-=GS115; -✱-=EN225; -✣-=EN236; -●-=EN279; and -+-=EN280.

The unmodified CC49 SCA (*E. coli* CC49 and *P. pastoris* EN225), EN236 (one C-terminal glycosylation sequence), EN279 (two glycosylation sequences), and EN280 (three glycosylation sequences) were assayed for direct binding to antigen, bovine submaxillary mucin, by ELISA (FIG. 10). The two controls, BSA and GS 115 (*P. pastoris* host) showed little mucin binding activity.

Materials and Methods

Materials. The gene for CC49/218 SCA was obtained from plasmid pGX5608 (Enzon, Inc.). The complete DNA sequence of CC49/218 SCA has been reported (Filpula, D., et al., "Production of Single-chain Fv Monomers and Multimers, In: Antibody Engineering: A Practical Approach (J. McCafferty, H. Hoogenboom, and D. J. Chiswell, eds., Oxford University Press, Oxford, UK), pp. 253–268 (1996)). Oligonucleotides were synthesized using a Millipore Cyclone DNA Synthesizer. The GlycoTrack Carbohydrate Detection Kit K-050, Endoglycosidase H, and Peptide-N-Glycosidase F were purchased from Oxford GlycoSystems (Rosedale, N.Y.). Pre-cast polyacrylamide slab gels (4–20%) were obtained from Novex Corporation (San Diego, Calif.). Bovine submaxillary mucin type I, porcine submaxillary mucin type III and CNBr-activated Sepharose 4B were purchased from Sigma Inc. (St. Louis, Mo.). Con A Sepharose was obtained from Pharmacia Biotech (Piscataway, N.J.). Purified CC49/218 SCA protein derived from *E. coli* GX9251 was obtained from Enzon, Inc. Rabbit anti-CC49/218 SCA polyclonal antibody was obtained from HRP Inc. (Denver, Pa.). Mouse anti-CC49/218 polyclonal antibody was obtained from Enzon, Inc.

SCA gene constructions. The CC49/218 SCA gene from plasmid pGX5608 was modified by oligonucleotide-directed mutagenesis using the procedure of Ho et al., *Gene* 77:51–59 (1989). The six designated changes for N-linked glycosylation (N-X-T/S) are indicated in FIGS. 1A and 1B. DNA sequence analysis using T7 Sequenase version 2.0 (Amersham Corporation, Arlington Heights, Ill.) was performed according to the manufacturer's instructions to confirm the correct constructions. For the final construction of the EN235 SCA gene which is ligatable as an EcoRI -BamHI fragment to *P. pastoris* vector pHIL-S 1, the primer pair 5'-CGGAATTCGACGTCGTGATGTCACAG -3' (SEQ ID NO: 19) and 5'-CCAGGATCCTATTAACTGG CTTGTTG-GAGACGGTGACTGA -3' (SEQ ID NO: 20) were used in a PCR reaction.

The designated changes for two and three tandem or overlapping N-linked glycosylation sites are provided below.

Manual" from Invitrogen Corporation, San Diego, Calif. (Cat. No. K1710–01; 1994). Transformation of *P. pastoris* GS115 with the pHIL-S1/SCA vectors was performed by the spheroplast transformation procedure followed by isolation of His⁺ and Mut⁻ phenotypes. Growth protocols in BMGY and BMMY were also performed as described in the Invitrogen manual. After 48 hours of growth in the BMMY medium at 30° C., the induced culture supernatants were collected following centrifugation.

SDS-PAGE. Polyacrylamide gel electrophoresis in the presence of SDS was performed using pre-cast 4–20% slab gels from Novex Corporation (San Diego, Calif.) according to the manufacturer's instructions. Protein bands were visualized by staining with Coomassie Blue. Area quantitation of stained bands was performed using a Molecular Dynamics PD-SI laser scanner.

Western Analysis. Immunoblotting procedures for transfer of proteins from gels to nitrocellulose membranes by the semi-dry method was performed as described in Harlow, E., & Lane, D., *Antibodies*: A Laboratory Manual, Cold Spring Harbor Laboratory Press, Cold Spring Harbor, N.Y., (1988). Blot development was also performed according to the procedures in this manual. Briefly, the blotted membranes were blocked in 1% BSA blocking reagent in PBS at room temperature for 2 hr; washed 3× with PBS; and incubated with 3% BSA in PBS with a 1:1,000 dilution of rabbit anti-CC49/218 SCA antibody at 4° C. overnight. Next, a 3%

```
C-terminal of CC49 with double glycosylation sites:

Ser Val Thr Val Ser Asn Lys Thr Asn Ala Thr Ser Stop   BamHI        (SEQ ID NO: 14)

TCA GTC ACC GTC TCC AAC AAG ACC AAT GCT ACC TCT TAA TAG GAT CC      (SEQ ID NO: 13)

C-terminal of CC49 with triple glycosylation sites:

Ser Val Thr Val Ser Asn Lys Thr Asn Asn Thr Thr Ser Stop BamHI      (SEQ ID NO: 16)

TCA GTC ACC GTC TCC AAC AAG ACC AAC AAT ACT ACC TCT TAA G GAT CC    (SEQ ID NO: 15)
```

Oligonucleotide 5228: 3'PCR primer for cloning two N-linked glycosylation sites at C-terminal of CC49 into BamHI site of vector PhilS1:

5' CCG GGA TCC TAT TAA GAG GTA GCA TTG GTC TTG TTG GAG ACG GTG (SEQ ID NO: 21)

Oligonucleotide 5229: 3'PCR primer to put three N-linked glycosylation sites at C-terminal of CC49 into BamHI site of vector PhilS 1:

5' CCG GGA TCC TTA AGA GGT AGT ATT GTT GGT CTT GTT GGA GACGGTG (SEQ ID NO: 22)

Oligonucleotide 5230: 3'PCR primer to put two N-linked glycosylation sites at C-terminal of CC49 into EcoRi site of vector pPic9:

5' CCG GAA TTC TAT TAA GAG GTA GCA TTG GTC TTG TTG GAG ACG GTG (SEQ ID NO: 23)

Expression of SCA in *Pichia pastoris*. The Pichia expression vector pHIL-S 1 (Invitrogen Corporation) was used for expression of both the unmodified and glycosylated SCA. This vector provides a signal sequence derived from the yeast gene PH01 which is fused to the gene of interest. The fusion point is at an EcoRI site. After signal processing, the predicted N-terminal sequence of the SCA proteins will be REFD—where the normal N-terminus D (in italics) is preceded by three amino acids. All cloning and expression procedures for production of SCA in Pichia were carried out as described in the "Pichia Expression Kit Instruction BSA in PBS solution containing a 1:1000 dilution of horseradish peroxidase conjugated goat anti-rabbit IgG was used in a 1 hr incubation at room temperature. After washing with PBS, the membranes were developed with TMBM-500 (MOSS, Inc.) at room temperature for 1 min.

Mucin-Sepharose Chromatography. The protocol for preparation of antigen-coupled cyanogen bromide-activated beads is described in Harlow, E., & Lane, D., *Antibodies*: A Laboratory Manual, Cold Spring Harbor Laboratory Press, Cold Spring Harbor, N.Y., (1988). CNBr-activated Sepharose 4B (Sigma Corporation, Cat. No. C9142) was coupled to bovine submaxillary mucin (Sigma Corporation, Cat. No. M4503). Five mg of mucin was dissolved in 1 ml of 0.1 M NaHCO₃, 0.5 M NaCl, pH 8.3. A 2.5 g aliquot of CNBr-activated resin was swollen in 1 mM HCl. The mucin solution was next gently mixed with the resin for 1 hr at 22° C. After washing off unbound mucin with 25 ml of the above coupling buffer, the Sepharose 4B-mucin was transferred into 0.1 M Tris-HC1, pH 8.0. The resin was washed with 0.1 M sodium acetate, pH 4.0, 0.5 M NaCl; and 0.1 M Tris-HCl, pH 8.0, 0.5 M NaCl, alternately for three cycles. The gel was poured into a 10 ml column and washed with 25 ml of 0.1 M Tris-HCl, pH 8.0, 0.1 M NaCl. The EN235 Pichia culture supernatant was dialyzed against 0.1 M Tris-HCl, pH 7.4, 0.1 M NaCl at 4° C. overnight, then loaded onto the mucin-Sepharose column. The column was washed with 0.1 M Tris-HCl, pH 8.0, 0.1 M NaCl until the OD280=0 (~50 ml). Elution of the bound SCA proteins was performed by using 10 ml of eluent 1 (0.1 M sodium citrate, pH 4.0) followed by 10 ml of eluent2 (8 M urea, 0.1 M Tris-HCl, pH 7.4). The bound SCA eluted in eluent 2.

Endoglycosidase Digestion. Peptide-N-Glycosidase F and Endo-glycosidase H were obtained from Oxford GlycoSystems (Rosedale, N.Y.) and used according to the accompanying product literature.

Glycoprotein Staining. The GlycoTrack™ carbohydrate detection kit (Cat. No. K-050) was purchased from Oxford GlycoSystems (Rosedale, N.Y.) and used according to the manufacturer's instructions.

Binding of Glyco-SCA to Con A Sepharose. Con A Sepharose was obtained from Pharmacia Biotech (Cat. No. 17-0440-03) and was used according to the manufacturer's instructions. One ml of resin in binding buffer (20 mM Tris-HCl, pH 7.4, 0.5 M NaCl) was incubated with 50 µl of dialyzed EN235 culture supernatant for 30 min at 22° C. The beads were pelleted by microcentrifugation, and the supernatant was removed. Elution of the bound glyco-SCA was performed by washing the resin with binding buffer containing 0.2 M alpha-D-methylmannoside.

ELISA for SCA Binding Activity. Immunoassay procedures were performed using modifications of protocols from Harlow, E., & Lane, D., *Antibodies*: A Laboratory Manual, Cold Spring Harbor Laboratory Press, Cold Spring Harbor, N.Y., (1988). Direct binding assays were performed and a dose response curve was constructed. Bovine submaxillary mucin (250 ng per 100 µl well) antigen was used to coat microtiter plate wells (MaxiSorp, Nunc, VWR Scientific, Boston, Mass.). The EN225 or purified CC49/218 SCA proteins were diluted serially in PBS containing 1% BSA and incubated in the coated wells at 22° C. for 1 hr. After the plate was washed with PBS containing 0.05% Tween 20 (PBS-T), the bound SCA was detected by a 1 hr incubation with a secondary antibody (mouse anti-CC49/218), followed by a PBS-T wash, and a 1 hr incubation with an alkaline phosphatase conjugated rabbit anti-mouse IgG antibody. (For FIG. 10, horseradish peroxidase conjugated goat anti-rabbit IgG was used.) Signal generation was performed using PNPP as described in Harlow and Lane (page 597). The plate was read at 405 nm using a Molecular Devices (Sunnyvale, Calif.) plate reader.

Example 2

Synthesis of Asn-linked Glycosylation Sequences in other SCAs

Using the methods described in Example 1, oligonucleotide-directed mutagenesis is employed to create Asn-linked glycosylation consensus sequences in the identified loop regions of a Kabat consensus $V_KI/218/V_HIII$ SCA, C6.5/218 SCA, and A33/218 SCA, as shown in FIGS. 6-8, respectively (i.e., (1) two $V_L$ changes; (2) two $V_H$ changes; (3) one linker change; (4) one C-terminal change; or (5) combinations thereof). In $V_KI/218/V_HIII$ SCA and C6.5/218 SCA, proline residues flanking the tripeptide sequence in the +3 position are changed to alanines, as recommended by the compilation of Gavel, Y., and von Heijne, G., *Protein Engng.* 3:433–442 (1990). Amino acid assignments of the Kabat consensus $V_KI/218/V_HIII$ SCA and A33/218 SCA are according to Kabat et al., *Sequences of Proteins of Immunological Interest*, pp. 108 & 331, 5th ed., U.S. Dept. Health and Human Services, Bethesda, Md. (1991), where the assigned amino acid residue at a position is the most commonly occurring amino acid at that position. Amino acid assignments of the wild-type C6.5 variable domains are according to Schier, R., et al., *J. Mol. Biol.* 255:28–43 (1996).

As described in the "Materials and Methods" section of Example 1, the mutated SCAs are individually ligated into the Pichia transfer plasmid pHIL-S 1 (Invitrogen Corp.) and transformed into *Pichia pastoris*. Detailed protocols for these procedures are presented in the Pichia Expression Kit Instruction Manual Cat. No. X1710–01 (1994) from Invitrogen Corporation. The SCA variants are placed behind a yeast signal sequence in these constructions and the integrated SCA in the yeast transformants are tested for secretion of the SCA protein or glycoprotein products. Evaluation of expression is done by Coomassie staining of SDS-PAGE gels. Further tests can be done to confirm expression of glycosylated SCAs as described in Example 1.

Example 3

Purification of Glyco-CC49

The Pichia cells were harvested from a fermenter and centrifuged at 5000 rpm for 40 minutes. The clarified medium was collected and filtered through a 0.22 um filter. The sample was dialyzed against water with a membrane of molecular weight cut off of 3500 to a final conductivity of less than 1 mS. A cation exchange column (Poros-HS) was equilibrated with 15 mM Tris-Acetate at pH 6.15. The sample was adjusted to pH 6.2 and loaded onto the column. Glyco-CC49 was then eluted out with a salt concentration of 0. 15 M NaCl in Tris-acetate buffer pH 7.4. It was then passed through a Poros-HQ column equilibrated with 0.15 M NaCl. Tris-acetate buffer pH 7.4. The flow through material was then processed on a size exclusion column (Pharmacia, Superdex-75). The fractions corresponding to a molecular weight of 25–35 kDa were collected.

Example 4

Site Specific PEGylation of Double Site-Single Chain gCC49/2 by PEG-Hydrazide

Purified gCC49/2 (EN279) was concentrated to 2 mg/ml in Tris-HCl, pH7, 0.1 M NaCl and then passed through a size exclusion column (Superdex-75) into PEGYLATION buffer (0.1 M acetate, pH 5.5). Sodium periodate was added so that the final concentration was 10 mM. The sample was oxidized for 1 hour in the dark at room temperature. At the end of the reaction, glycerol was added to a final concentration of 5% and the sample was loaded onto a size exclusion column to remove unreacted sodium periodate. The protein was then concentrated to 2 mg/ml.

PEG-hydrazide (5000 molecular weight) (Shearwater) dissolved in the same buffer was added to the protein at a molar ratio of PEG:protein=100:1. The reaction was allowed to proceed at 37° C. with shaking for 2.5 hours.

Sodium borohydride made in PBS (phosphate buffered saline) was added to the reaction mixture to a final concentration of 10 mM. It was then stirred for 10 minutes at room temperature.

Figure 11A:
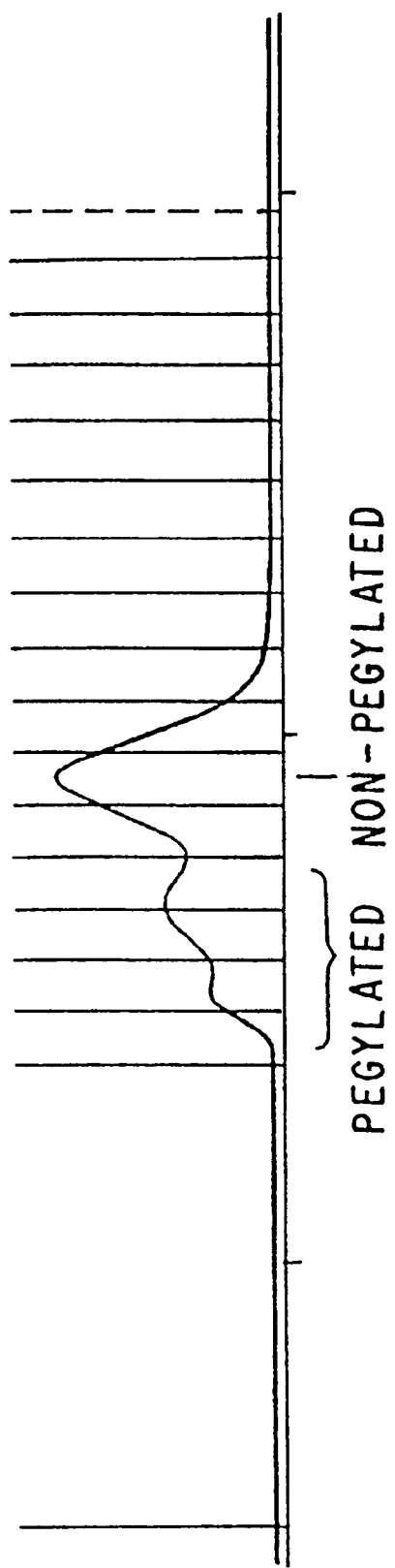
FIGS. 11A and 11B.
Figure 11B:
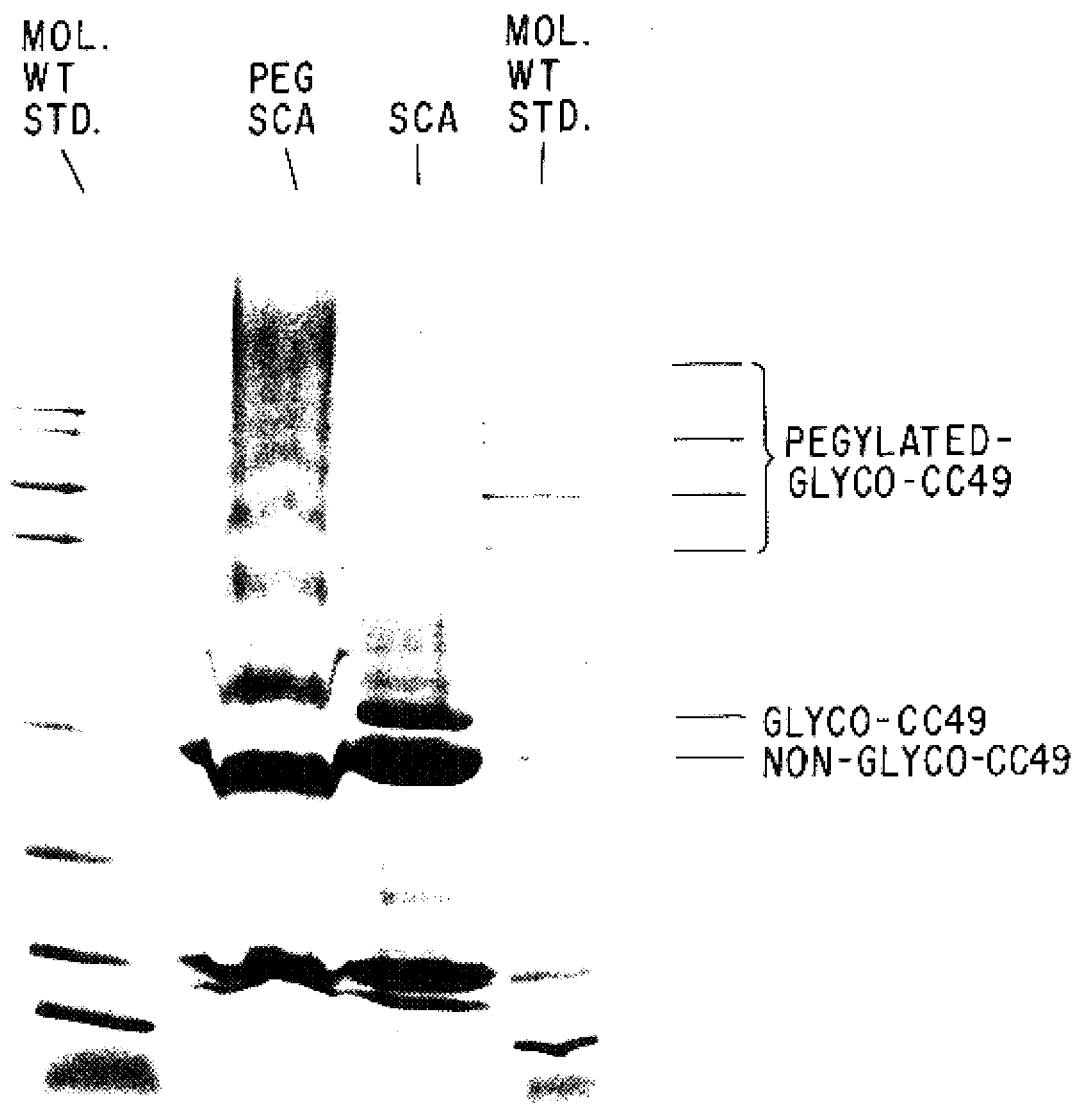
Figure 12:
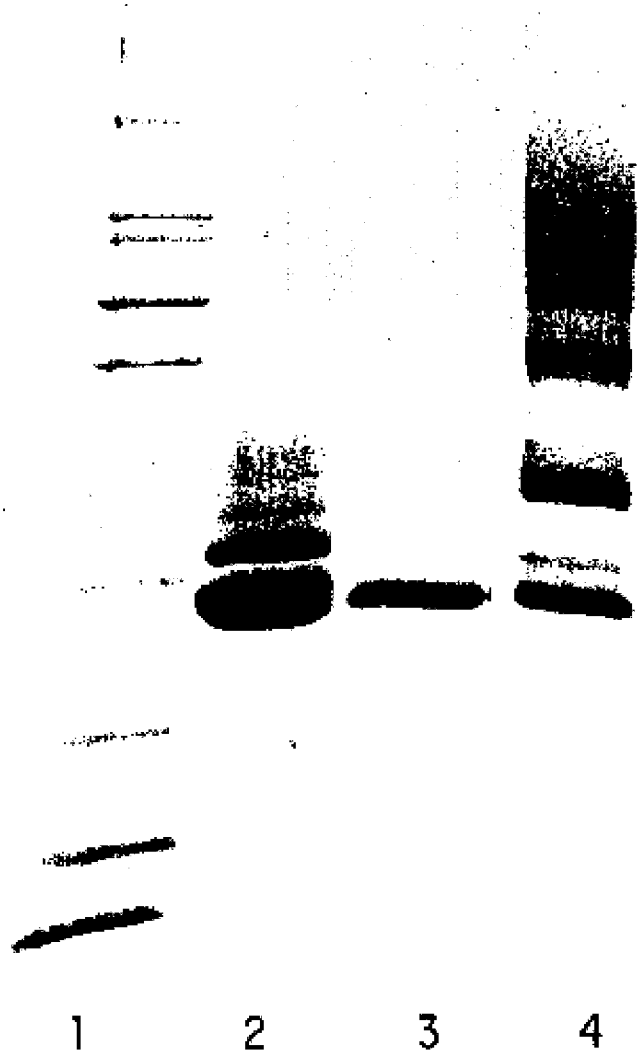
FIG. 12. SDS-PAGE analysis of the fractions from size exclusion chromatography after PEGylation of glyco-CC49/2 (EN279). Lane 1, molecular weight marker; Lane 2, native unPEGylated gCC49/2 (nonglycosylated and glycosylated fractions); Lane 3, low molecular weight fraction (nonglycosylated SCA); Lane 4, high molecular weight fraction (PEGylated and glycosylated single chain gCC49/2).

The reaction product was then analyzed on SDS-polyacrylamide gel and the size exclusion chromatography analysis. SEC chromatography analysis of the reaction mixture showed the appearance of high molecular weight peaks in addition to the low molecular weight non-glycosylated peak which was the only peak before PEGYLATION (FIG. 11A). FIGS. 11B and 12 indicate that the PEGYLATION reaction is specific for the carbohydrate moiety and does not affect the single chain antigen binding molecule that contains no carbohydrate.

Example 5
Site Specific PEGylation of Triple Site-Single Chain gCC49/3 by PEG-Hydrazide The purified gCC49/3 (EN280) was concentrated to 2 mg/ml in 10 mM sodium acetate buffer pH 7. Just before the PEGYLATION reaction, the pH was adjusted to 5.5 by adding 1/10 volume of 1 M sodium acetate pH 5.5. Fresh sodium periodate prepared in acetate buffer pH 5.5 was then added to a final concentration of 10 mM. The protein was then oxidized for 1 hour in the dark at room temperature. At the end of the reaction, the sample was loaded onto a size exclusion column to remove unreacted sodium periodate. The protein was then concentrated to 2.5 mg/ml.

PEG-hydrazide (5000 molecular weight) (Shearwater) made in the same buffer, at a molar excess of 140-fold over that of the protein, was added to the protein. The reaction was allowed to proceed at room temperature (25° C.) with shaking for 2.5 hours.

Sodium borohydride in PBS was added to the reaction mixture to a final concentration of 10 mM and the mixture was stirred for 10 min at room temperature.

Figure 13:
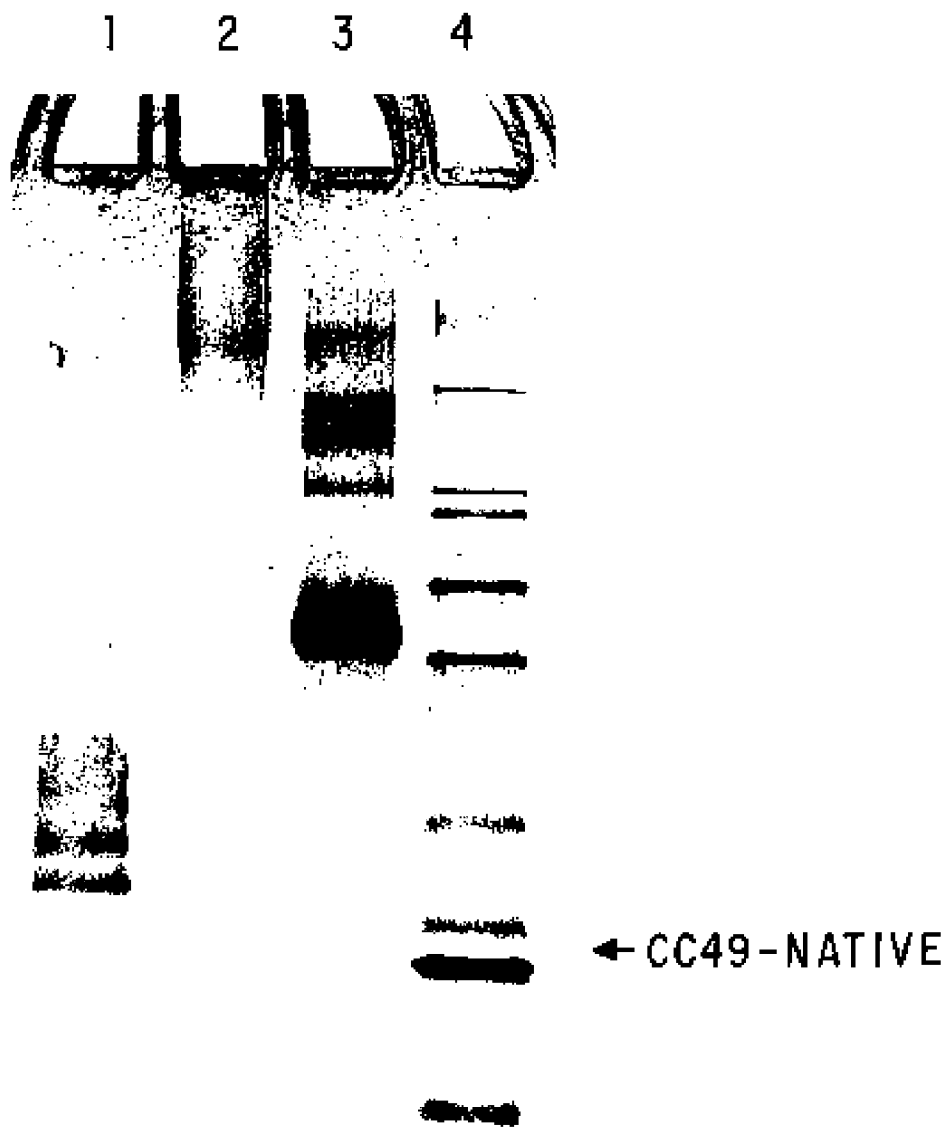
FIG. 13. SDS-PAGE analysis of gCC49/3 (glyco-CC49/triple sites) (EN280) and PEGylated gCC49/3. Conditions for PEGylation of the glycosylated CC49/3 were as described in Example 5. Lane 1, native un-PEGylated glycosylated CC49/3; Lane 2, gCC49/3-HZ5,000-PEG (highly PEGylated fraction); Lane 3, gCC49/3-HZ5,000-PEG (less PEGylated fraction); Lane 4, molecular weight marker (116.3, 97.4, 66.3, 55.4, 36.5, 31, 26.5 (CC29/218-native), 21.5, 14.4, 6 kDa). Both the highly PEGylated and less PEGylated fractions of the PEGylated and glycosylated CC49/3 had molecular weights much higher than that of the un-PEGylated glycosylated CC49/3.

The reaction product was fractionated on a size exclusion column. The purified products were than analyzed by SDS-PAGE (FIG. 13). SDS-PAGE analysis of glycosylated CC49/3, which either was unmodified or modified with PEG, shows that the PEG modified, glycosylated CC49/3 has a much higher molecular weight than the unmodified species. This indicates that glycosylated CC49/3 is also capable of being PEGylated.

Example 6
Circulation Life of Glyco-SCA and PEG-Glyco-SCA

Figure 14:
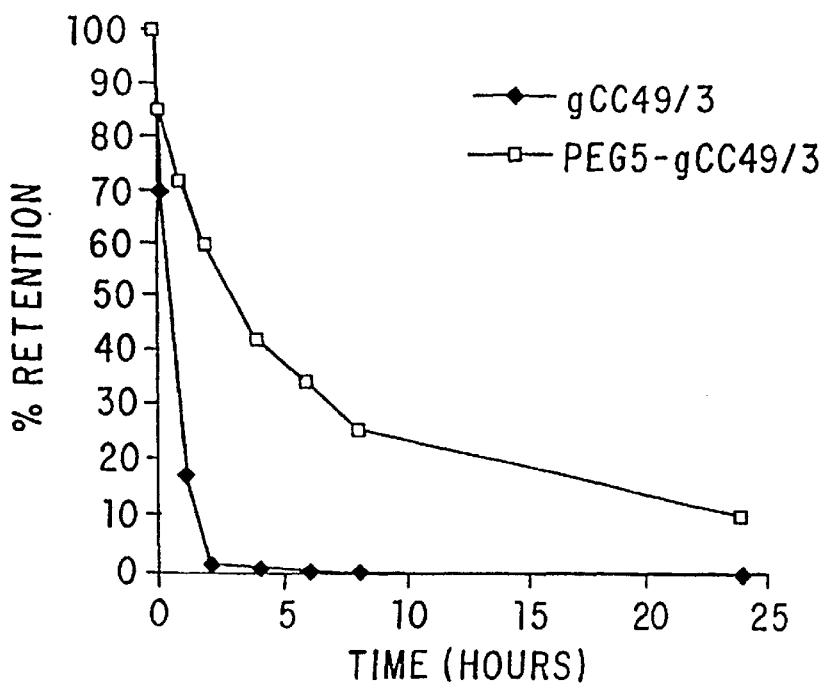
FIG. 14. Circulation life of Glyco-SCA and PEG-Glyco-SCA. ♦=gCC49/3 (EN280); ■=PEG5-gCC49/3. Details are described in Example 6.

Sixty µg of glycosylated SCA purified from *Pichia pastoris* strain EN280, or sixty micrograms of this Glyco-SCA which was PEG-modified, were injected intravenously at time 0 into ICR (CD-1) female mice (Harlan-25 g, 7–8 weeks old). Mice were bled at the time points indicated in FIG. 14. The percent retention in plasma was quantitated by ELISA methods. For the PEG-modified conjugate, Glyco-CC49/218 SCA was conjugated to PEG-hydrazide of molecular mass 5,000 (the protocol is described in Zalipsky, S., et al., PCT WO 92/16555, which disclosure is incorporated herein by reference). The average PEG:SCA molar ratio in the tested PEG-Glyco-SCA conjugate was approximately 4:1.

Example 7
Pharmacokinetics of Plasma Retention of SCA and PEG-SCA

Figure 15:
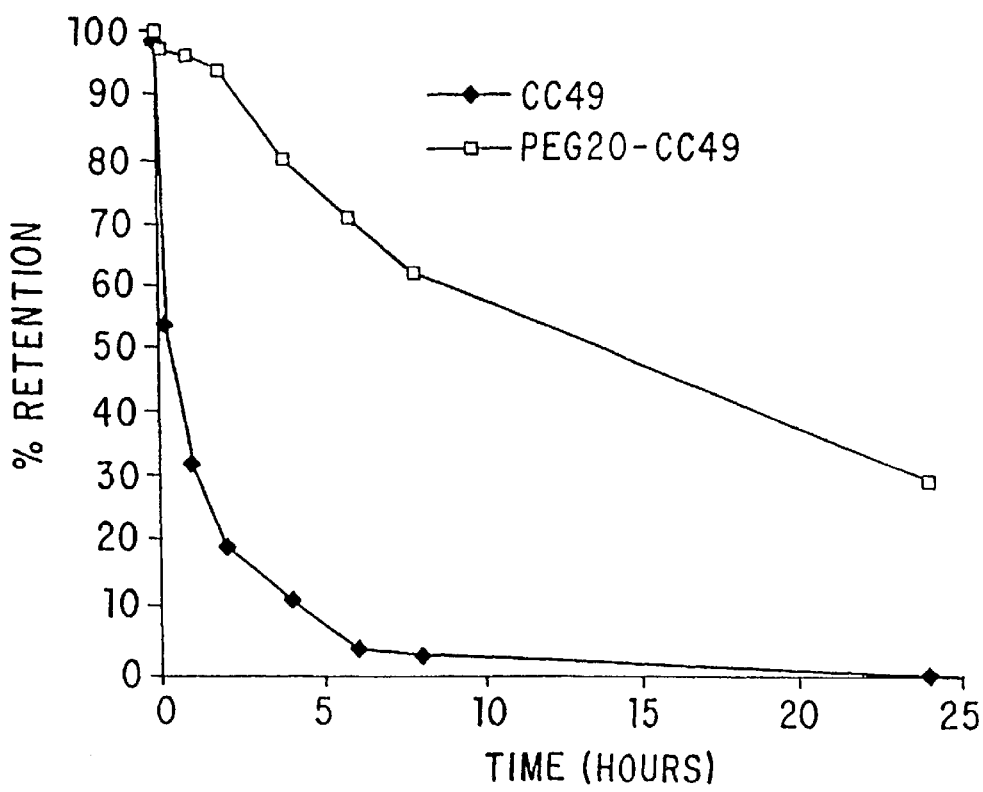
FIG. 15. Pharmacokinetics of Plasma Retention of SCA and PEG-SCA. ♦=CC49; and ■=PEG20-CC49. Details are described in Example 7.

Sixty µg of CC49/218 SCA protein or 60 µg of PEG-modified SCA protein were injected intravenously at time 0 into ICR (CD-1) female mice (Harlan –25 g, 7–8 weeks old). Mice were bled at the time points indicated in FIG. 15. The percent retention in plasma was quantitated by ELISA methods. For the PEG-modified conjugate, CC49/218 SCA was conjugated to SC-PEG of molecular mass 20,000 (the protocol is described in U.S. Pat. No. 5,122,614, which disclosure is incorporated herein by reference). The average PEG:SCA molar ratio in the tested PEG-SCA conjugate was approximately 1:1.

Example 8
Affinity Constant ($K_d$) Determinations of Glycosylated and PEGylated CC49 SCA Competition ELISA methods were performed, as according to Harlow and Lane, using biotinylated CC49 SCA, to determine the affinity constants ($K_d$). The results are provided below in Table 3.

TABLE 3

Summary of PEG-Glyco-CC49/Triple Site Binding Data

| Sample | $K_d$ (nM) | PEG |
|---|---|---|
| Bio-CC49 | 6.2 | none |
| Native-CC49 | 3.60 | none |
| Native GC | 7.34 | none |
| P1B | 48.37 | low~3 |
| P1A | 51.54 | medium |
| Z919 | 341.00 | high > 8 |

The non-PEGylated CC49 SCA (Native-CC49), the biotinylated CC49 SCA (Bio-CC49), and the Triple-site Glycosylated CC49 SCA (Native GC; EN280) all have quite similar $K_d$ values of 3.6 nM, 6.2 nM, and 7.34 nM respectively. The PEGylated versions of the Triple-site Glyco-SCA showed reduced but substantial mucin-binding affinity. The P1B preparation with approximately 3 PEG polymers per SCA (EN280) has a $K_d$ of 48.37 nM. The P1A preparation with a PEG/SCA (EN280) molar ratio of approximately 4–7 shows a $K_d$ of 51.54. The Z919 preparation with a PEG/SCA (EN280) molar ratio of >8 gives a $K_d$ of 341 nM.

Figure 16:
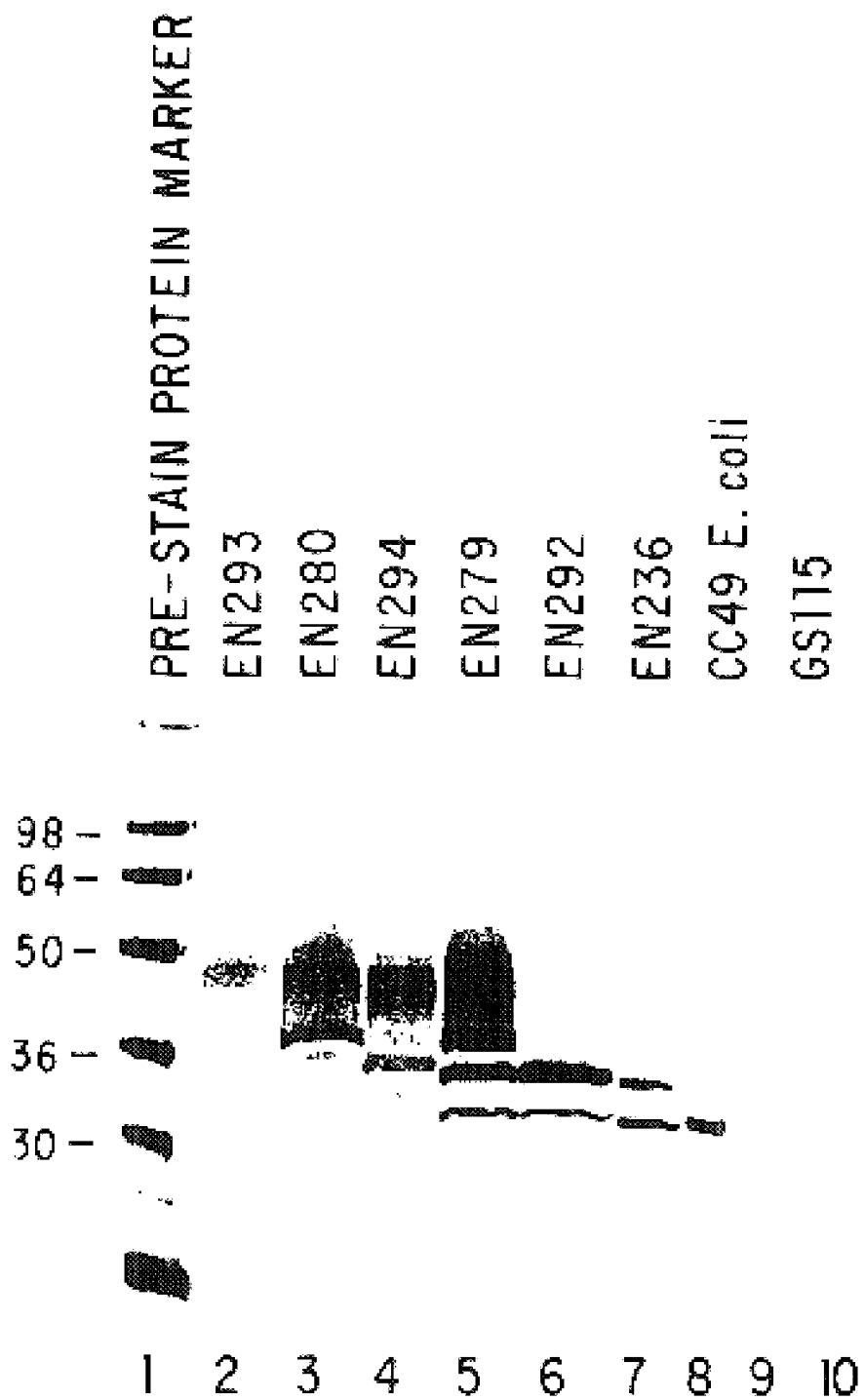
FIG. 16. Western blot of SCAs: Lanes 1 and 10, Mol. Wt. Markers; Lane 2, EN293; Lane 3, EN280; Lane 4, EN294; Lane 5, EN279; Lane 6, EN292; Lane 7, EN236; Lane 8, *E. coli* CC49; Lane 9, GS115.

Example 9
SCA Having an Addition of Five Residues Following the C-terminus N-linked Glycosylation Sequence We have already established that a single tripeptide N-linked glycosylation sequence adjacent to the C-terminus of the second polypeptide followed by just one additional residue gives adequate glycosylation. About 50% of the SCA is glycosylated. Since the literature indicates that C-terminal N-linked modification is rare, we investigated, using the methods previously described, infra, whether the addition of five tailing residues, rather than just one, would promote more efficient overall core glycosylation. The result of the Western blot (FIG. 16, EN292) for this variant shows that .gtoreq.90% of the SCA is modified with apparent core glycosylation, with no evidence of hyperglycosylation. This provides an improvement for production of Glyco-SCA with N-linked core glycosylation. The gene sequence used for this variant is as follows.

Pichia Strain Number EN292

```
-Ser Val Thr Val Ser Asn Lys Thr Ser Gly Ser Thr Ser End    (SEQ ID NO: 25)

-TCA CTC ACC GTC TCC AAC AAG ACC TCT GGT TCC ACC TCT TAA    (SEQ ID NO: 24)
```

Five total amino acids follow the initial N-linked tripeptide glycosylation sequence which is underlined. The last five residues of the unmodified CC49 SCA are indicated in bold type.

Example 10
SCA Having Three Tandem N-linked Glycosylation Sequences Adjacent to the C-terminus We have already shown that a triple-sequence variant adjacent to the C-termninus (containing two tandem plus one overlapping site) produces nearly complete overall glycosylation with predominant hyperglycosylation. We wished to next investigate whether a purely three tandem site version of this would give similar results. As shown in the Western Blot (FIG. 16, EN293), the three tandem sequence version produced complete modification which is exclusively in the hyperglycosylation category. This appears to be a more homogeneous product than the previous triple-site version by Western. However, our initial results indicate that overall expression is reduced. Hence, this may be a potential improvement in the triple sequence approach if expression can be improved. The gene sequence for this variant is shown below with notations as in Example 9.
Pichia Strain Number EN293

```
--Ser Val Thr Val Ser Asn Lys Thr Asn Ala Thr Asn Ala Thr Ser End    (SEQ ID NO: 27)

--TCA GTC ACC GTC TCC AAC AAG ACC AAT GCT ACC AAT GCC ACT TCT TAA    (SEQ ID NO: 26)
```

Example 11
SCA Having Two Overlapping Glycosylation Sequences Adjacent to the C-terminus We have already shown that an SCA having two tandem N-linked tripeptide sequences adjacent to the C-terminus of the second polypeptide produce .about.70–90% total modification with both two-site core glycosylation and some hyperglycosylation present. Additionally, a small amount of the unmodified SCA is observed. We next investigate here a two tripeptide sequence version adjacent to the C-terminus which has overlapping tripeptide sequences rather than tandem sequences. As seen on the Western Blot (FIG. 16, EN294), this variant produced no unmodified SCA, but produced predominately hyperglycosylated SCA with some apparent two-site core modification as judged by the molecular weights of these products on the SDS-PAGE gel used for the Western blot. This result shows that the phenomenon of "hyperglycosylation" in Pichia can be efficiently induced in Pichia by the minimum overlapping two-site sequence Asn-Asn-Thr-Thr (residues 9–12 of SEQ ID NO: 29) placed just one residue from the C-terminus. In contrast, a similar single-sequence version shows relatively less overall modification and essentially no detectable hyperglycosylation. The gene sequence for this variant is shown below with notations as in Example 9.
Pichia Strain EN294

```
-Ser Val Thr Val Ser Ser Lys Thr Asn Asn Thr Thr Ser End    (SEQ ID NO: 29)

-TCA GTC ACC GTC TCC TCT AAG ACC AAC AAT ACT ACC TCT TAA    (SEQ ID NO: 28)
```

Figure 17:
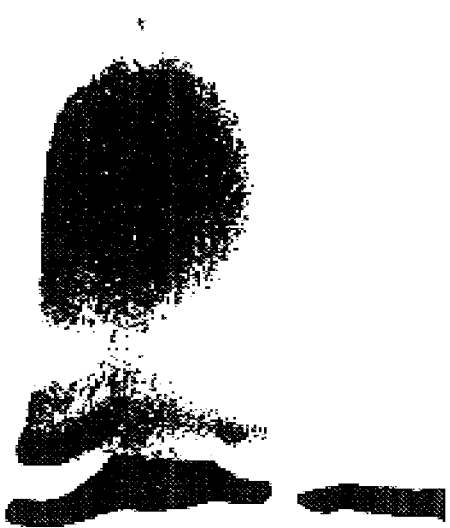
FIG. 17. Western blot of EN290 (three glycosylation sequences in linker region) and EN225 (CC49 parent). Mol. wt. markers are indicated (27 kDa, 30 kDa, and 43 kDa).

Example 12
SCA Having Three N-Linked Glycosylation Sequence in the Linker Region We have previously found evidence of inefficient glycosylation in a single N-linked tripeptide sequence engineered into the 218 linker of CC49/218 SCA. We further investigated the glycosylation of a triple tripeptide sequence inserted into the SmaI site of the 218 linker. The Western blot (FIG. 17, EN290) showed that a heterogeneous mixture of unmodified, core modified, and hyperglycosylated SCA was observed. Preliminary ELISA confirms the retention of mucin-binding activity. Hence this result shows that active Glyco-SCA can be produced from Pichia with the N-linked site(s) in the linker. However, our C-terminal data look cleaner overall. The gene sequence of this variant is as follows with the flanking 218 linker sequence opened at the SmaI site shown in bold.

Pichia Strain EN290

```
                                                    (SEQ ID NO: 31)
-Pro Asn Lys Thr Asn Asn Thr Thr Gly- (SEQ ID NO: 30)
-CCC AAC AAG ACC AAC AAT ACT ACC GGG-
```

Example 13
SCA Having Six N-linked Glycosylation Sequences in the Linker Region We also inserted six N-linked sequences into the SmaI site of the 218 linker. A Western blot indicated that expression was poor but overall glycosylation appears complete, although mostly core 1-site. Hence, this variant could be of value if expression levels can be improved. Once again, it seems that the C-terminal versions may be easier to work with. The gene sequence for this variant is as follows with the flanking 218 linker sequence opened at the SmaI site shown in bold.

Pichia Strain EN291

-Pro Asn Lys Thr Asn Asn Thr Thr Asn Lys Thr Asn Asn Thr Thr Gly- (SEQ ID NO: 33)

-CCC AAC AAG ACC AAC AAT ACT ACC AAC AAG ACC AAC AAT ACT ACC GGG- (SEQ ID NO: 32)

ELISA results show that each of the variants in Examples 9–13 described above maintains mucin-binding specificity. The Coomassie stained SDS-PAGE gels used for the Western blots were also examined for relative expression yields. Pichia vector pHIL-S1 was used as previously for this work.

It will be appreciated by those skilled in the art that the invention can be performed within a wide range of equivalent parameters of composition, concentrations, modes of administration, and conditions without departing from the spirit or scope of the invention or any embodiment thereof.

All documents, e.g., scientific publications, patents and patent publications recited herein, are hereby incorporated by reference in their entirety to the same extent as if each individual document was specifically and individually indicated to be incorporated by reference in its entirety.

What is claimed is:

1. A polynucleotide encoding a single-chain antigen-binding polypeptide comprising:
   (a) a first polypeptide comprising an antigen-binding portion of a variable region of an antibody heavy or light chain; and
   (b) a second polypeptide comprising an antigen-binding portion of a variable region of an antibody heavy or light chain; and
   (c) a peptide linker linking the first and second polypeptides into a single chain polypeptide having an antigen-binding site, wherein the encoded single-chain antigen-binding polypeptide comprises at least one tripeptide comprising Asn-Xaa-Yaa, wherein Xaa is an amino acid other than proline and Yaa is threonine or seine, and the Asn residue of the tripeptide is located at a position selected from the group consisting of
   (i) amino acid position 11, 12, 13, 14 or 15 of the light chain variable region;
   (ii) amino acid position 77, 78 or 79 of the light chain variable region;
   (iii) amino acid position 11, 12, 13, 14 or 15 of the heavy chain variable region;
   (iv) amino acid position 82B, 82C or 83 of said heavy chain variable region;
   (v) any amino acid position of the peptide linker;
   (vi) an amino acid position that is adjacent to the C-terminus of the second polypeptide; and combinations thereof, and wherein the encoded single-chain antigen-binding polypeptide is capable of being glycosylated at the Asn residue of the tripeptide when expressed by a suitable host cell.

2. The polynucleotide of claim 1, wherein the encoded single-chain antigen-binding polypeptide comprises at least two tripeptides in tandem such that the respective Asn residues of the tripeptides are separated by two amino acid residues.

3. The polynucleotide of claim 2, wherein the encoded single-chain antigen-binding polypeptide has three tripeptides in tandem.

4. The polynucleotide of claim 1, wherein the encoded single-chain antigen-binding polypeptide comprises at least one set of two overlapping tripeptides such that the respective Asn residues of the tripeptides are adjacent.

5. The polynucleotide of claim 1, wherein the encoded single-chain antigen-binding polypeptide comprises (A) at least two tripeptides in tandem wherein the Asn residues of each respective tripeptide are separated by two amino acid residues and (B) at least one set of two overlapping tripeptides wherein the respective Asn residues of each tripeptide are adjacent.

6. The polynucleotide of claim 1, wherein the encoded single-chain antigen-binding polypeptide comprises at least two sets of two tandem tripeptides and at least two sets of two overlapping tripeptides.

7. The polynucleotide of claim 1, wherein the tripeptide comprises an Asn residue located at a position selected from the group consisting of
(i') amino acid position 12 of the light chain variable region;
(ii') amino acid position 77 of the light chain variable region;
(iii') amino acid position 13 of the heavy chain variable region;
(iv') amino acid position 82B of the heavy chain variable region;
(v') amino acid position 2 of the peptide linker;
(vi') an amino acid position that is adjacent to the C-terminus of the second polypeptide; and combinations thereof.

8. The polynucleotide of claim 1, wherein the second polypeptide of the encoded single-chain antigen-binding polypeptide comprises a C-terminus native to the second polypeptide.

9. The polynucleotide of claim 8, wherein the C-terminus of the second polypeptide comprises a deletion of one or a plurality of amino acid residue(s), such that, when the encoded single-chain antigen-binding protein is glycosylated, the remaining N-terminus amino acid residues of the second polypeptide are sufficient for the single-chain antigen-binding polypeptide to be capable of binding an antigen.

10. The polynucleotide of claim 8, wherein the C-terminus of the second polypeptide comprises an addition of one or a plurality of amino acid residue(s), such that when the encoded single-chain antigen-binding polypeptide is glycosylated, it is capable of binding an antigen.

11. The polynucleotide of claim 8, 9, or 10, wherein the Asn residue of the tripeptide is located adjacent to the C-terminus of the second polypeptide and the C-terminus tripeptide is followed by at least one additional amino acid residue.

12. The polynucleotide of claim 11, wherein the C-terminus tripeptide is followed by five amino acid residues.

13. The polynucleotide of claim 1 which is DNA.

14. The polynucleotide of claim 1 which is RNA.

15. A replicable cloning or expression vector comprising the polynucleotide of claim 1.

16. The vector of claim 15 which is a plasmid.

17. An isolated host cell transformed with the vector of claim 15.

18. A host cell comprising the vector of claim 15 that is selected from the group consisting of a plant cell, a bacterial cell, a fungal cell, an insect cell, and a cell of a mammalian cell line.

19. The host cell of claim 18 that is a yeast cell.

20. A method of producing a glycosylated single-chain antigen-binding polypeptide, the method comprising: culturing a host cell comprising the vector of claim 15, so as to produce the glycosylated single-chain antigen-binding polypeptide.

21. The method of claim 20, wherein the single-chain antigen-binding polypeptide comprises at least two tripeptide glycosylation sequences in tandem such that the Asn residues of the respective tripeptides are separated by two amino acid residues.

22. The method of claim 20, wherein the single-chain antigen-binding polypeptide comprises at least one set of two overlapping tripeptide glycosylation sequences such that the Asn residues of the respective tripeptides are adjacent.

23. The method of claim 20, wherein the single-chain antigen-binding polypeptide comprises
(A) at least two tripeptide glycosylation sequences in tandem such that the Asn residues of the respective tripeptides are separated by two amino acid residues and
(B) at least one set of two overlapping tripeptide glycosylation sequences such that the Asn residues of the respective tripeptides are adjacent.

24. The method of claim 20, wherein the single-chain antigen-binding polypeptide comprises an Asn residue located at a position selected from the group consisting of
(i') amino acid position 12 of the light chain variable region;
(ii') amino acid position 77 of the light chain variable region;
(iii') amino acid position 13 of the heavy chain variable region;
(iv') amino acid position 82B of the heavy chain variable region;
(v') amino acid position 2 of the peptide linker;
(vi') an amino acid position that is adjacent to the C-terminus of the second polypeptide (b); and
(vii') combinations thereof.

25. The method of claim 20, wherein the host cell is capable of catalyzing glycosylation.

26. The method of claim 25, wherein the host cell is selected from the group consisting of a plant cell, a bacterial cell, a fungal cell, an insect cell and a cell of a mammalian cell line.

27. The method of claim 26, wherein the host cell is *Pichia pastoris*.

28. The method of claim 20, wherein the first polypeptide encoded by the polynucleotide comprises the antigen binding portion of the variable region of an antibody light chain and the second polypeptide encoded by the polynucleotide comprises the antigen binding portion of the variable region of an antibody heavy chain.

29. The method claim 20, wherein the second polypeptide comprises a C-terminus that is native to the second polypeptide.

30. The method claim 20, wherein the second polypeptide comprises a C-terminus that comprises a deletion of one or a plurality of amino acid residue(s), such that remaining N-terminus amino acid residues of the second polypeptide are sufficient for the glycosylated single-chain antigen-binding polypeptide to be capable of binding an antigen.

31. The method of claim 20, wherein the second polypeptide comprises a C-terminus that comprises an addition of one or a plurality of amino acid residue(s), such tat the glycosylated single-chain antigen-binding polypeptide is capable of binding an antigen.

32. A method of producing a polypeptide having increased glycosylation, comprising:
(a) providing a polynucleotide encoding the polypeptide wherein the encoded polypeptide comprises at least two tripeptides comprising Asn-Xaa-Yaa, wherein Xaa is an amino acid other than proline and Yaa is threonine or serine, and wherein the tripeptides are in tandem such that the Asn residues of each respective tripeptide are separated by two amino acid residues; and (b) expressing the polynucleotide in a host cell capable of attaching a carbohydrate moiety at the Asn residues.

33. A method of producing a polypeptide having increased glycosylation, comprising:

(a) providing a polynucleotide encoding the polypeptide, wherein the polypeptide comprises at least one set of two tripeptides comprising Asn-Xaa-Yaa, wherein Xaa is an amino acid other than proline and Yaa is threonine or serine, and wherein the two tripeptides overlap such that the Asn residues of the respective tripeptides are adjacent; and (b) expressing the polynucleotide in a host cell capable of attaching a carbohydrate moiety at the Asn residues.

34. A method of producing a polypeptide having increased glycosylation, comprising:

(a) providing a polynucleotide encoding the polypeptide, wherein the polypeptide comprises at least two tripeptides comprising, Asn-Xaa-Yaa, wherein Xaa is an amino acid other than proline and Yaa is threonine or serine, and wherein the tripeptides are in tandem such that the Asn residues of the respective tripeptides are separated by two amino acid residues;

(b) further providing that the encoded polypeptide comprises at least one additional set of two tripeptide glycosylation sequences, wherein the two tripeptide glycosylation sequences overlap such that the Asn residues of the respective triptides are adjacent; and (c) expressing the polynucleotide in a host cell capable of attaching a carbohydrate moiety at the Asn residues.

35. The polynucleotide of claim 1, wherein the tripeptide comprises an Asn residue that is located at an amino acid position selected from the group consisting of amino acid position 11, 12, 13, 14 and 15, of the light chain variable region or the heavy chain variable region.

36. The polynucleotide of claim 35, wherein the tripeptide comprises an Asn residue that is located at amino acid position 12 of the light chain variable region.

37. The polynucleotide of claim 35, wherein the tripeptide comprises an Asn residue that is located at amino acid position 13 of the heavy chain variable region.

38. The polynucleotide of claim 1, wherein the tripeptide comprises an Asn residue that is located at an amino acid position selected from the group consisting of amino acid position 77, 78 and 79 of the light chain variable region.

39. The polynucleotide of claim 38, wherein the tripeptide comprises an Asn residue that is located at amino acid position 77 of the light chain variable region.

40. The polynucleotide of claim 1, wherein the tripeptide comprises an Asn residue that is located at an amino acid position selected from the group consisting of amino acid position 82B, 82C and 83 of the heavy chain variable region.

41. The polynucleotide of claim 40, wherein the tripeptide comprises an Asn residue that is located at amino acid position 82B of the heavy chain variable region.

42. The polynucleotide of claim 1, wherein the tripeptide comprises an Asn residue that is located at any amino acid position of the peptide linker.

43. The polynucleotide of claim 42, wherein the tripeptide comprises an Asn residue that is located at amino acid position 2 of the peptide linker.

44. The polynucleotide of claim 1, wherein the tripeptide comprises an Asn residue that is located at an amino acid position adjacent to the C-terminus of the second polypeptide.

45. The polynucleotide of claim 1, wherein the peptide linker ranges from 2 to 50 amino acid residues in length.

46. The polynucleotide of claim 1, wherein the peptide linker ranges from 10 to 30 amino acid residues in length.

47. The polynucleotide of claim 1, wherein the peptide linker is less than 10 amino acid residues in length.

48. The host cell of claim 19, that is *Pichia pastoris*.

49. The host cell of claim 18, that is a plant cell or a fungal cell.

50. The host cell of claim 18, that is a bacteria selected from the group consisting of Neisseria, Mycobacteria, Streptococci, Chlamydia, and *Escherichia coli*.

51. The host cell of claim 18, that is *Escherichia coli*.

52. The host cell of claim 18, that is *Escherichia coli* strain (GX9251 or *Pichia pastoris* EN225.

53. The method of claim 26, wherein the host cell is a plant cell or a fungal cell.

54. The method of claim 26, wherein the host cell is a bacteria selected from the group consisting of Neisseria, Mycobacteria, Streptococci, Chlamydia, and *Escherichia coli*.

55. The method of claim 26, wherein the host cell is *Escherichia coli*.

56. The method of claim 26, wherein the host cell is *Escherichia coli* strain GX9251 or *Pichia pastoris* EN225.

57. The replicable cloning or expression vector of claim 15 that is selected from the group consisting of a yeast 2 micron circle, expression plasmid YEP13, expression plasmid YCP and expression plasmid YRP.

58. The replicable cloning or expression vector of claim 15 that is a vector selected from the group consisting of a yeast 2 micron circle, expression plasmid YEP13, expression plasmid YCP and expression plasmid YRP.

59. The replicable cloning or expression vector of claim 15 that is selected from the group consisting of PQE70, PQE60 and PQE-9, pBS vectors, Phagescript vectors, Bluescript vectors, pNH8A, pNH16a, pNH18A, pNH46A, ptre99a, pKK223-3, pKK233-3, pDR540, pRIT5.

60. The replicable cloning or expression vector of claim 15 that is a eukaryotic vector selected from the group consisting of pWLNEO, pSV2CAT, pOG44, pXT1 and pSG, pSVK3, pBPV, pMSG and pSVL.

61. The replicable cloning or expression vector of claim 15 that is selected, from the group consisting of pHIL-S1 and pPIC9.

62. The method of claim 32 wherein the host cell is selected from the group consisting of a plant cell, a bacterial cell, a fungal cell, an insect cell, and a cell of a mammalian cell line.

63. The method of claim 33 wherein the host cell is selected from the group consisting of a plant cell, a bacterial cell, a fungal cell, an insect cell, and a cell of a mammalian cell line.

64. The method of claim 34 wherein the host cell is selected from the group consisting of a plant cell, a bacterial cell, a fungal cell, an insect cell, and a cell of a mammalian cell line.

65. The method of claim 32 wherein the host cell is *Pichia pastoris* or *Escherichia coli*.

66. The method of claim 33 wherein the host cell is *Pichia pastoris* or *Escherichia coli*.

67. The method of claim 34 wherein the host cell is *Pichia pastoris* or *Escherichia coli*.

* * * * *

SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
      (A) LENGTH: 758 base pairs
      (B) TYPE: nucleic acid
      (C) STRANDEDNESS: both
      (D) TOPOLOGY: both (ii) MOLECULE TYPE: cDNA (ix) FEATURE:
      (A) NAME/KEY: CDS
      (B) LOCATION: 1..747

(xi) SEQUENCE DESCRIPTION: SEQ ID NO: 1:

```
GAC GTC GTG ATG TCA CAG TCT CCA TCC TCC CTA CCT GTG TCA GTT GGC        48
Asp Val Val Met Ser Gln Ser Pro Ser Ser Leu Pro Val Ser Val Gly
 1               5                  10                  15

GAG AAG GTT ACT TTG AGC TGC AAG TCC AGT CAG AGC CTT TTA TAT AGT        96
Glu Lys Val Thr Leu Ser Cys Lys Ser Ser Gln Ser Leu Leu Tyr Ser
                20                  25                  30

GGT AAT CAA AAG AAC TAC TTG GCC TGG TAC CAG CAG AAA CCA GGG CAG       144
Gly Asn Gln Lys Asn Tyr Leu Ala Trp Tyr Gln Gln Lys Pro Gly Gln
            35                  40                  45

TCT CCT AAA CTG CTG ATT TAC TGG GCA TCC GCT AGG GAA TCT GGG GTC       192
Ser Pro Lys Leu Leu Ile Tyr Trp Ala Ser Ala Arg Glu Ser Gly Val
        50                  55                  60

CCT GAT CGC TTC ACA GGC AGT GGA TCT GGG ACA GAT TTC ACT CTC TCC       240
Pro Asp Arg Phe Thr Gly Ser Gly Ser Gly Thr Asp Phe Thr Leu Ser
 65                  70                  75                  80

ATC AGC AGT GTG AAG ACT GAA GAC CTG GCA GTT TAT TAC TGT CAG CAG       288
Ile Ser Ser Val Lys Thr Glu Asp Leu Ala Val Tyr Tyr Cys Gln Gln
                85                  90                  95

TAT TAT AGC TAT CCC CTC ACG TTC GGT GCT GGG ACC AAG CTT GTG CTG       336
Tyr Tyr Ser Tyr Pro Leu Thr Phe Gly Ala Gly Thr Lys Leu Val Leu
            100                 105                 110

AAA GGC TCT ACT TCC GGT AGC GGC AAA CCC GGG AGT GGT GAA GGT AGC       384
Lys Gly Ser Thr Ser Gly Ser Gly Lys Pro Gly Ser Gly Glu Gly Ser
        115                 120                 125

ACT AAA GGT CAG GTT CAG CTG CAG CAG TCT GAC GCT GAG TTG GTG AAA       432
Thr Lys Gly Gln Val Gln Leu Gln Gln Ser Asp Ala Glu Leu Val Lys
130                 135                 140
```

```
CCT GGG GCT TCA GTG AAG ATT TCC TGC AAG GCT TCT GGC TAC ACC TTC      480
Pro Gly Ala Ser Val Lys Ile Ser Cys Lys Ala Ser Gly Tyr Thr Phe
145                 150                 155                 160

ACT GAC CAT GCA ATT CAC TGG GTG AAA CAG AAC CCT GAA CAG GGC CTG      528
Thr Asp His Ala Ile His Trp Val Lys Gln Asn Pro Glu Gln Gly Leu
                165                 170                 175

GAA TGG ATT GGA TAT TTT TCT CCC GGA AAT GAT GAT TTT AAA TAC AAT      576
Glu Trp Ile Gly Tyr Phe Ser Pro Gly Asn Asp Asp Phe Lys Tyr Asn
            180                 185                 190

GAG AGG TTC AAG GGC AAG GCC ACA CTG ACT GCA GAC AAA TCC TCC AGC      624
Glu Arg Phe Lys Gly Lys Ala Thr Leu Thr Ala Asp Lys Ser Ser Ser
        195                 200                 205

ACT GCC TAC GTG CAG CTC AAC AGC CTG ACA TCT GAG GAT TCT GCA GTG      672
Thr Ala Tyr Val Gln Leu Asn Ser Leu Thr Ser Glu Asp Ser Ala Val
    210                 215                 220

TAT TTC TGT ACA AGA TCC CTG AAT ATG GCC TAC TGG GGT CAA GGA ACC      720
Tyr Phe Cys Thr Arg Ser Leu Asn Met Ala Tyr Trp Gly Gln Gly Thr
225                 230                 235                 240

TCA GTC ACC GTC TCC AAC AAG ACC AGT TAATAGGATC C                     758
Ser Val Thr Val Ser Asn Lys Thr Ser
                245
```

(2) INFORMATION FOR SEQ ID NO: 2:

(i) SEQUENCE CHARACTERISTICS:
        (A) LENGTH: 249 amino acids
        (B) TYPE: amino acid
        (D) TOPOLOGY: linear (ii) MOLECULE TYPE: protein (xi) SEQUENCE DESCRIPTION: SEQ ID NO: 2:

```
Asp Val Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Gly Ser Thr Ser Gly Ser Gly Lys Pro Gly Ser Gly Glu Gly Ser
        115                 120                 125

Thr Lys Gly Gln Val Gln Leu Gln Gln Ser Asp Ala Glu Leu Val Lys
    130                 135                 140

Pro Gly Ala Ser Val Lys Ile Ser Cys Lys Ala Ser Gly Tyr Thr Phe
145                 150                 155                 160

Thr Asp His Ala Ile His Trp Val Lys Gln Asn Pro Glu Gln Gly Leu
                165                 170                 175

Glu Trp Ile Gly Tyr Phe Ser Pro Gly Asn Asp Asp Phe Lys Tyr Asn
            180                 185                 190

Glu Arg Phe Lys Gly Lys Ala Thr Leu Thr Ala Asp Lys Ser Ser Ser
        195                 200                 205
```

```
Thr Ala Tyr Val Gln Leu Asn Ser Leu Thr Ser Glu Asp Ser Ala Val
    210                 215                 220

Tyr Phe Cys Thr Arg Ser Leu Asn Met Ala Tyr Trp Gly Gln Gly Thr
225                 230                 235                 240

Ser Val Thr Val Ser Asn Lys Thr Ser
                245
```

(2) INFORMATION FOR SEQ ID NO: 3:

(i) SEQUENCE CHARACTERISTICS:
        (A) LENGTH: 263 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 3:

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Leu Val Ser Ile
            20                  25                  30

Ser Asn Tyr Leu Ala Trp Tyr Gln Gln Lys Pro Gly Lys Ala Pro Lys
        35                  40                  45

Leu Leu Ile Tyr Ala Ala Ser Ser Leu Glu Ser Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Asn Ser
                85                  90                  95

Leu Pro Glu Trp Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
        115                 120                 125

Gly Glu Val Gln Leu Val Glu Ser Gly Gly Gly Leu Val Gln Pro Gly
    130                 135                 140

Gly Ser Leu Arg Leu Ser Cys Ala Ala Ser Gly Phe Thr Phe Ser Ser
145                 150                 155                 160

Tyr Ala Met Ser Trp Val Arg Gln Ala Pro Gly Lys Gly Leu Glu Trp
                165                 170                 175

Val Ser Val Ile Ser Gly Lys Thr Asp Gly Gly Ser Thr Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Arg Gly Arg Xaa Gly Xaa Ser Leu Ser Gly Xaa Tyr
225                 230                 235                 240

Tyr Tyr Tyr His Tyr Phe Asp Tyr Trp Gly Gln Gly Thr Leu Val Thr
                245                 250                 255

Val Ser Ser Asn Lys Thr Ser
            260
```

(2) INFORMATION FOR SEQ ID NO: 4:

(i) SEQUENCE CHARACTERISTICS:
        (A) LENGTH: 262 amino acids (B) TYPE: amino acid
(C) STRANDEDNESS: single
(D) TOPOLOGY: not relevant (ii) MOLECULE TYPE: peptide (xi) SEQUENCE DESCRIPTION: SEQ ID NO: 4:

```
Gln Ser Val Leu Thr Gln Pro Ser Val Ser Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Gly His Thr Asn Arg Pro Ala Gly Val Pro Asp Arg Phe Ser
    50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly Gly
            100                 105                 110

Ser Thr Ser Gly Ser Gly Lys Pro Gly Ser Gly Glu Gly Ser Thr Lys
            115                 120                 125

Gly Gln Val Gln Leu Leu Gln Ser Gly Ala Glu Leu Lys Lys Pro Gly
130                 135                 140

Glu Ser Leu Lys Ile Ser Cys Lys Gly Ser Gly Tyr Ser Phe Thr Ser
145                 150                 155                 160

Tyr Trp Ile Ala Trp Val Arg Gln Met Pro Gly Lys Gly Leu Glu Tyr
                165                 170                 175

Met Gly Leu Ile Tyr Pro Gly Asp Ser Asp Thr Lys Tyr Ser Pro Ser
            180                 185                 190

Phe Gln Gly Gln Val Thr Ile Ser Val Asp Lys Ser Val Ser Thr Ala
            195                 200                 205

Tyr Leu Gln Trp Ser Ser Leu Lys Pro Ser Asp Ser Ala Val Tyr Phe
    210                 215                 220

Cys Ala Arg His Asp Val Gly Tyr Cys Ser Ser Ser Asn Cys Ala Lys
225                 230                 235                 240

Trp Pro Glu Tyr Phe Gln His Trp Gly Gln Gly Thr Leu Val Thr Val
                245                 250                 255

Ser Ser Asn Lys Thr Ser
            260
```

(2) INFORMATION FOR SEQ ID NO: 5:

(i) SEQUENCE CHARACTERISTICS:
(A) LENGTH: 245 amino acids
(B) TYPE: amino acid
(C) STRANDEDNESS: single
(D) TOPOLOGY: not relevant (ii) MOLECULE TYPE: peptide (xi) SEQUENCE DESCRIPTION: SEQ ID NO: 5:

```
Asp Val Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Val
                20                  25                  30

Val Ala Trp Tyr Gln Gln Lys Pro Gly Gln Ser Pro Lys Thr Leu Ile
```

-continued

```
                35                  40                  45
Tyr Leu Ala Ser Asn Arg His Thr Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Leu Gln His Trp Ser Tyr Pro Leu
                 85                  90                  95

Thr Phe Gly Ser Gly Thr Lys Leu Glu Val Lys Gly Ser Thr Ser Gly
                100                 105                 110

Ser Gly Lys Pro Gly Ser Gly Glu Gly Ser Thr Lys Gly Glu Val Lys
                115                 120                 125

Leu Val Glu Ser Gly Gly Gly Leu Val Lys Pro Gly Gly Ser Leu Lys
                130                 135                 140

Leu Ser Cys Ala Ala Ser Gly Phe Ala Phe Ser Thr Tyr Asp Met Ser
145                 150                 155                 160

Trp Val Arg Gln Thr Pro Glu Lys Arg Leu Glu Trp Val Ala Thr Ile
                165                 170                 175

Ser Ser Gly Gly Ser Tyr Thr Tyr Tyr Leu Asp Ser Val Lys Gly Arg
                180                 185                 190

Phe Thr Ile Ser Arg Asp Ser Ala Arg Asn Thr Leu Tyr Leu Gln Met
                195                 200                 205

Ser Ser Leu Arg Ser Glu Asp Thr Ala Leu Tyr Tyr Cys Ala Pro Thr
210                 215                 220

Thr Val Val Pro Phe Ala Tyr Trp Gly Gln Gly Thr Leu Val Thr Val
225                 230                 235                 240

Ser Asn Lys Thr Ser
                245

(2) INFORMATION FOR SEQ ID NO: 6:

(i) SEQUENCE CHARACTERISTICS:
        (A) LENGTH: 12 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 6:

Gly Lys Ser Ser Gly Ser Gly Ser Glu Ser Lys Ser
 1               5                  10

(2) INFORMATION FOR SEQ ID NO: 7:

(i) SEQUENCE CHARACTERISTICS:
        (A) LENGTH: 14 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 7:

Gly Ser Thr Ser Gly Ser Gly Lys Ser Ser Glu Gly Lys Gly
 1               5                  10

(2) INFORMATION FOR SEQ ID NO: 8:

(i) SEQUENCE CHARACTERISTICS:
        (A) LENGTH: 18 amino acids
        (B) TYPE: amino acid
```

```
            (C) STRANDEDNESS: single
            (D) TOPOLOGY: not relevant (ii) MOLECULE TYPE: peptide (xi) SEQUENCE DESCRIPTION: SEQ ID NO: 8:

Gly Ser Thr Ser Gly Ser Gly Lys Ser Ser Glu Gly Ser Gly Ser Thr
1               5                   10                  15

Lys Gly (2) INFORMATION FOR SEQ ID NO: 9:

(i) SEQUENCE CHARACTERISTICS:
            (A) LENGTH: 12 amino acids
            (B) TYPE: amino acid
            (C) STRANDEDNESS: single
            (D) TOPOLOGY: not relevant (ii) MOLECULE TYPE: peptide (xi) SEQUENCE DESCRIPTION: SEQ ID NO: 9:

Gly Ser Thr Ser Gly Lys Pro Ser Glu Gly Lys Gly
1               5                   10

(2) INFORMATION FOR SEQ ID NO: 10:

(i) SEQUENCE CHARACTERISTICS:
            (A) LENGTH: 18 amino acids
            (B) TYPE: amino acid
            (C) STRANDEDNESS: single
            (D) TOPOLOGY: not relevant (ii) MOLECULE TYPE: peptide (xi) SEQUENCE DESCRIPTION: SEQ ID NO: 10:

Gly Ser Thr Ser Gly Ser Gly Lys Pro Gly Ser Gly Glu Gly Ser Thr
1               5                   10                  15

Lys Gly (2) INFORMATION FOR SEQ ID NO: 11:

(i) SEQUENCE CHARACTERISTICS:
            (A) LENGTH: 38 base pairs
            (B) TYPE: nucleic acid
            (C) STRANDEDNESS: both
            (D) TOPOLOGY: both (ii) MOLECULE TYPE: cDNA (ix) FEATURE:
            (A) NAME/KEY: CDS
            (B) LOCATION: 1..27

(xi) SEQUENCE DESCRIPTION: SEQ ID NO: 11:

TCA GTC ACC GTC TCC AAC AAG ACC AGT TAATAGGATC C          38
Ser Val Thr Val Ser Asn Lys Thr Ser
250             255

(2) INFORMATION FOR SEQ ID NO: 12:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO: 12:
```

```
Ser Val Thr Val Ser Asn Lys Thr Ser
  1               5
```

(2) INFORMATION FOR SEQ ID NO: 13:

(i) SEQUENCE CHARACTERISTICS:
        (A) LENGTH: 47 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..36

(xi) SEQUENCE DESCRIPTION: SEQ ID NO: 13:

```
TCA GTC ACC GTC TCC AAC AAG ACC AAT GCT ACC TCT TAATAGGATC        46
Ser Val Thr Val Ser Asn Lys Thr Asn Ala Thr Ser
 10              15              20

C                                                                 47
```

(2) INFORMATION FOR SEQ ID NO: 14:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO: 14:

```
Ser Val Thr Val Ser Asn Lys Thr Asn Ala Thr Ser
  1               5                  10
```

(2) INFORMATION FOR SEQ ID NO: 15:

(i) SEQUENCE CHARACTERISTICS:
        (A) LENGTH: 48 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..39

(xi) SEQUENCE DESCRIPTION: SEQ ID NO: 15:

```
TCA GTC ACC GTC TCC AAC AAG ACC AAT AAT ACT ACC TCT TAAGGATCC     48
Ser Val Thr Val Ser Asn Lys Thr Asn Asn Thr Thr Ser
         15              20              25
```

(2) INFORMATION FOR SEQ ID NO: 16:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 16:

```
Ser Val Thr Val Ser Asn Lys Thr Asn Asn Thr Thr Ser
  1               5                  10
```

(2) INFORMATION FOR SEQ ID NO: 17:

(i) SEQUENCE CHARACTERISTICS:
    (A) LENGTH: 6 amino acids
    (B) TYPE: amino acid
    (C) STRANDEDNESS: single
    (D) TOPOLOGY: not relevant (ii) MOLECULE TYPE: peptide (xi) SEQUENCE DESCRIPTION: SEQ ID NO: 17:

Asn Lys Thr Asn Ala Thr
1               5

(2) INFORMATION FOR SEQ ID NO: 18:

(i) SEQUENCE CHARACTERISTICS:
        (A) LENGTH: 7 amino acids
        (B) TYPE: amino acid
        (C) STRANDEDNESS: single
        (D) TOPOLOGY: not relevant (ii) MOLECULE TYPE: peptide (xi) SEQUENCE DESCRIPTION: SEQ ID NO: 18:

Asn Lys Thr Asn Asn Thr Thr
1               5

(2) INFORMATION FOR SEQ ID NO: 19:

(i) SEQUENCE CHARACTERISTICS:
        (A) LENGTH: 26 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 19:

CGGAATTCGA CGTCGTGATG TCACAG                                           26

(2) INFORMATION FOR SEQ ID NO: 20:

(i) SEQUENCE CHARACTERISTICS:
        (A) LENGTH: 41 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 20:

CCAGGATCCT ATTAACTGGT CTTGTTGGAG ACGGTGACTG A                          41

(2) INFORMATION FOR SEQ ID NO: 21:

(i) SEQUENCE CHARACTERISTICS:
        (A) LENGTH: 45 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 21:

CCGGGATCCT ATTAAGAGGT AGCATTGGTC TTGTTGGAGA CGGTG                      45

(2) INFORMATION FOR SEQ ID NO: 22:

(i) SEQUENCE CHARACTERISTICS:

(A) LENGTH: 46 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 22:

CCGGGATCCT TAAGAGGTAG TATTGTTGGT CTTGTTGGAG ACGGTG                46

(2) INFORMATION FOR SEQ ID NO: 23:

(i) SEQUENCE CHARACTERISTICS:
        (A) LENGTH: 45 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 23:

CCGGAATTCT ATTAAGAGGT AGCATTGGTC TTGTTGGAGA CGGTG                 45

(2) INFORMATION FOR SEQ ID NO: 24:

(i) SEQUENCE CHARACTERISTICS:
        (A) LENGTH: 42 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..39

(xi) SEQUENCE DESCRIPTION: SEQ ID NO: 24:

TCA GTC ACC GTC TCC AAC AAG ACC TCT GGT TCC ACC TCT TAA          42
Ser Val Thr Val Ser Asn Lys Thr Ser Gly Ser Thr Ser
250             255                 260

(2) INFORMATION FOR SEQ ID NO: 25:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 25:

Ser Val Thr Val Ser Asn Lys Thr Ser Gly Ser Thr Ser
  1               5                  10

(2) INFORMATION FOR SEQ ID NO: 26:

(i) SEQUENCE CHARACTERISTICS:
        (A) LENGTH: 48 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..45

(xi) SEQUENCE DESCRIPTION: SEQ ID NO: 26:

```
TCA GTC ACC GTC TCC AAC AAG ACC AAT GCT ACC AAT GCC ACT TCT        45
Ser Val Thr Val Ser Asn Lys Thr Asn Ala Thr Asn Ala Thr Ser
     15                  20                  25

TAA                                                                48
```

(2) INFORMATION FOR SEQ ID NO: 27:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO: 27:

```
Ser Val Thr Val Ser Asn Lys Thr Asn Ala Thr Asn Ala Thr Ser
 1               5                  10                  15
```

(2) INFORMATION FOR SEQ ID NO: 28:

(i) SEQUENCE CHARACTERISTICS:
        (A) LENGTH: 42 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..39

(xi) SEQUENCE DESCRIPTION: SEQ ID NO: 28:

```
TCA GTC ACC GTC TCC TCT AAG ACC AAC AAT ACT ACC TCT TAA            42
Ser Val Thr Val Ser Ser Lys Thr Asn Asn Thr Thr Ser
                20                  25
```

(2) INFORMATION FOR SEQ ID NO: 29:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 29:

```
Ser Val Thr Val Ser Ser Lys Thr Asn Asn Thr Thr Ser
 1               5                  10
```

(2) INFORMATION FOR SEQ ID NO: 30:

(i) SEQUENCE CHARACTERISTICS:
        (A) LENGTH: 27 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..27

(xi) SEQUENCE DESCRIPTION: SEQ ID NO: 30:

```
CCC AAC AAG ACC AAC AAT ACT ACC GGG                                27
Pro Asn Lys Thr Asn Asn Thr Thr Gly
     15                  20
```

-continued (2) INFORMATION FOR SEQ ID NO: 31:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO: 31:

```
Pro Asn Lys Thr Asn Asn Thr Thr Gly
 1               5
```

(2) INFORMATION FOR SEQ ID NO: 32:

(i) SEQUENCE CHARACTERISTICS:
        (A) LENGTH: 48 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..48

(xi) SEQUENCE DESCRIPTION: SEQ ID NO: 32:

```
CCC AAC AAG ACC AAC AAT ACT ACC AAC AAG ACC AAC AAT ACT ACC GGG         48
Pro Asn Lys Thr Asn Asn Thr Thr Asn Lys Thr Asn Asn Thr Thr Gly
 10               15                  20                  25
```

(2) INFORMATION FOR SEQ ID NO: 33:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO: 33:

```
Pro Asn Lys Thr Asn Asn Thr Thr Asn Lys Thr Asn Asn Thr Thr Gly
 1               5                  10                  15
```